United States Patent
Yamada et al.

(10) Patent No.: US 6,210,641 B1
(45) Date of Patent: Apr. 3, 2001

(54) AIR-FUEL RATIO CONTROL SYSTEM AND GAS SENSOR FOR ENGINES

(75) Inventors: Jun Yamada, Okazaki; Kenji Kanehara, Toyohashi; Motomasa Iizuka, Nisshin; Takeshi Mizobuchi, Nishio; Hidetaka Hayashi, Nagoya; Kouhei Yamada, Kariya; Isao Watanabe, Nagoya; Takahiko Kuroda, Toyoake, all of (JP)

(73) Assignees: Denso Corporation, Kariya; Nippon Soken, Inc., Nishio, both of (JP)

( * ) Notice: Subject to any disclaimer, the term of this patent is extended or adjusted under 35 U.S.C. 154(b) by 0 days.

(21) Appl. No.: 09/112,289

(22) Filed: Jul. 9, 1998

(30) Foreign Application Priority Data

| Jul. 9, 1997 | (JP) | 9-184088 |
| Dec. 15, 1997 | (JP) | 9-363640 |
| Dec. 22, 1997 | (JP) | 9-365806 |

(51) Int. Cl.$^7$ ............................................. G01N 27/12
(52) U.S. Cl. .................... 422/94; 422/98; 60/276; 60/285; 123/696
(58) Field of Search ............... 422/94, 98, 110, 422/111; 204/427, 429; 60/285, 276; 123/696, 695, 697

(56) References Cited

U.S. PATENT DOCUMENTS

| 4,526,001 | * | 7/1985 | Burns et al. | 60/274 |
| 4,957,705 | | 9/1990 | Uchikawa . | |
| 5,259,358 | * | 11/1993 | Chen | 123/697 |
| 5,263,464 | * | 11/1993 | Yoshida et al. | 123/674 |
| 5,271,821 | * | 12/1993 | Ogasawara et al. . | |
| 5,417,060 | * | 5/1995 | Ishida et al. | 60/276 |
| 5,459,119 | * | 10/1995 | Abe et al. | 502/326 |
| 5,586,543 | * | 12/1996 | Schnaibel et al. | 123/696 |
| 5,753,794 | * | 5/1998 | Tebbutt | 73/23.31 |
| 5,809,967 | * | 9/1998 | Masubuchi | 123/406.44 |

FOREIGN PATENT DOCUMENTS

| 1-245147 | 9/1986 | (JP) . |
| 4-303754 | 10/1992 | (JP) . |
| 6-229274 | 8/1994 | (JP) . |
| 9-126012 | 5/1997 | (JP) . |

OTHER PUBLICATIONS

J. Klimstra, "Catalytic Converters for Natural Gas Fueled Engines—A Measurement and Control Problem", SAE Technical paper Series, Nov. 2–5, 1987, pp. 1–13.

Hishinuma, et al., "Development of a New A/F Control System for Three–Way Catalyst of Stationary Gas Engines", pp. 1–6.

* cited by examiner

*Primary Examiner*—Jeffrey Snay
(74) *Attorney, Agent, or Firm*—Pillsbury Winthrop LLP

(57) ABSTRACT

An air-fuel ratio control system for a gas-fueled engine which is capable of achieving the combustion in a target air-fuel ratio to surely purify an exhaust gas through an exhaust purification catalyst. In the air-fuel ratio control system, a three-way catalytic converter is placed in an exhaust pipe of the engine and an $O_2$ sensor is located on the upstream side of the three-way catalytic converter. The $O_2$ sensor comprises an element, and an atmosphere side electrode is formed on an inner surface of the element while an exhaust gas side electrode is formed on an outer surface thereof. The exhaust gas side electrode is coated with a catalyst layer which can remove hydrogen through a catalytic reaction. A control unit of the control system controls a fuel supply quantity by a gas injector using a feedback correction coefficient on the basis of the output of the $O_2$ sensor, thereby reducing the deviation between an air-fuel ratio measured by the $O_2$ sensor and a target air-fuel ratio.

7 Claims, 44 Drawing Sheets

ATMOSPHERE

EXHAUST GAS ⇨

AIR-FUEL RATIO CONTROL SYSTEM AND GAS SENSOR FOR ENGINES

BACKGROUND OF THE INVENTION

1. Field of the Invention

The present invention relates to an air-fuel control system for a gas fueled engine applicable to motor vehicles, generation of electricity, and other fields employing a natural gas as a principal component. Further, this invention relates to an $O_2$ sensor for air-fuel ratio control for use in an internal combustion engine or the like, which is used as an air-fuel ratio sensor or the like for detecting an air-fuel ratio over a wider area, and more particularly to a gas sensor suitable for a natural-gas-fueled engine.

2. Description of the Prior Art

Recently, a requirement for the suppression or inhibition of exhaust emissions (HC, CO, $NO_x$, $CO_2$) from an internal combustion engine has increased from the viewpoint of the improvement of atmospheric conditions. For meeting this suppression requirement, much attention has been focused on a natural-gas-used motor vehicle, or a motor vehicle with an engine for cogeneration, substituted for the conventional oil-used motor vehicle. A natural-gas-fueled engine for use in the natural-gas-used motor vehicle permits the reduction of the emission quantity of $CO_2$, for example, as compared with a gasoline engine so that a clean exhaust emission characteristic is expectable. As a fuel supply system therefor, there has hitherto been known a system (gas mixer system) based upon a carburetor system for a LPG (Liquefied Pertroleum Gas)-used motor vehicle. Moreover, for further improvement of the exhaust emission characteristic to create a very-low-pollution motor vehicle equivalent to an electric motor vehicle, a high-accuracy air-fuel ratio control superior to the gas mixer system is essential, and from this point of view, for instance, the development of a natural-gas-used motor vehicle with an injection system providing less air-fuel ratio fluctuation and excellent in response characteristic has been in progress.

As well as such a natural-gas-fueled engine, a gasoline engine or the like is also desired to accomplish a clean exhaust emission, and therefore, in addition to the aforesaid high-accuracy air-fuel ratio control, a gas sensor for the control is required to more quickly operate after the engine start. FIG. 58 is an illustration of an activation time of a sensor device and an exhaust emission in a traveling pattern in the case of an example of $NO_x$ emission quantity. From this illustration, it is found that shortening the activation time of the sensor device causes the exhaust emission to be significantly improvable.

The air-fuel ratio is under the feedback control based upon the output of an $O_2$ sensor installed in an exhaust pipe of an engine. For this reason, the promotion of the air-fuel ratio control accuracy significantly relies upon the enhancement of the detection accuracy of the $O_2$ sensor. However, if an $O_2$ sensor for a gasoline engine is used directly for detecting the air-fuel ratio in a natural-gas-fueled engine, a slippage or discrepancy occurs in the output characteristic of the $O_2$ sensor. This is because a natural gas contains methane as a principal component and the H/C ratio larger than that of a gasoline increases the quantity of hydrogen ($H_2$) of an exhaust gas. This phenomenon takes place remarkably in an injection system.

That is, as compared with the gas mixer system which evenly mixes gases in an upstream portion of an intake passage and introduces it into a combustion chamber, the injection system made to directly inject a gas to the vicinity of a combustion chamber of the engine in order to ensure the response characteristic in the fuel control tends to create lack of uniformity of the mixture within the combustion chamber. Whereupon, a large amount of $H_2$ develops in an area where the air-fuel ratio is on the rich side within the combustion chamber, and the $H_2$ concentration of an exhaust gas becomes higher as compared with the gas mixer system, which adds to the slippage or deviation of the sensor output. For this reason, in the case of the $O_2$ sensor for a natural-gas-fueled engine, the elimination of the influence of $H_2$ on the sensor output leading to the slippage of the sensor output is inevitable for a high air-fuel ratio control accuracy.

In addition, the $O_2$ sensor or an air-fuel ratio sensor for detecting an air-fuel ratio over a wider area uses a detecting device made of an oxygen ion conductive solid electrolyte. This device does not work until its temperature rises to some extent. For example, the temperature is approximately 300° C. in the case of the $O_2$ sensor, whereas approximately 700° C. in the case of the air-fuel ratio sensor. That is, an important factor to operate the sensor more quickly is raising the device temperature more quickly, and particularly, a great problem lies in the case of the air-fuel ratio sensor requiring a high activation temperature.

Moreover, a natural-gas-fueled engine creates a problem in that, since a point where an electromotive force of an $O_2$ sensor (rich/lean sensor) rapidly varies shifts into a leaner zone with respect to a stoichiometric value (theoretical air-fuel ratio), the air-fuel ratio (A/F) goes into a lean condition to be output of a window of a three-way catalytic converter, thereby increasing the emission of $NO_x$.

SUMMARY OF THE INVENTION

It is therefore an object of the present invention to provide an air-fuel ratio control system for a gas-fueled engine which is capable of achieving the combustion in the target air-fuel ratio to certainly purify exhaust gases through the use of an exhaust emission purifying catalyst.

Another object of this invention is to provide an gas sensor which is capable of preventing the sensor output slippage caused by $H_2$ of an exhaust gas to greatly enhance the detection accuracy, thus allowing a high-accuracy air-fuel ratio control to improve the exhaust emission even if a large amount of $H_2$ exists in an exhaust gas, for example, like a natural-gas-fueled engine with an injection system does.

A further object of this invention is to provide a gas sensor whose temperature rises quickly so that the sensor operates more quickly.

As exemplified by "SAE 872165" or "Internal Combustion Engine" Vol. 28 No. 12, $H_2$ of the exhaust emitted from a natural-gas-fueled engine reaches approximately twice that of a gasoline engine. Thus, the present inventors consider that the reason why the air-fuel ratio is on a lean side is that, since $H_2$ of the exhaust gas shows a higher diffusion velocity or rate than that of $O_2$, its component concentration differs from the component concentration of the actual exhaust gas on a reactive interface of a sensor.

Accordingly, in accordance with an aspect of the present invention, an air-fuel ratio control system for gas-fueled engine is equipped with a hydrogen invasion preventing means for preventing the invasion of hydrogen of an exhaust gas to a surface of an exhaust gas side electrode of an air-fuel ratio sensor.

This hydrogen invasion preventing means prevents the invasion of hydrogen to the surface of the exhaust gas side electrode to remove $H_2$, causing a sensor output slippage or discrepancy, from a reactive interface (exhaust gas side electrode surface) of the sensor, so that the sensor output slippage is preventable and a suitable air-fuel ratio control is feasible.

Another aspect of an air-fuel ratio control system for a gas fueled engine according to this invention is that an exhaust gas side electrode of an air-fuel ratio sensor is coated with a catalyst layer which removes hydrogen through a catalytic reaction.

Coating the exhaust gas side electrode of the air-fuel ratio sensor with the catalyst layer can eliminate the problem of $H_2$ owing to the catalytic reaction, which removes $H_2$, causing a sensor output slippage, from a reactive interface (exhaust gas side electrode surface) of the sensor, so that the sensor output slippage is preventable to ensure an adequate air-fuel ratio control.

A further aspect of an air-fuel ratio control system for a gas fueled engine according to this invention is that an air-fuel ratio sensor is equipped with a heater to maintain that the temperature of the exhaust gas side electrode surface is above 600° C.

By keeping the temperature of the exhaust gas side electrode surface by the heater to be above 600° C., $H_2$ spontaneously burns to be removable therefrom, so that $H_2$, causing a sensor output slippage, disappears from a reactive interface (exhaust gas side electrode surface) of the sensor. In consequence, the sensor output slippage is preventable to ensure an appropriate air-fuel ratio control.

A further aspect of an air-fuel ratio control system for a gas fueled engine according to this invention is the equipment of a correction means for correcting the air-fuel ratio measured by an air-fuel ratio sensor to the rich side.

Thus, even if the air-fuel ratio sensor shifts to the lean side, the target air-fuel ratio controlled value based upon the air-fuel ratio sensor is set to the rich side in consideration of the shift quantity, thus allowing the optimum air-fuel control.

Furthermore, in accordance with an aspect of this invention, a gas sensor for detecting a specific gas component contained in an exhaust gas from a natural-gas-fueled engine is constructed such that a first electrode exposed to an exhaust gas and a second electrode exposed to a reference oxygen concentration gas are placed on surfaces of an oxygen ion conductive solid electrolyte and a surface of the first electrode is covered with a porous film, wherein a catalyst layer serving an oxidative effect or action is formed on a surface of the porous film and the rate of the carried or held quantity of a catalyst to the total weight of the catalyst layer is set to 0.5 to 2% by weight (wt %).

The hydrogen ($H_2$) contained in large quantities in an exhaust gas from an natural-gas-fueled engine assumes a low molecular weight, and the diffusion velocity of the hydrogen reaches approximately four times that of oxygen ($O_2$), and therefore, it can be considered that the high velocity at which the hydrogen passes through the porous film to arrive at the surface of the first electrode causes the aforesaid output slippage. On the other hand, in the structure according to this invention, the catalyst layer is placed on the surface of the porous film, so that $H_2$ is oxidized in this catalyst layer to produce stable $H_2O$. Thus, the influence of $H_2$ on the sensor output is eliminable, and particularly, since the catalyst carried quantity is set to be in the aforesaid range, the output slippage prevention is compatible with the response characteristic.

It is also appropriate that the rate of the catalyst carried quantity to the total weight of the catalyst layer is increased to be 2 to 5% by weight. In this case, the porosity of the aforesaid porous film is set to 10 to 20% greater than normal. Although increasing the catalyst carried quantity tends to deteriorate the sensor response characteristic, the method of increasing the porosity of the porous film to 10 to 20% within the range which does not impair the durability can improve the response characteristic. Accordingly, in this case, even if the catalyst carried quantity is raised to 2 to 5% by weight, a response characteristic equivalent to the case of 0.5 to 2% by weight is obtainable, and the catalytic action continues for a long term.

In more detail, it is possible to provide a structure in which the aforesaid first electrode is placed on one surface of the oxygen ion conductive solid electrolyte while the aforesaid second electrode is put on the other surface thereof. Further, the catalyst layer is made such that a porous ceramic carries a catalytic metal. Still further, it is also appropriate that a heater member is provided to heat the catalyst layer, which quickly raises the temperature of the catalyst to an active temperature.

Moreover, it is also appropriate that a porous layer whose porosity is higher than that of the catalyst layer is provided as a trap layer on a surface of the catalyst layer, which prevents the deposit components developed by the combustion of an engine oil or the like from coming in the catalyst layer or a further inside. In addition, the flying of the catalytic metal, the peeling-off of the catalyst layer and others are preventable, because the exhaust gas does not directly run into the catalyst layer. Concretely, it is preferable that the porosity of the trap layer is set to be 40 to 60%, and it is also possible that the trap layer comprises a plurality of layers different in porosity.

Each of the gas sensors thus constructed uses the porous film as a protective coat for the first electrode, and constitutes an oxygen sensor which detects the electromotive force generated between the first electrode and the second electrode. Further, these gas sensors are particularly effective in the case that the natural-gas-fueled engine is equipped with a fuel supplying system of an injection system, and display a great effect for the elimination of the sensor output slippage.

A further aspect of this invention is that a gas sensor is constructed such that a first electrode exposed to an exhaust gas from an internal combustion engine and a second electrode exposed to a reference oxygen concentration gas are placed on surfaces of an oxygen ion conductive solid electrolyte, and a diffusion resistance layer made from a porous film is provided to cover a surface of the first electrode so that an air-fuel ratio is sensed on the basis of a limiting current flowing between the first and second electrodes in response to an application of a given voltage thereto, and further a catalyst layer exerting an oxidizing action or effect is formed on a surface of the diffusion resistance layer.

In the gas sensor to be used as a wide-area air-fuel ratio sensor, since the catalyst layer is formed on the surface of the diffusion resistance layer, the oxidizing action of the catalyst eliminates the influence of $H_2$ or the like of the exhaust gas to suppress the sensor output slippage. In addition, although the limiting current type air-fuel ratio sensor generally needs a high minimum operating temperature and takes time before its operation as compared with the $O_2$ sensor, since in the aforesaid structure the catalyst layer exerting the oxidizing action is integrally placed on the device surface, the heat generated through the catalytic reaction assists the temperature rise of the device, thus allowing the quicker operation of the sensor.

Still further, in accordance with an aspect of this invention, a gas sensor for a natural-gas-fueled engine is constructed such that a first electrode exposed to an exhaust gas and a second electrode exposed to a reference oxygen concentration gas are placed on surfaces of an oxygen ion conductive solid electrolyte and a surface of the first electrode is covered with a coating layer, wherein the coating layer is made by a porous film whose average pore diameter is above 1000 angstroms (Å).

As mentioned before, a large amount of hydrogen ($H_2$) with a low molecular weight exists in an exhaust gas from a natural-gas-fueled engine, and there is a difference between the velocity of diffusion of $H_2$ in the coating layer and the velocity of diffusion of oxygen ($O_2$) therein, which may cause the sensor output slippage. According to this aspect, the coating layer is made so that the average pore diameter is 1000 Å, which can facilitate the diffusion of $O_2$ higher in molecular weight than $H_2$, with the result that the difference between both the diffusion velocities becomes sufficiently small. Accordingly, the output slippage is preventable through the elimination of the influence of $H_2$ on the sensor output, and therefore, when this gas sensor is used for a natural-gas-fueled engine with an injection system, high-accuracy air-fuel ratio control becomes feasible, which contributes greatly to the improvement of the exhaust emission.

More preferably, the coating layer is constructed with a film in which more than 90% of all the pores have a diameter exceeding 1000 Å. When the rate of the pores with a diameter exceeding 1000 Å increases, the diffusion velocity difference between $H_2$ and $O_2$ becomes substantially zero, which further enhances the aforesaid output slippage preventing effect.

More specifically, the first electrode is provided on one surface of the oxygen ion conductive solid electrolyte while the second electrode is provided on the other surface thereof. For instance, the gas sensor structure can be made such that the oxygen ion conductive solid electrolyte is shaped into a test-tube-like configuration and the first electrode is placed on the inner circumferential surface of the oxygen ion conductive solid electrolyte while the second electrode is placed on the outer circumferential surface thereof, or made such that the oxygen ion conductive solid electrolyte is shaped into a flat-plate-like configuration and the first electrode is located on the front surface of the oxygen ion conductive solid electrolyte while the second electrode is located on the rear surface thereof.

It is also appropriate that a porous film whose porosity is 40 to 60 vol % is provided as a trap layer outside the coating layer. In this case, it is possible to prevent the deposit component developing due to the combustion of the engine oil or the like from invading into the coating layer to cause the closing of pores.

Moreover, it is also possible that a heating device is provided to heat the sensor. This can burn the deposit component developing due to the combustion of the engine oil or the like within the coating layer, thereby preventing the closing of the pores of the coating layer. In addition, this activates the sensor at an early stage to prevent the deterioration of the exhaust emission.

Besides, it is also possible that a catalyst layer exerting an oxidizing action is formed on a surface of the coating layer. This catalyst layer oxidizes $H_2$ in an exhaust gas to reduce $H_2$ which arrives at the coating layer, thereby surely suppressing the sensor output slippage caused by $H_2$.

A still further aspect of this invention is that a gas sensor comprises a pump cell having a pair of pump electrodes, a sensor cell having a pair of sensor electrodes, a chamber in which at least two surfaces are covered with both the cells, at least one communication hole for introducing an exhaust gas from an internal combustion engine into the chamber, and a diffusion resistance layer constructed with a porous film and placed on an exhaust gas side of the communication hole and in an interior of the communication hole or on both so that an air-fuel ratio is detected on the basis of a pumping current flowing in the pump cell when a voltage is applied to the pump cell to cause a sensing current occurring between the pair of electrodes of the sensor cell to assume a given or predetermined value, and further comprises a catalyst layer exerting an oxidizing action and formed on an exhaust gas side surface of the diffusion resistance layer.

Likewise, the air-fuel ratio sensor with this structure can suppress the sensor output slippage owing to the effect of the catalyst layer formed on the surface of the diffusion resistance layer, and further, can effectively achieve the temperature rise of the device through the use of the heat generated in the catalyst layer. Thus, the sensor operates more quickly.

A still further aspect of this invention is that a gas sensor comprises a pump cell having a pair of pump electrodes, a sensor cell having a pair of sensor electrodes, a chamber in which at least two surfaces are covered with both the cells, and at least one pin hole exerting a diffusion resistance action and made for introducing an exhaust gas from an internal combustion engine into the chamber so that an air-fuel ratio is detected on the basis of a pumping current flowing in the pump cell when a voltage is applied to the pump cell to cause a sensing current occurring between the pair of electrodes of the sensor cell to assume a given value, and further comprises a catalyst layer exerting an oxidizing action and formed to cover an exhaust gas side of the pin hole.

It is also acceptable that the pin hole taking a diffusion resistance action is provided in place of the diffusion resistance layer. Even the air-fuel ratio sensor with this structure can suppress the sensor output slippage owing to the action of the catalyst layer formed to cover the pin hole, and can operate quickly owing to the heat generated in the catalyst layer.

A still further aspect of this invention is that a gas sensor comprises a pump cell having a pair of pump electrodes, a sensor cell having a pair of sensor electrodes, a chamber in which at least two surfaces are covered with both the cells, and at least one diffusion resistance means for introducing an exhaust gas from an internal combustion engine into the chamber so that an air-fuel ratio is detected on the basis of a pumping current flowing in the pump cell when a voltage is applied to the pump cell to cause a sensing current occurring between the pair of electrodes of the sensor cell to assume a given value, and further comprises a catalyst layer exerting an oxidizing action and formed between a chamber side end portion of the diffusion resistance means and the sensor electrodes exposed to the interior of the chamber.

In the air-fuel ratio sensor with the structure in which an exhaust gas is introduced through the diffusion resistance means comprising the diffusion resistance layer or the pin hole into the chamber, it is also possible that the catalyst layer is provided on the chamber side. In this case, if the catalyst layer is located between the chamber side end portion of the diffusion resistance means and the sensor electrodes, similar effects are obtainable.

Preferably, in the above-mentioned gas sensors, the catalyst carried quantity in the catalyst layer is set to be 0.5 to 2 wt % with respect to the total weight of the catalyst layer. In this case, for the above-mentioned reason, the sensor output slippage is effectively suppressible and the response characteristics is securable. In addition, in the case that this invention is applied to an internal combustion engine with an injection system based upon a fuel supply system, the sensor output slippage suppressing effect is great, and particularly, if the internal combustion engine is of a natural-gas-fueled type, since the sensor output largely undergoes the influence of $H_2$, this gas sensor can exhibit excellent effects in eliminating the output slippage. Further, with the natural-gas-fueled engine, the temperature of the exhaust gas therefrom is lower as compared with a gasoline engine, which results in a longer time for the sensor activation. In such a case, the catalyst layer significantly displays its temperature rise assisting effect.

BRIEF DESCRIPTION OF THE DRAWINGS

The object and features of the present invention will become more readily apparent from the following detailed description of the preferred embodiments taken in conjunction with the accompanying drawings in which.

Figure 1:
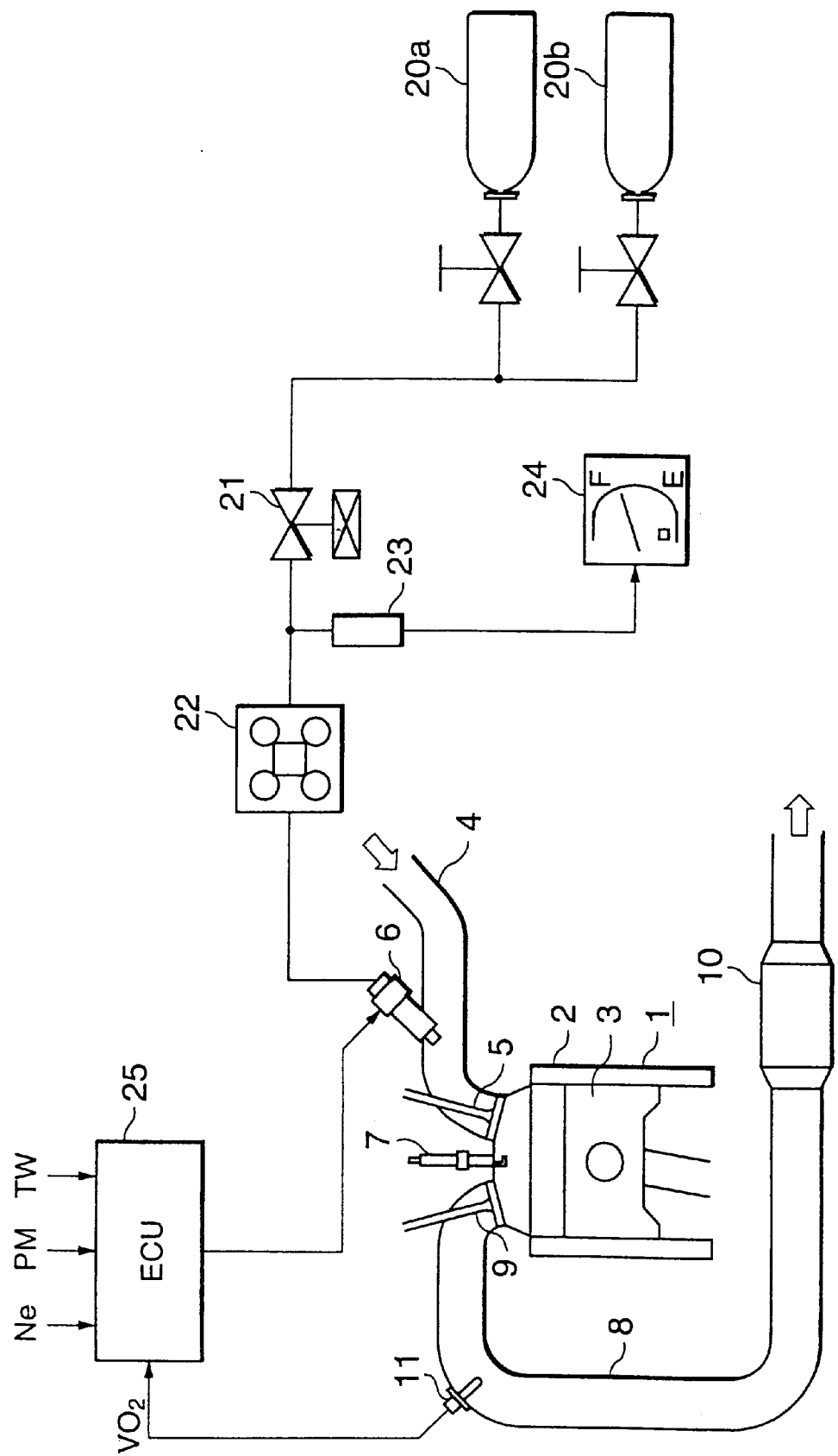
FIG. 1 is an illustration of the entire arrangement of an air-fuel ratio control system for an gas fueled engine according to a first embodiment of the present invention.

DETAILED DESCRIPTION OF THE INVENTION (First Embodiment)

Referring to the drawings, a description will be made hereinbelow of a first embodiment of the present invention.

FIG. 1 is an illustration of the whole arrangement of an air-fuel ratio control system for a gas-fueled engine according to this embodiment.

In this illustration, in an engine 1, a piston 3 is placed within a cylinder 2, and an intake pipe 4 is in communication with the engine 1 and its intake port accommodates an intake valve 5. Further, a gas injector 6 is installed in the intake pipe 4. With this construction, air is sucked through the intake pipe 4 and the intake valve 5 while a fuel containing a natural gas as a principal component is fed from the gas injector 6, so that the air-natural gas mixture is supplied into the cylinder 2 of the engine 1.

In addition, an ignition plug 7 is mounted in the engine 1 to ignite the mixture within the cylinder 2. An exhaust pipe 8 is coupled to the engine to establish an exhaust path, and an exhaust valve 9 is located in its exhaust port. The exhaust gas is discharged through the exhaust valve 9 and the exhaust pipe 8 to the atmosphere side. Further, a three-way catalytic converter (three-way catalyst) 10 serving as an exhaust gas purifying catalyst is provided in the middle of the exhaust pipe 8. Still further, an $O_2$ sensor 11 serving as an air-fuel ratio sensor is situated on the upstream side of the three-way catalytic converter 10 in the exhaust pipe 8.

Figure 2:
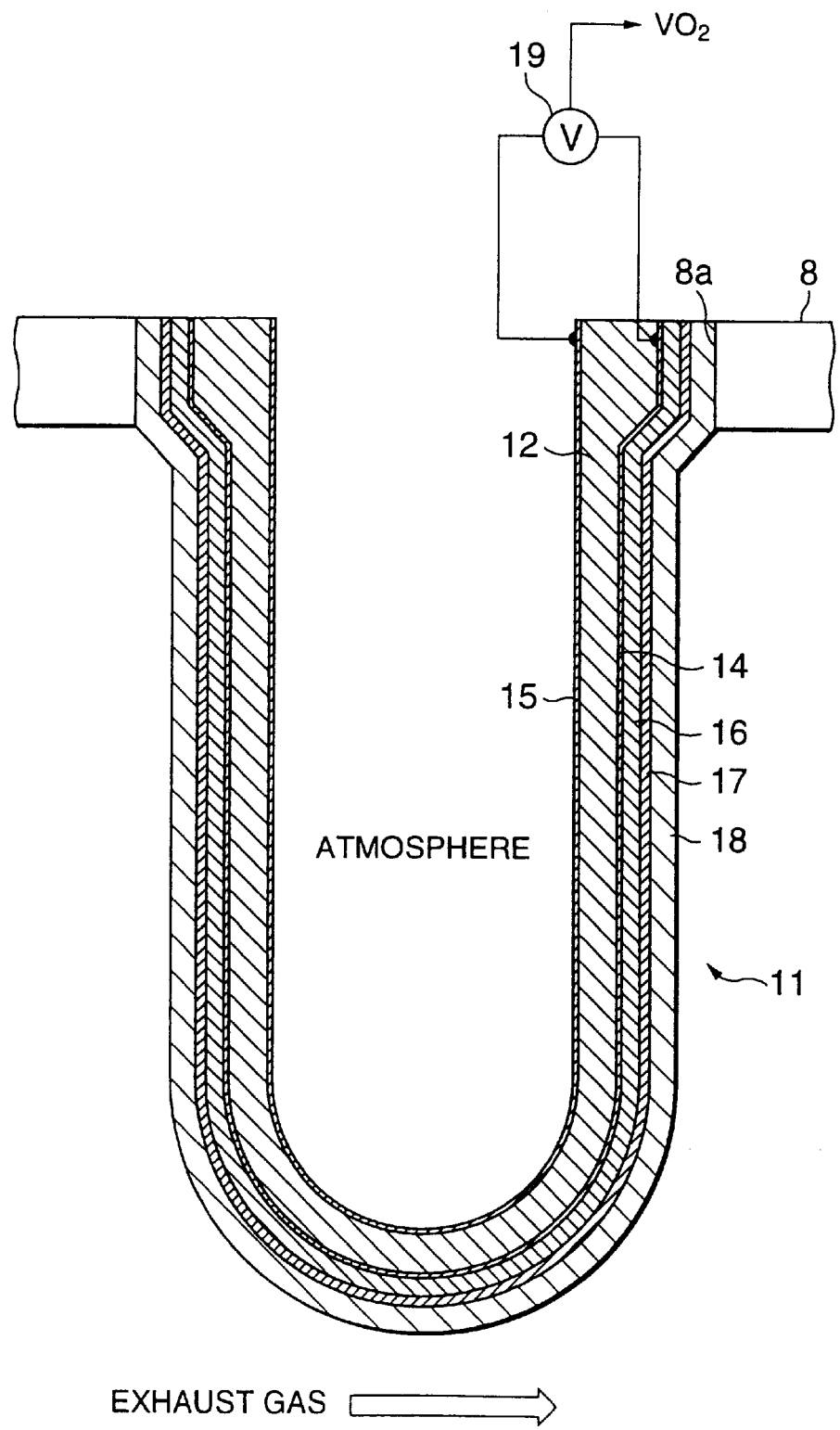
FIG. 2 is a cross-sectional view showing an $O_2$ sensor thereof.

FIG. 2 is a cross-sectional view showing the $O_2$ sensor 11. In FIG. 2, a sensor fitting hole 8a is made in the exhaust pipe 8, and a cap-shaped element 12 made of a solid electrolyte is inserted into this sensor fitting hole 8a. The element 12 is made of zirconia, and has a blind-end cylindrical configuration. An outer circumferential surface of the element (solid electrolyte tube) 12 is coated with a Pt (Platinum)-made outside electrode 14, while an inner circumferential surface of the element 12 is coated with a Pt-made inside electrode 15. Thus, the $O_2$ sensor 11 comprises the element 12 made of a solid electrolyte whose inner surface (one side surface) carries the inside electrode 15 acting as an atmosphere side electrode and whose outer surface (the other side surface) holds the outside electrode 14 serving as an exhaust gas side electrode.

In addition, the outside electrode 14 is covered with a coating film 16 for its protection, and a surface of the coating film 16 is coated with a catalyst layer 17. The catalyst layer 17 is produced by mixing a catalytic metal such as platinum rhodium by 3 to 5 wt % into a material such as alumina. Moreover, the catalyst layer 17 is covered with a protective layer (alumina) 18 for protection thereof.

Between the outside electrode 14 and the inside electrode 15, an electromotive force corresponding to the oxygen concentration of an exhaust gas occurs through the element (solid electrolyte tube) 12, and is measured by an electromotive-force sensor 19. An output of the $O_2$ sensor 11 is shown in (a) of FIG. 3.

Meanwhile, a fuel supply system to the gas injector 6 in FIG. 1 is composed of bombs or cylinders 20a, 20b, a fuel cutoff valve 21 and a regulator 22, with the bombs 20a, 20b hold a natural gas compressed up to approximately 200 atm. The natural gas in these bombs 20a, 20b is delivered through the fuel cutoff valve 21 to the regulator 22 which, in turn, performs a pressure reduction from 200 atm being the internal pressure of the bombs 20a, 20b to 3 to 8 atm before supplying it to the gas injector 6. A pressure sensor 23 senses the gas pressure (bomb internal pressure) between the fuel cutoff valve 21 and the regulator 22, and a fuel meter 24 displays the fuel residual quantity in the bombs 20a, 20b.

Designated at numeral 25 is an electronic control unit (which will be referred hereinafter to as an ECU) based upon a microcomputer. This ECU 25 receives output signals from an engine speed sensor, an intake pressure sensor and a water temperature sensor and detects an engine speed Ne, an intake pressure PM, and engine water temperature Tw and others. In addition, the ECU 25 catches an output signal from the $O_2$ sensor 11 shown in (a) of FIG. 3 to compare it with a reference or comparison voltage Vref, and if the sensor signal does not reach the comparison voltage Vref, determines that the sensor signal is in a L level, while determining a H level if it exceeds the comparison voltage Vref. On the basis of this comparison result, the ECU 25 calculates an air-fuel ratio feedback correction coefficient FAF shown in (b) of FIG. 3, which will be described herein later. Moreover, the ECU 25 drive-controls the gas injector 6 to feedback-control the injection quantity on the basis of the feedback correction coefficient FAF so that the $O_2$ sensor 11 shows a stoichiometric value, thereby making the three-way catalytic converter 10 displaying the highest purification performance.

Secondly, a description will be given hereinbelow of an operation of the gas-fueled engine air-fuel ratio control system thus arranged.

Figure 3:
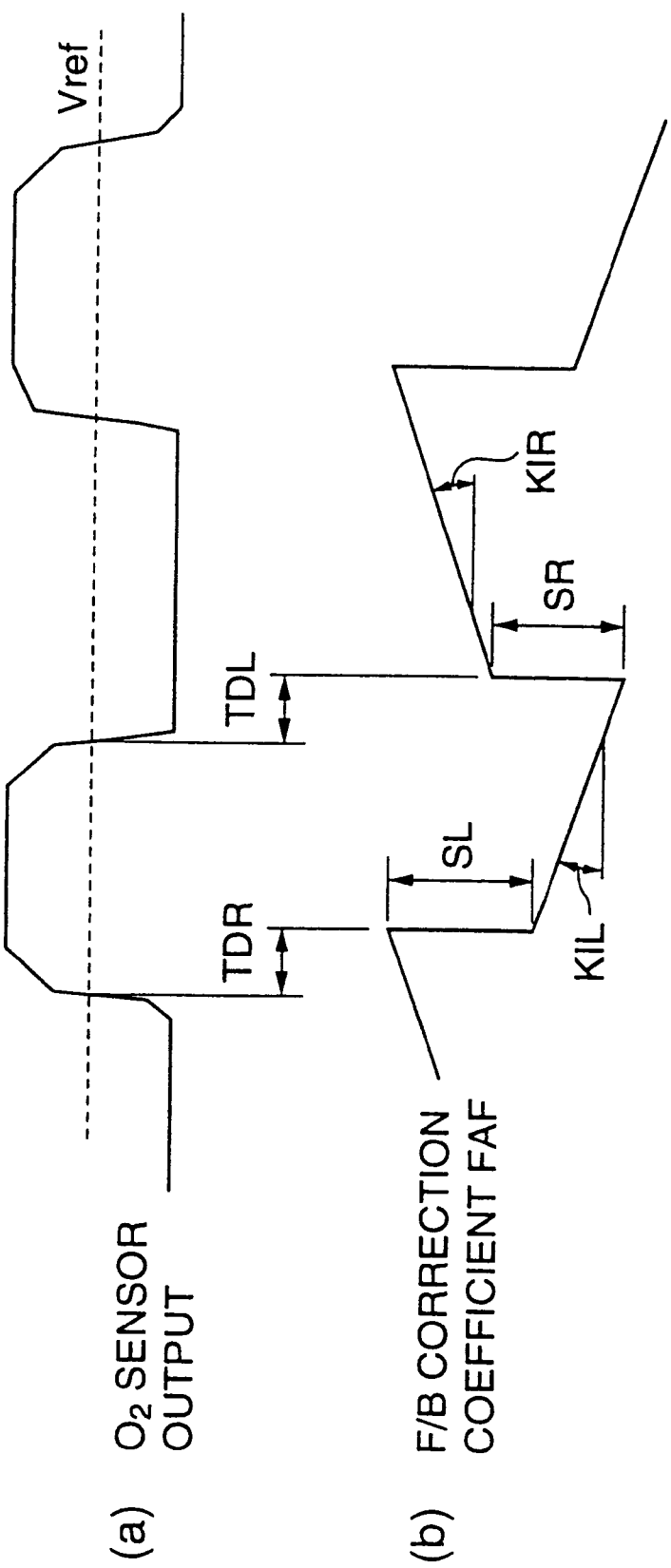
FIG. 3 is an illustration useful for explaining an output signal of the $O_2$ sensor and a FAF.
Figure 4:
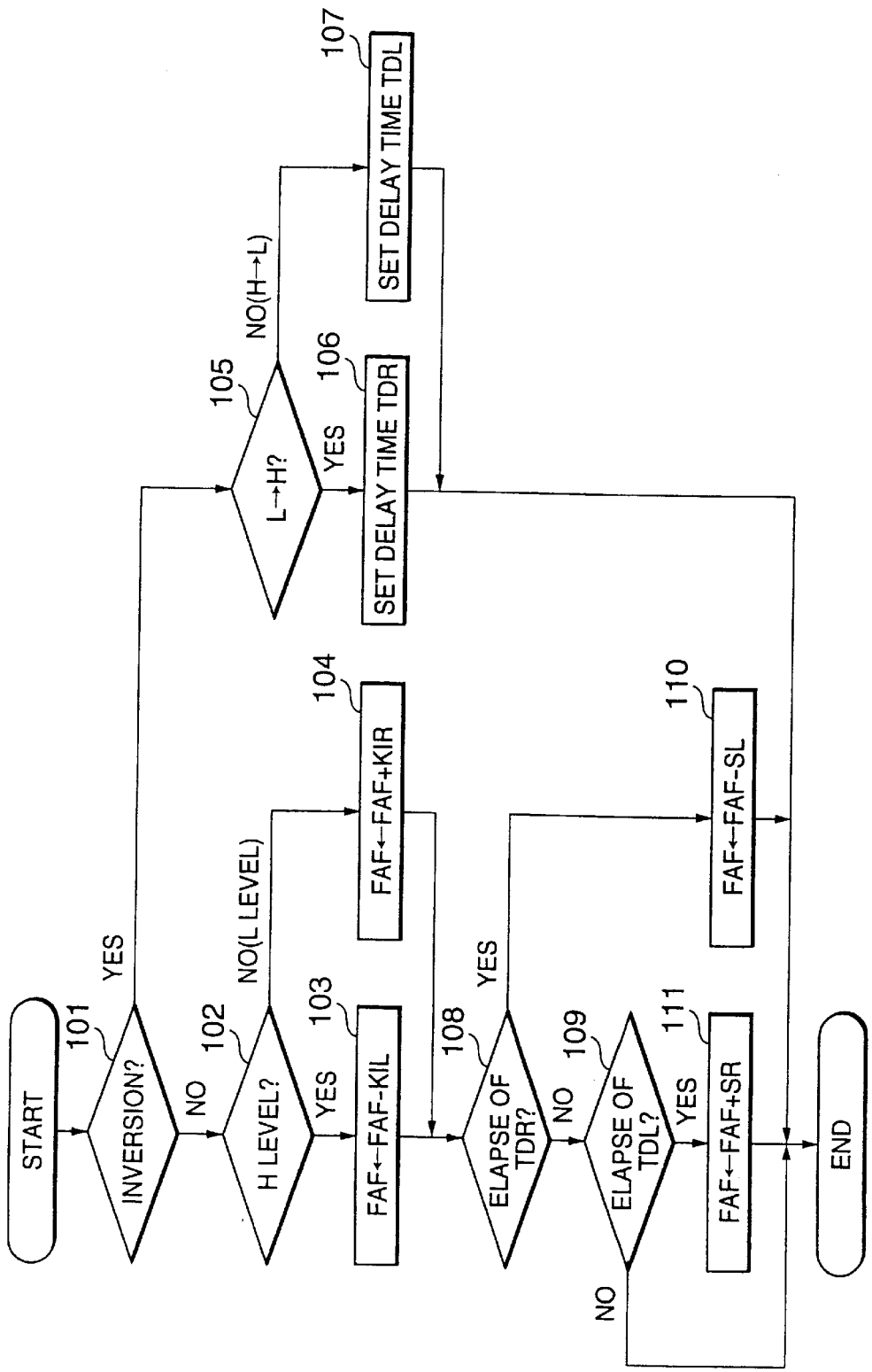
FIG. 4 is a flow chart showing a FAF calculation routine.

FIG. 4 illustrates a calculation routine for a feedback correction coefficient FAF in the ECU 25, that is, shows the calculation routine for the feedback correction coefficient FAF shown in (b) of FIG. 3.

In FIG. 4, the ECU 25 decides, in a step 101, whether or not an inversion occurs because an output signal of the $O_2$ sensor 11 crosses a comparison voltage Vref, and if no occurrence of the inversion, advances to a step 102 to check whether or not the sensor output signal is in the H level state. If being in the H level, the ECU 25 proceeds to a step 103 to subtract a proportional coefficient KIL from the feedback correction coefficient FAF at that time. This processing gradually decreases the feedback correction coefficient FAF with an inclination KIL as shown in (b) of FIG. 3. On the other hand, when the output signal of the $O_2$ sensor 11 is in the L level state in the step 102, the ECU 25 goes to a step 104 to add a proportional coefficient KIR to the feedback correction coefficient FAF at that time. This processing gradually increases the feedback correction coefficient FAF with an inclination KIR as shown in (b) of FIG. 3.

Furthermore, if the decision of the step 101 shows the occurrence of the inversion resulting from the fact that the output signal of the $O_2$ sensor 11 crosses the comparison voltage Vref, the ECU 25 advances to a step 105 to check whether it is an inversion from the L level to the H level or an inversion from the H level to the L level. If the inversion is from the L level to the H level, the ECU 25 sets a delay time TDR in a step 106. On the other hand, if the inversion is from the H level to the L level, the ECU 25 sets a delay time TDL in a step 107.

Still further, in steps 108 and 109, the ECU 25 decides whether the delay times TDR and TDL elapse, and when the delay time TDR elapses from the instance of the inversion, proceeds to a step 110 to subtract a skip quantity SL from the feedback correction coefficient FAF at that time. On the other hand, when the delay time TDL elapses from that inversion, the ECU 25 goes to a step 111 to add a skip quantity SR to the feedback correction coefficient FAF at that time. With this processing (the addition/subtraction of the given quantity SL/SR), the feedback correction coefficient FAF greatly varies (skips) as shown in (b) of FIG. 3.

As described above, when the comparison result between the output signal of the $O_2$ sensor 11 and the reference level Vref goes into an inversion, the ECU 25 conducts the addition or subtraction of the given value SR or SL to/from the feedback correction coefficient FAF, and if no inversion, gradually increases or decreases the feedback correction coefficient FAF. A fuel quantity is calculated as follows on the basis of this feedback correction coefficient FAF.

Figure 5:
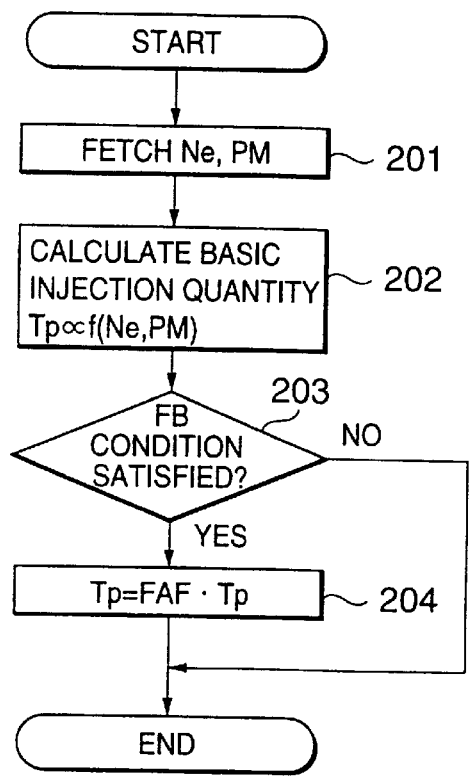
FIG. 5 is a flow chart showing an air-fuel ratio control routine.

FIG. 5 shows a fuel injection control routine in the ECU 25.

In FIG. 5, in a step 201 the ECU 25 takes in an engine speed Ne and an intake pressure PM and, in a step 202, calculates a basic injection quantity Tp corresponding to the engine speed Ne and the intake pressure PM through the use of a map prepared in advance. Further, in a step 203 the ECU 25 decides whether or not to satisfy an air-fuel ratio feedback control condition (that the temperature Tw is above a given or predetermined value), and if satisfying that condition, in a step 204 the ECU 25 multiplies the feedback correction coefficient FAF by the basic injection quantity Tp, thus calculating a final injection quantity. The gas injector 6 is driven under control to produce the final injection quantity.

As seen from the above description, the ECU 25 acting as an air-fuel ratio control means controls the fuel supply quantity through the gas injector 6 in order to reduce the deviation between the air-fuel ratio based on the $O_2$ sensor 11 and the target air-fuel ratio.

Moreover, a description will be made hereinbelow of the difference between the installation of the catalyst layer 17 in the air-fuel ratio sensor and no installation of the catalyst layer 17 therein.

Figure 6:
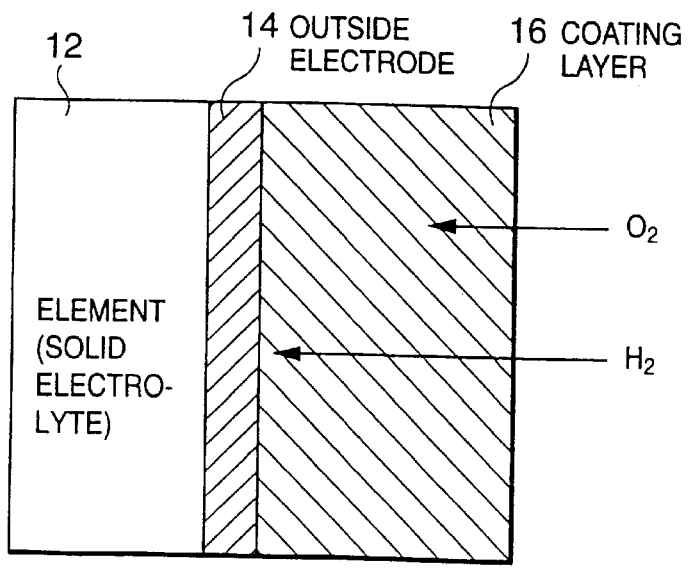
FIG. 6 illustratively shows an $O_2$ sensor with no catalyst layer.
Figure 7:
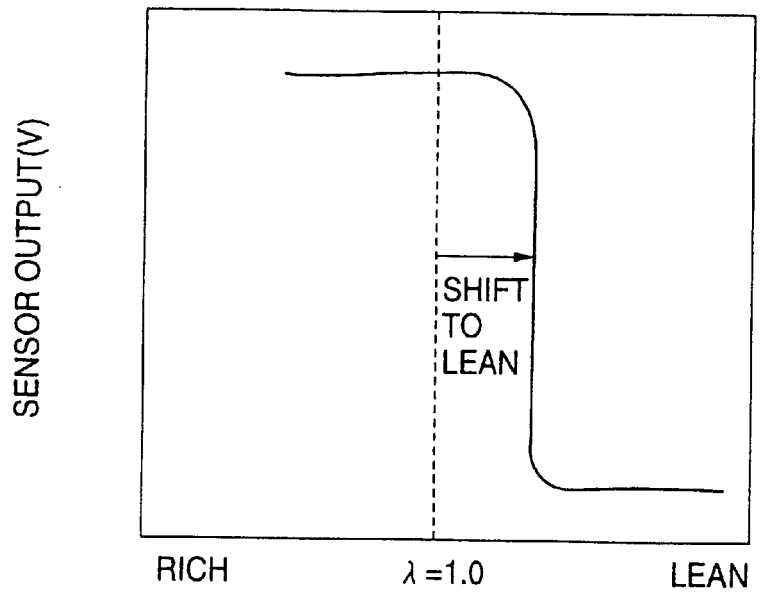
FIG. 7 is an illustration of a sensor output characteristic in the case of using an $O_2$ sensor with no catalyst layer.

Referring to FIGS. 6 and 7, a description will be made hereinbelow of an occurrence mechanism of a sensor output slippage or deviation taking place with no installation of the catalyst layer 17. In FIG. 6, in the case of no addition of the catalyst layer 17, $O_2$ and $H_2$ pass through the coating layer 16 to produce an oxidation reaction on the Pt-made outside electrode 14. At this time, since $H_2$ higher in diffusion velocity than $O_2$ more diffuses, even if the exhaust gas component is at a stoichiometric value, an $H_2$ rich condition exists in the vicinity of its electrode, so that, not until the exhaust gas component turns to a lean condition that the output of the $O_2$ sensor 11 does rapidly vary. For this reason, as shown in FIG. 7, the relationship between an excess air factor λ and an sensor output shifts to the lean side.

Figure 8:
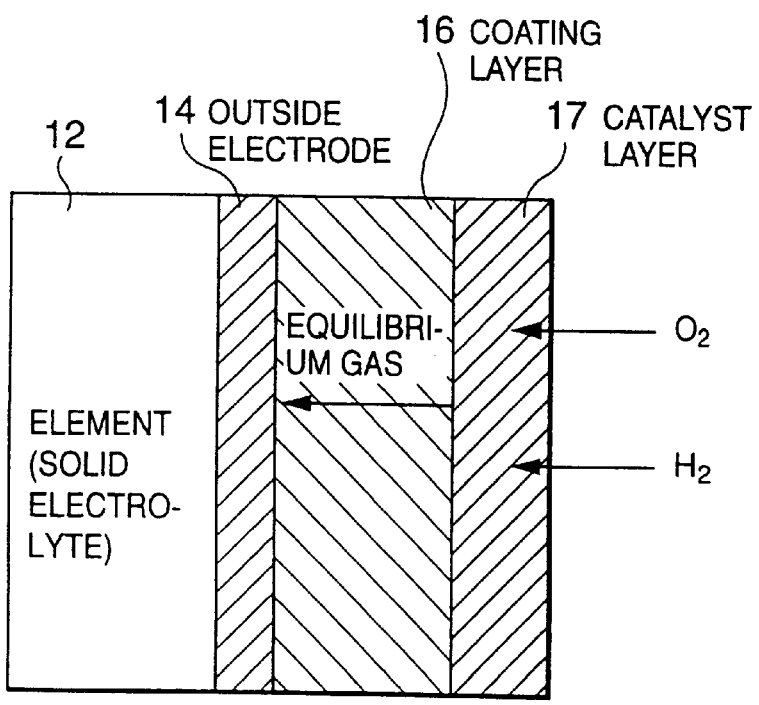
FIG. 8 illustratively shows an $O_2$ sensor with a catalyst layer.
Figure 9:
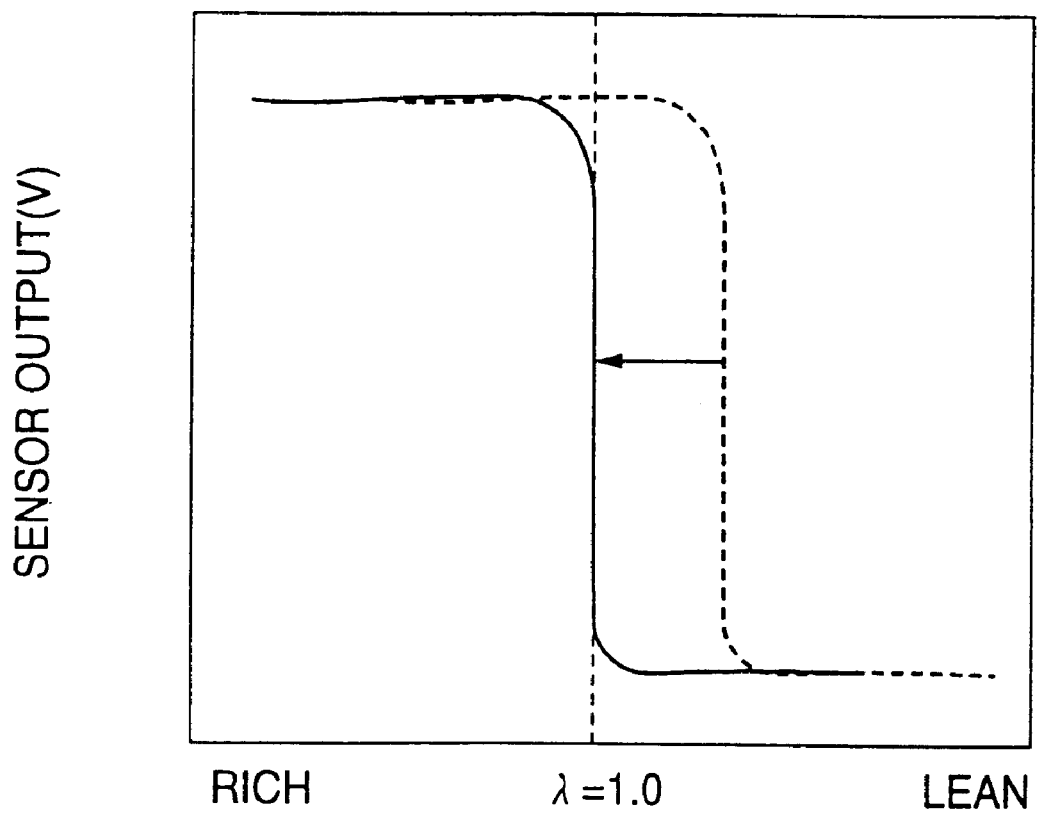
FIG. 9 is an illustration of a sensor output characteristic in the case of employing an $O_2$ sensor with a catalyst layer.

Contrary to this, in the case of the addition of the catalyst layer 17 as shown in FIG. 8, $O_2$ and $H_2$ react and then arrive at the Pt-made outside electrode 14 in the form of an equilibrium gas (after-reaction gas; $H_2O$ gas), and hence, as indicated by a solid line in FIG. 9, the shift of the sensor output is suppressible.

Figure 26:
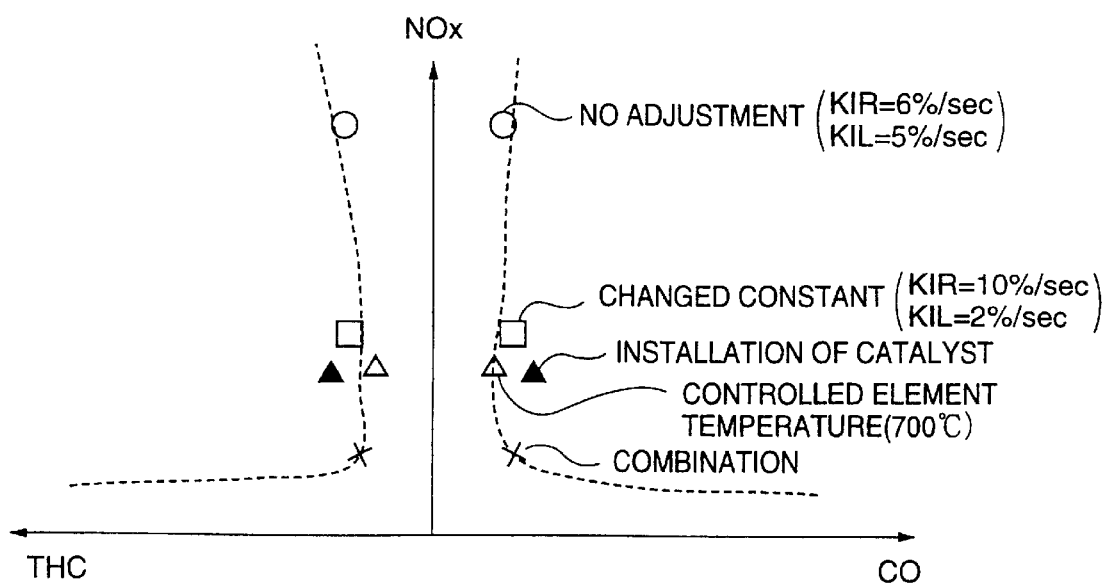
FIG. 26 is an illustration of a measurement result of LA mode emission.

FIG. 26 shows the quantities of HC, CO and $NO_x$ of an exhaust gas after it passes through the three-way catalytic converter 10, where "circles" signify a case of no installation of the catalyst layer 17 while shadowed "triangles" represent a case of the installation of the catalyst layer 17. As found from this illustration, the installation of the catalyst layer 17 can reduce all HC, CO and $NO_x$ and can suppress the emission quantity after the three-way catalyst.

The features of this embodiment are as follows.

That is, the outside electrode 14 of the $O_2$ sensor is coated with the catalyst layer 17 for removing hydrogen through its catalytic reaction. Thus, since the catalyst is carried by the exhaust gas side surface of the outside electrode 14, $H_2$ is removable through the catalytic reaction. That is, the catalyst layer 17 functions as a hydrogen invasion preventing means for preventing the invasion of hydrogen of the exhaust gas to the surface of the outside electrode 14 of the $O_2$ sensor. With this structure, $H_2$ causing the sensor output slippage is removable from the reactive interface (the surface of the outside electrode). In consequence, the sensor output slippage is preventable to assure an appropriate air-fuel ratio control.

(Second Embodiment)

A description of a second embodiment which will be made hereinbelow focuses on the difference from the first embodiment.

Figure 10:
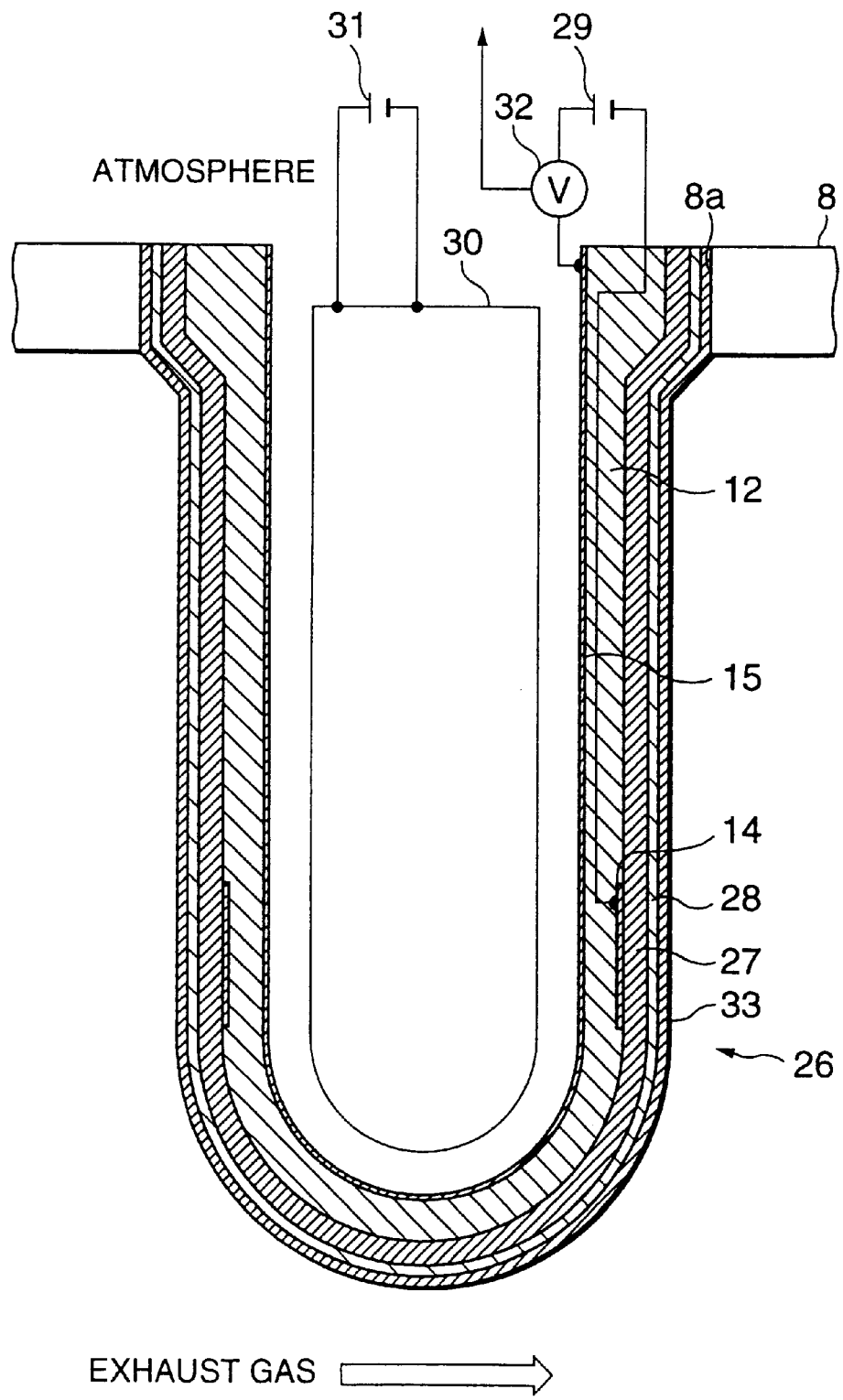
FIG. 10 is a cross-sectional view showing a wide-area air-fuel ratio sensor of an air-fuel ratio control system according to a second embodiment of this invention.

In this embodiment, in place of the rich/lean sensor ($O_2$ sensor) 11, there is used a wide-area air-fuel ratio sensor (linear sensor) 26 shown in FIG. 10. In addition, a portion outside an outside electrode 14 of an element (solid electrolyte tube) 12 is coated with a catalyst layer 28 which can remove hydrogen through its catalytic reaction.

More specifically, the wide-area air-fuel ratio sensor has basically the same structure as that of the $O_2$ sensor shown in FIG. 2, except that a coating film 27 which can velocity-control the diffusion of a gas is provided instead of the coating layer 16 in FIG. 2. The coating film 27 is coated with a catalyst layer 28. In addition, a surface of the catalyst layer 28 is covered with a protective layer (alumina) 33. Moreover, a power supply 29 is connected between the electrode 14 and another electrode 15, and an alumina heater 30 is placed within the element (solid electrolyte tube) 12. The alumina heater 30 heats the element (solid electrolyte tube) 12 using a power from a power supply 31. Further, a current sensor 32 is provided to detect a current flowing between the electrodes 14, 15.

The principle of a wide-area air-fuel ratio sensor will be described hereinbelow with reference to FIGS. 11 to 13.

Figure 11:
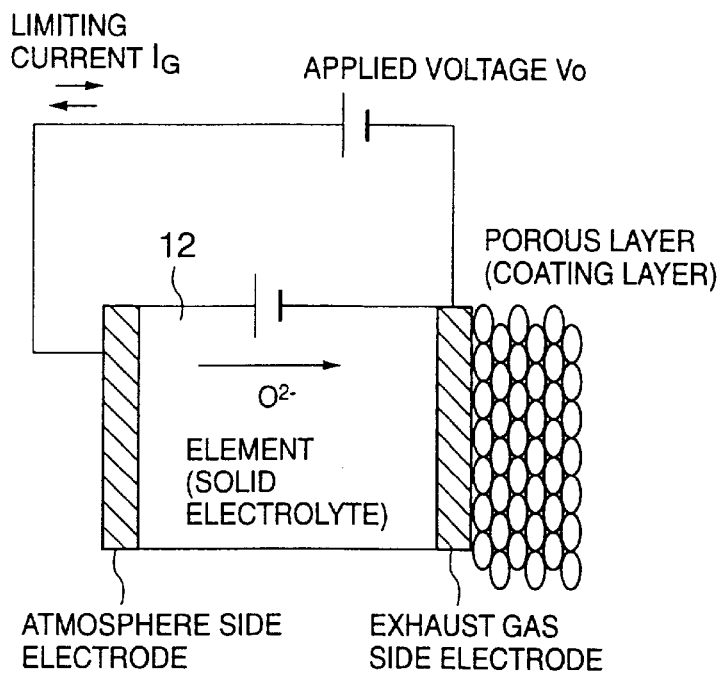
FIG. 11 illustratively shows the principle of a wide-area air-fuel ratio sensor.
Figure 12:
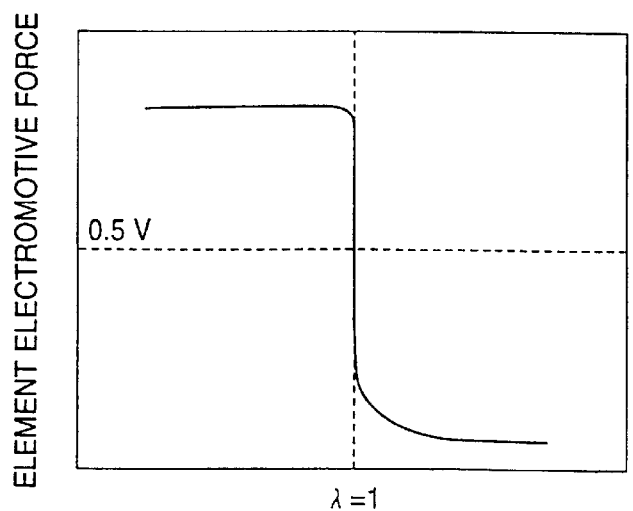
FIG. 12 is an illustration of an output characteristic of a wide-area air-fuel ratio sensor.

An electromotive force of 0.5 volts developed at λ=1 as shown in FIG. 12 is applied to a zirconia element (solid electrolyte tube) 12 in a direction opposite to the electromotive force as shown in FIG. 11, thereby detecting an air-fuel ratio by an inter-electrode current $I_G$.

Figure 13A:
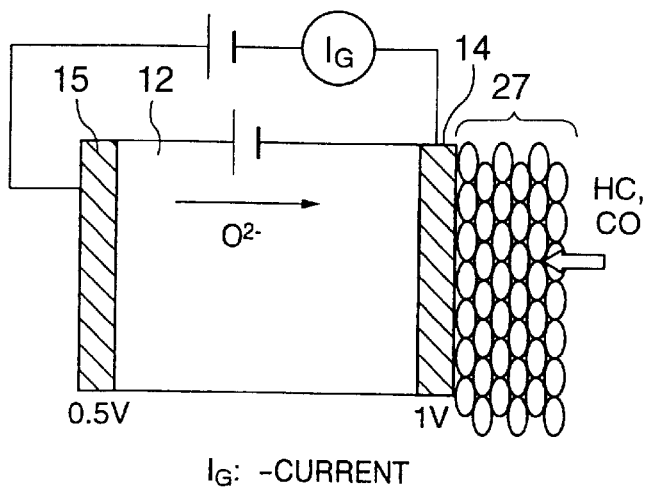
FIGS. 13A to 13C illustratively show the principle of a wide-area air-fuel ratio sensor.
Figure 13B:
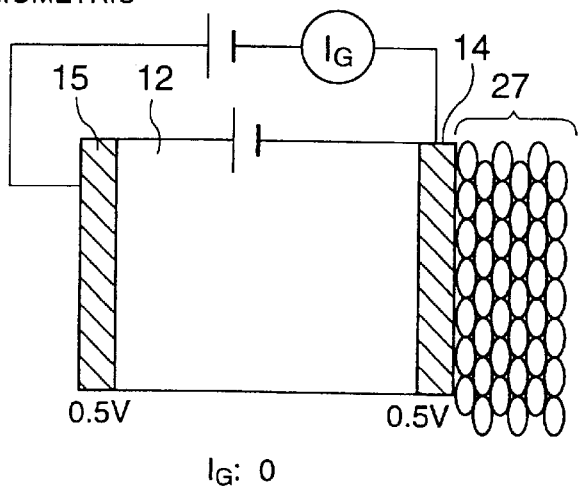
Figure 13C:
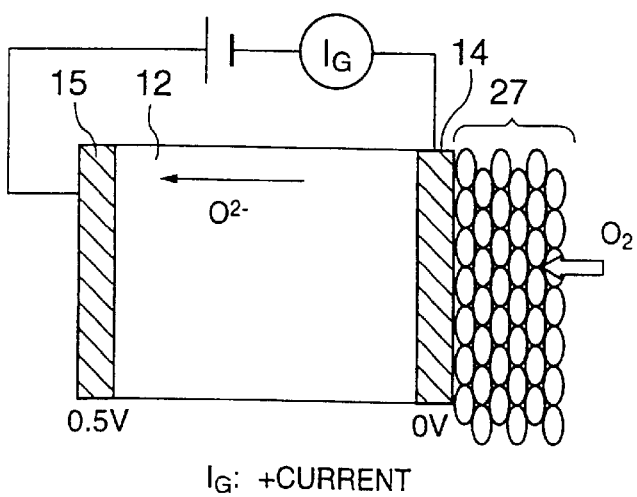

At a stoichiometric value, as shown in FIG. 13B, the electromotive force of the element 12 matches the applied voltage, so that the current $I_G$ assumes "0". At a lean, as shown in FIG. 13C, the electromotive force of the element 12 is zero volt, with the result that $O^{2-}$ moves from the outside electrode 14 to the inside electrode 15 due to the applied voltage to produce a plus current as the current $I_G$. Further, at a rich, as shown in FIG. 13A, since the electromotive force of the element 12 comes to 1 volt, $O_2$ moves from the inside electrode 15 to the outside electrode 14 due to the difference from the applied voltage, thereby developing a minus current as the current $I_G$. The current $I_G$ flowing at this time, at a lean, depends upon the quantity of $O_2$ passing through the coating film (porous layer) 27 while, at a rich, depending upon the quantities of HC and CO passing through the coating film (porous layer) 27, and hence, if $H_2$ of an exhaust gas increases like an natural-gas-fueled engine, the current value varies even at the same air-fuel ratio.

Figure 14:
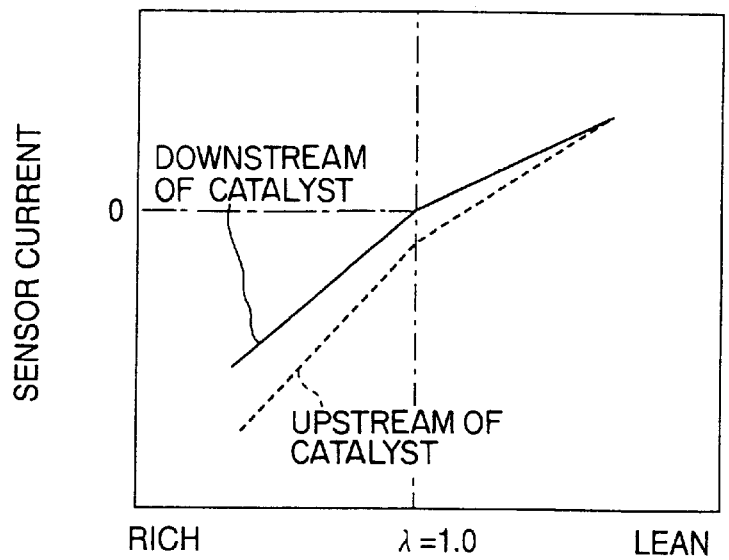
FIG. 14 is an illustration of an output characteristic of a wide-area air-fuel ratio sensor with no catalyst layer.
Figure 15:
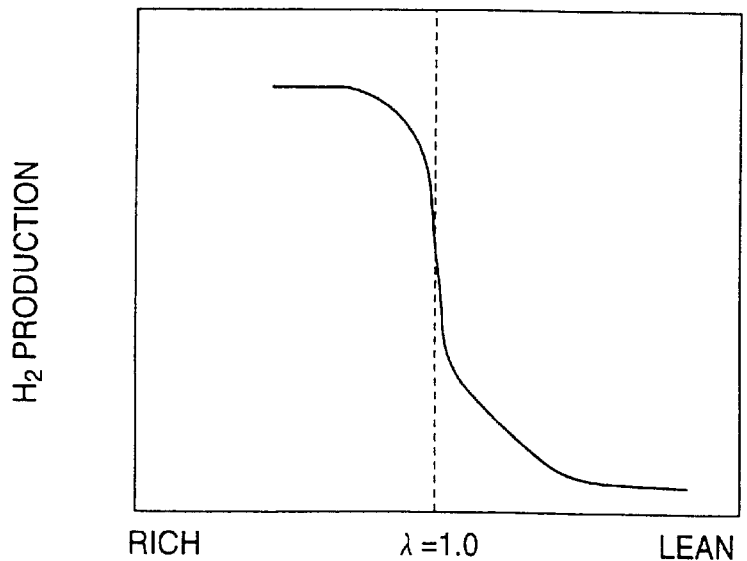
FIG. 15 is an illustration of the relationship between an excess air factor of a natural-gas-fueled engine and an $H_2$ quantity of an exhaust gas.

FIG. 14 shows the relationship between an excess air factor λ and a sensor current to be taken for when a common wide-area air-fuel ratio sensor with no installation of the catalyst layer 28 shown in FIG. 10 is placed before (upstream) and after (downstream) of the three-way catalytic converter 10 in a natural-gas-fueled engine. That is, an exhaust gas atmosphere containing hydrogen exists before the three-way catalytic converter 10, whereas an exhaust gas atmosphere not containing hydrogen lies after the three-way catalytic converter 10, and the measurement results of the output characteristics developed for when the sensor is disposed in each atmosphere are shown in the illustration. As shown in FIG. 15, in an area from a stoichiometric value to a rich, the $H_2$ concentration of an exhaust gas rapidly increases, and an $H_2$ rich condition develops in the vicinity of the sensor active surface (the surface of the outside electrode 14), with the result that the sensor output swings to the rich side as shown in FIG. 14.

Figure 16:
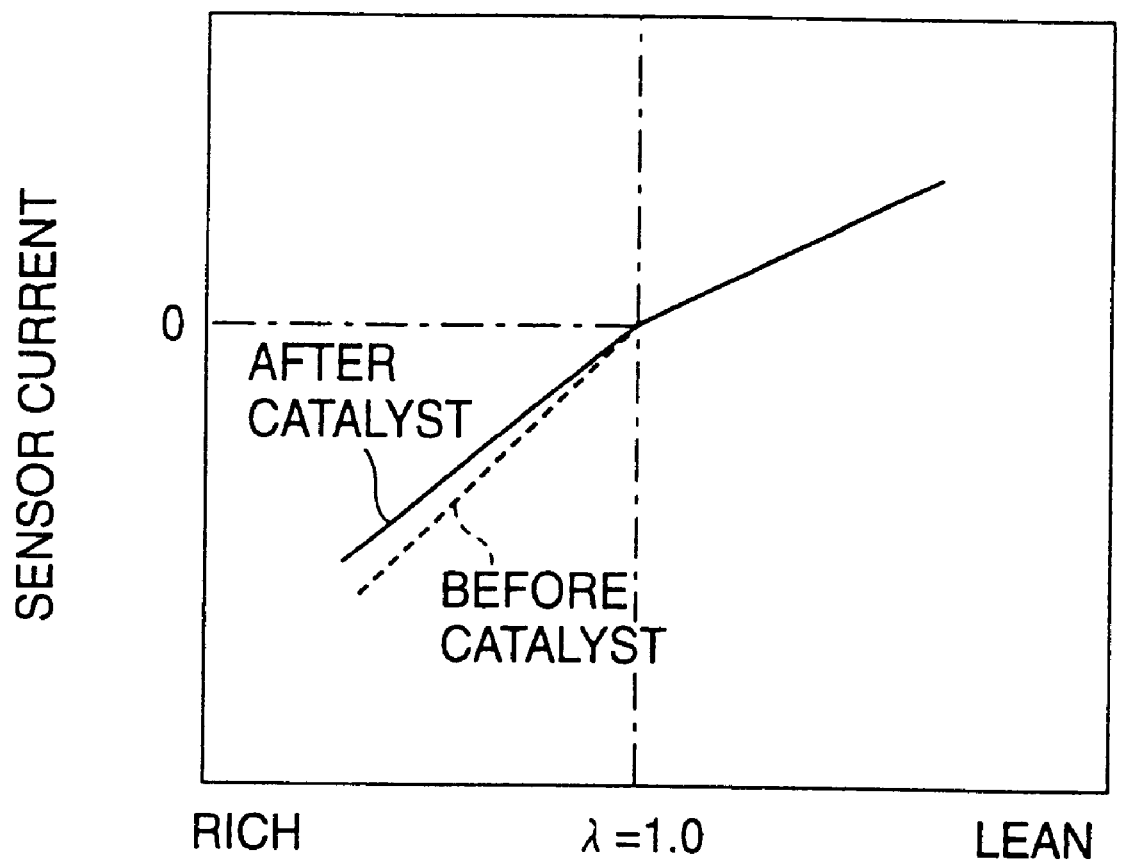
FIG. 16 is an illustration of an output characteristic of a wide-area air-fuel ratio sensor with a catalyst layer.

In the case that the catalyst layer 28 shown in FIG. 10 is provided in this air-fuel ratio sensor, the output slippage is suppressible as shown in FIG. 16.

(Third Embodiment)

The following description of a third embodiment will center on the difference from the first embodiment.

Figure 17:
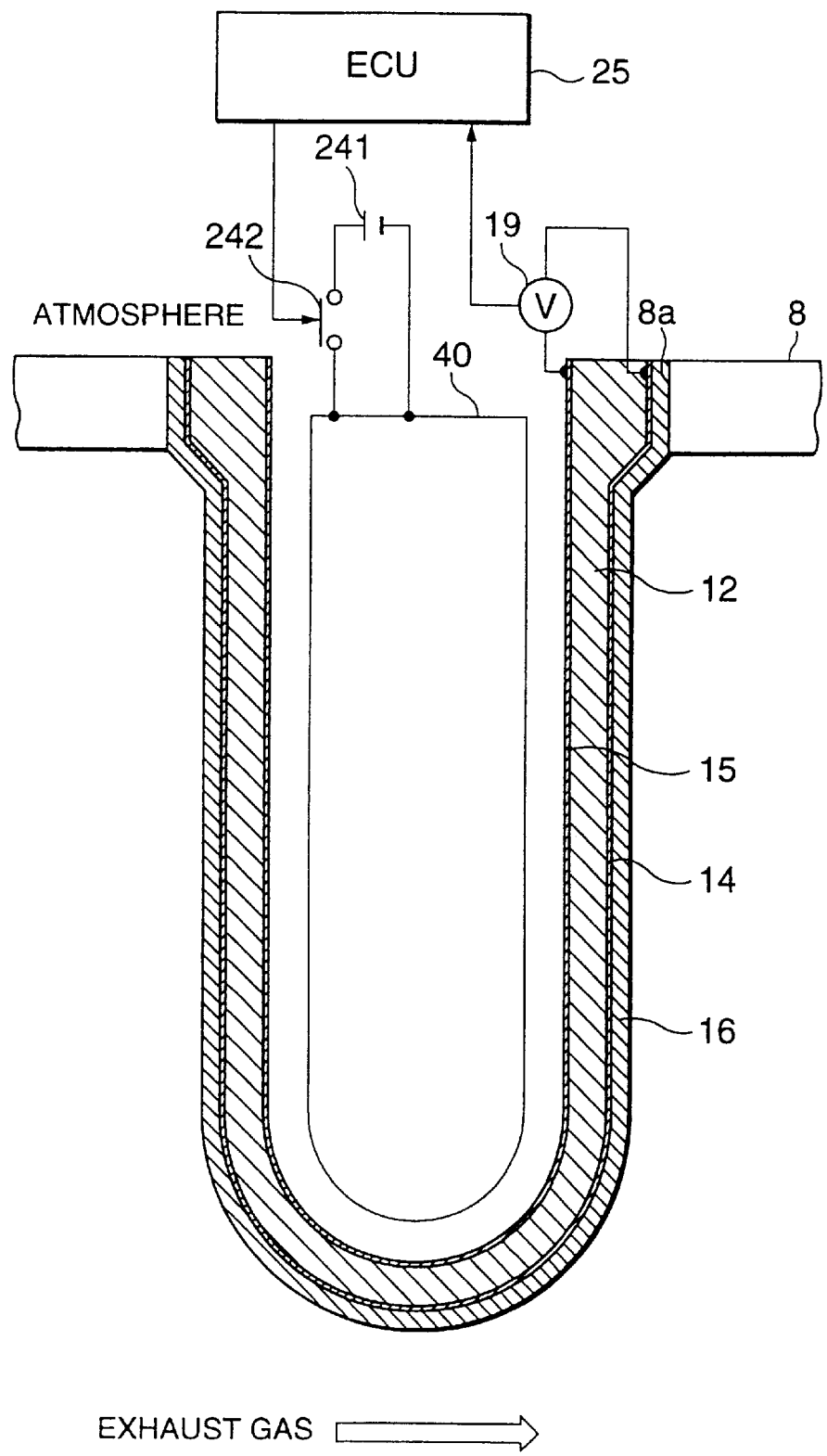
FIG. 17 is a cross-sectional view showing an $O_2$ sensor of an air-fuel ratio control system according to a third embodiment of this invention.

FIG. 17 is an illustration of a structure of an $O_2$ sensor in this embodiment. This structure is the same in a zirconia element 12, an inside electrode 15, an outside electrode 14 and a coating layer 16 as that shown in FIG. 2, but in this embodiment, a bar-like alumina heater 40 is put inside the cap-like element (solid electrolyte tube) 12. This sensor-contained sensor with a heater is equivalent to a sensor which has been employed for common gasoline engines for the purpose of being activated at an early stage. In FIG. 17, a power supply 241 is connected through a switching device 242 to the alumina heater 40. Further, the switching device 242 is under duty-control (ON/OFF control) by an ECU 25. In this control, the adjustment of the duty ratio allows the adjustment of a power supply quantity to the heater 40. That is, the power supply quantity increases as the duty ratio (ON time) increases.

Figure 18:
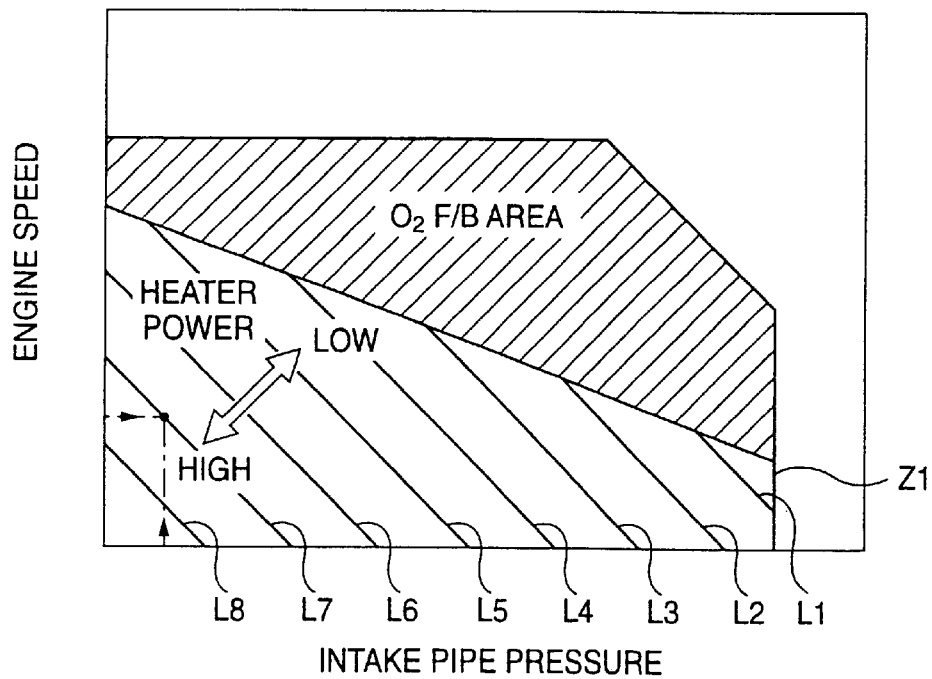
FIG. 18 is an illustration of a two-dimensional map for use in the third embodiment.

This control of the heater 40 is for determining the power to be supplied in accordance with a two-dimensional map based upon an engine speed and an intake pipe pressure so that the surface side temperature of the sensor outside electrode 14 exceeds 600° C. in an area Z1, where the exhaust temperature is below 600° C., shown in FIG. 18. That is, power supply characteristic lines L1 to L8 exist in the area Z1 where the exhaust temperature is below 600° C. In this case, the power supply characteristic L2 produces a more power supply as compared with L1, that is, the power supply is made to increase in the order of L3, L4, L5, L6, L7 and L8. Further, one of the characteristic lines L1 to L8 is selected on the basis of the engine condition (engine speed and intake pipe pressure) at that time to offer a power supply corresponding to the selected characteristic line.

In more detail, the heater control is done so that the surface side temperature of the sensor outside electrode 14 falls within a range of 600 to 700° C. The durability of the heater is securable with the surface side temperature being below 700° C. This can be satisfied as long as the surface side temperature of the sensor outside electrode 14 exceeds 600° C.

Figure 19:
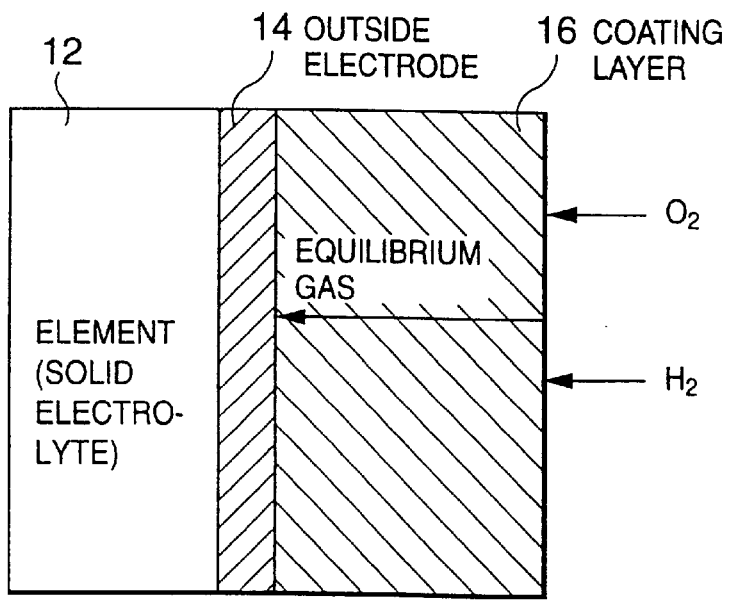
FIG. 19 illustratively shows an $O_2$ sensor in the third embodiment.
Figure 20:
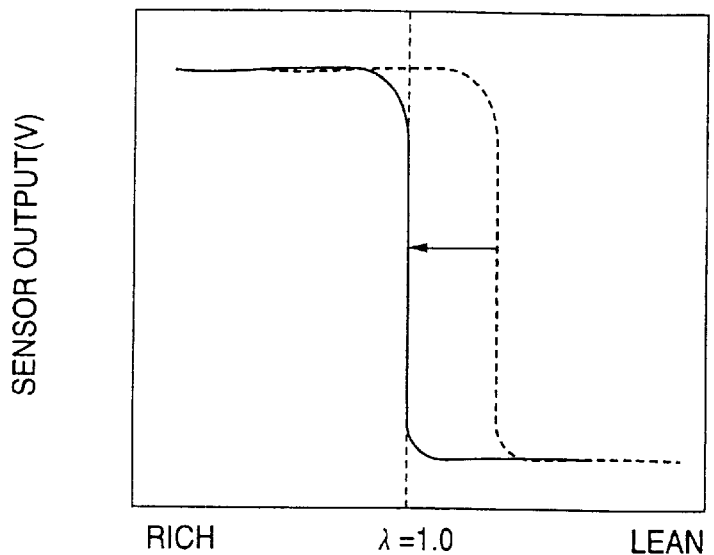
FIG. 20 is an illustration of an output characteristic of the $O_2$ sensor in the third embodiment.

Referring to FIGS. 19 and 20, a description will be given hereinbelow of the output slippage inhibitory effect by the heater control.

It is generally known that $H_2$ spontaneously burns when being above 600° C. in an oxidizing atmosphere, and as shown in FIG. 19, $H_2$ and $O_2$ react on the surface side of the outside electrode 14 with the surface temperature of the sensor outside electrode 14 being maintained to be above 600° C., and an equilibrium gas (after-reaction gas; $H_2O$ gas) passes through the coating layer 16. As a result, the output slippage is suppressible as indicated by a solid line in FIG. 20.

In FIG. 26, white "triangles" denote the case that the heater 40 in FIG. 17 is installed and the surface temperature is kept to be 700° C. As obvious from this, installing the heater 40 and maintaining 700° C. can reduce all HC, CO and $NO_x$, thereby suppressing the emission quantity after the three-way catalytic converter.

As described above, this embodiment has the following features.

The heater 40 is mounted on the $O_2$ sensor and the temperature outside the outermost electrode 14 is kept to be above 600° C. by means of the energization control of the heater 40 by the ECU 25. Thus, since the temperature outside the outside electrode 14 is kept to be above 600° C. by the heater 40, $H_2$ spontaneously burns to be removable. That is, the heater 40 and the ECU 25 function as a hydrogen invasion preventing means to prevent the invasion of hydrogen of an exhaust gas to the surface of the outside electrode 14 of the $O_2$ sensor. In this way, $H_2$ causing the sensor output slippage is eliminable from the reactive interface (the surface of the outside electrode), which permits an appropriate air-fuel ratio control operation without causing the sensor output slippage.

(Fourth Embodiment)

The following description of a fourth embodiment will focus on the difference from the first embodiment.

In this embodiment, without using the catalyst layer 17 in FIG. 2, the ECU 25 in FIG. 1 adjusts at least one of the comparison voltage (reference level) Vref, the proportional coefficients (gradually varying values at no inversion) KIL, KIR, the delay times (the times to be taken until the addition or subtraction of a correction coefficient from an inversion) TDR, TDL, and the skip quantities (the values to be added or subtracted at an inversion) SL, SR in FIG. 3 and puts the adjustment result in a memory in order to shift the control center of the air-fuel ratio feedback control to the rich side.

That is, the air-fuel ratio feedback control in the system shown in FIG. 4 is such that the ECU 25 compares the output of the $O_2$ sensor with the comparison voltage Vref to increase or decrease the feedback correction coefficient FAF. In this case, the control constants are Vref, SL, SR, KIL, KIR, TDR and TDL, and the control air-fuel ratio is controlled to the rich side with respect to a stoichiometric value in a manner of adjusting these constants (changing the rates of the constants).

Figure 21:
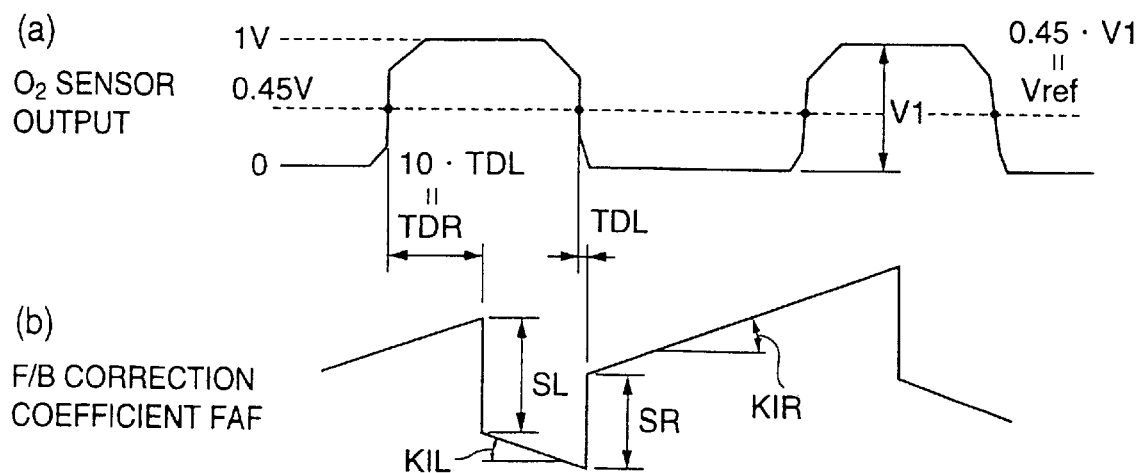
FIG. 21 is an illustration of a common FAF control.

For instance, in the common FAF calculating system shown in FIG. 21, the rich time length (rate) in the air-fuel ratio feedback cycle is prolonged by decreasing TDL or KIL, increasing TDR or KIR, or increasing Vref, whereupon the control center of the air-fuel ratio feedback control shifts to the rich side.

Figure 22:
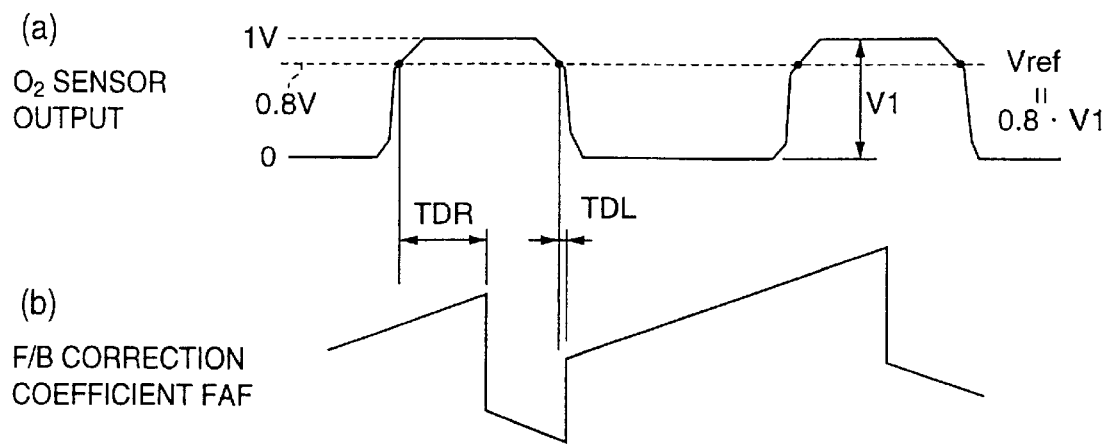
FIG. 22 is an illustration of a FAF control in an air-fuel ratio control system according to a fourth embodiment of this invention.

More specifically, for example, although the sensor output is in the range of 0 to 1V as shown in FIG. 21 and the comparison voltage Vref commonly assumes 0.45V, the comparison voltage Vref is set to be above 0.70V as shown in FIG. 22 (0.8V in FIG. 22). In other words, more than 70% of the sensor output voltage amplitude (1V) is set as the comparison voltage Vref.

Figure 23:
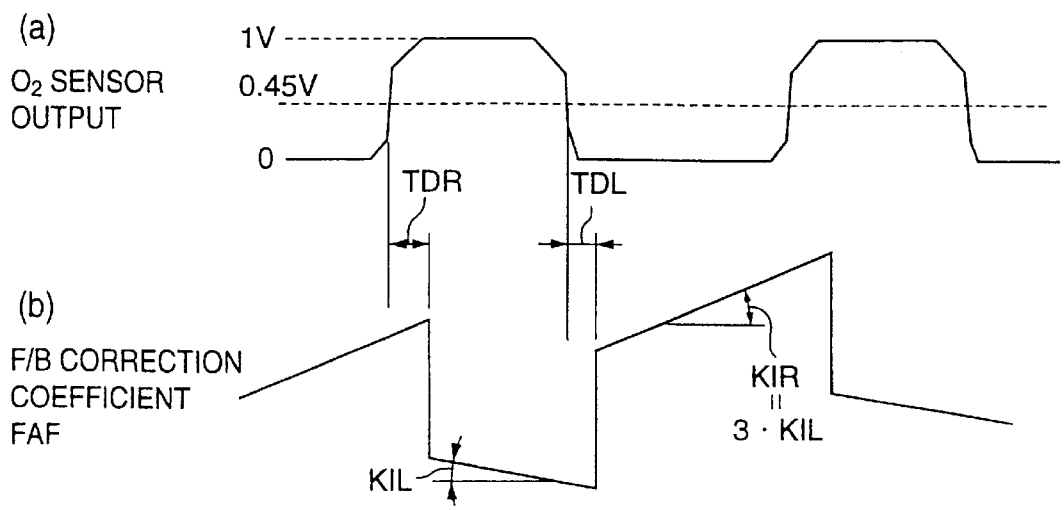
FIG. 23 is an illustration of a FAF control in the fourth embodiment.
Figure 24:
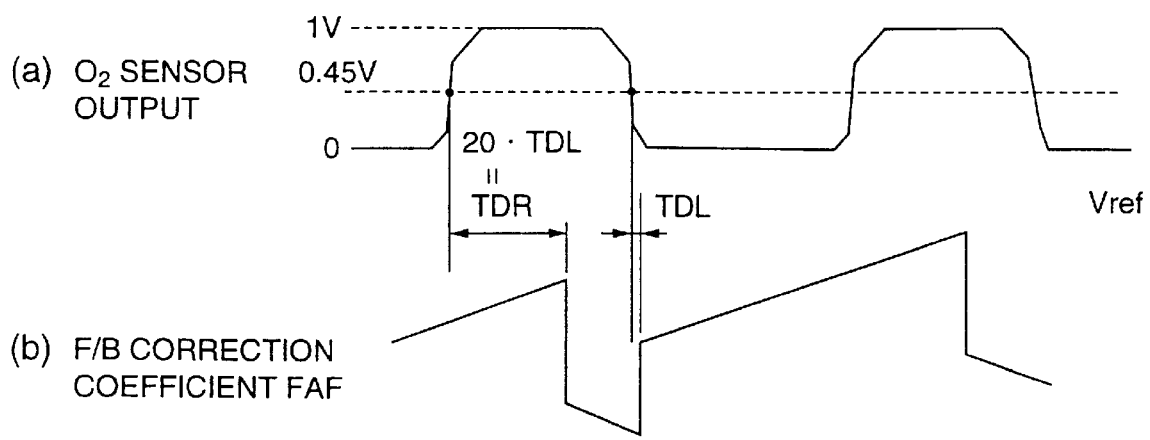
FIG. 24 is an illustration of a FAF control in the fourth embodiment.

In another way, although the proportional coefficient KIR is usually set to equal (one time) the proportional coefficient KIL as shown in FIG. 21, the proportional coefficient KIR is set to be three times the proportional coefficient KIL as shown in FIG. 23.

In a different way, although the delay time TDR is usually set to approximately ten times the delay time TDL as shown in FIG. 21, the delay time TDR is set to twenty times the delay time TDL.

As mentioned above, in the case of a natural-gas-fueled engine, since the output of the $O_2$ sensor swings to the lean side, the ratio between the aforesaid constants is adjusted accordingly, so that the control target can be set to the rich side. As a result, the actual A/F ratio is controlled to assume a stoichiometric value, which can offer an excellent catalyst purification performance.

In FIG. 26, "squares" represent change of the constants. As seen from this illustration, the change of the constants reduces all HC, CO and $NO_x$, thereby suppressing the emission quantity after the three-way catalytic converter. Concretely, if KIR=6%/sec and KIL=5%/sec before the adjustment are changed to KIR=10%/sec and KIL=2%/sec, the emission quantity after the three-way catalytic converter is suppressible as mentioned above.

This embodiment can provide the following feature.

The ECU 25 serving as a correction means has a correction function to correct the air-fuel ratio by the $O_2$ sensor to the rich side. That is, at least one of Vref, SL, SR, KIL, KIR, TDR and TDL in FIG. 3 is adjusted for the correction to the rich side. Whereupon, even if the output of the $O_2$ sensor shifts to the lean side, the target A/F controlled value based upon the $O_2$ sensor is set to the rich side in consideration of the shift quantity, thus allowing the optimum air-fuel control. In consequence, it is possible to suppress the emission quantity of each of HC, CO and $NO_x$ after the three-way catalytic converter.

(Fifth Embodiment)

The following description of a fifth embodiment will focus on the difference from the first to third embodiments.

In the system shown in FIG. 1, in the case that the sensor is equipped with a catalyst layer as in the first embodiment or where the sensor is provided with a heater as well as the third embodiment, in some engines, the sufficient $H_2$ removing ability of the sensor is unobtainable when the low-temperature gas flow rate increases in a high-speed and low-load region. This embodiment is for eliminating this problem.

Figure 25:
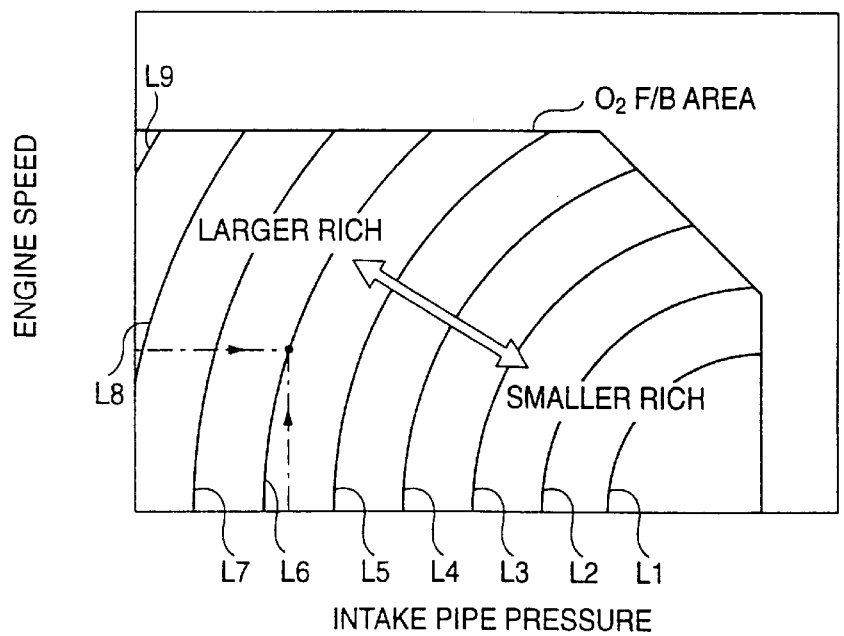
FIG. 25 is an illustration of a two-dimensional map for use in an fifth embodiment of this invention.

As shown in FIG. 25, an ECU 25 internally includes a map for determining the constants (Vref, SL, SR, KIL, KIR, TDR, TDL in FIG. 3) for the air-fuel ratio control on the basis of an engine speed and an intake pipe pressure, and increases the rich degree to the control objective in a high-speed and low-load region.

More specifically, characteristic lines L1 to L9 exist in the feedback area, and the characteristic L2 produces a more rich quantity as compared with L1, that is, the rich quantity is made to increase in the order of L3, L4, L5, L6, L7, L8 and L9. One of the characteristic lines L1 to L9 is selected in accordance with the engine condition (an engine speed and an intake pipe pressure), and a correction coefficient and others are taken so as to attain a rich quantity corresponding to the selected characteristic line.

Although the $H_2$ removing ability lowers on the high-speed and low-load side so that the slippage to lean tends to occur in the sensor, with the above-mentioned operation, the slippage of the control A/F to the lean is suppressible.

In addition to the above-described arrangements, it is also possible to combine the first, third and fourth embodiments. That is, along with the installation of the catalyst layer 17 in FIG. 2 and the heater 40 in FIG. 17, the operation can be employed which changes the constants (Vref, SL, SR, KIL, KIR, TDR and TDL in FIG. 3) for the air-fuel ratio feedback control. In this case, HC, CO and $NO_x$ all decrease significantly as indicated by "crosses" in FIG. 26, with the result that the emission quantity after the three-way catalytic converter is suppressible.

(Sixth Embodiment)

Figure 28:
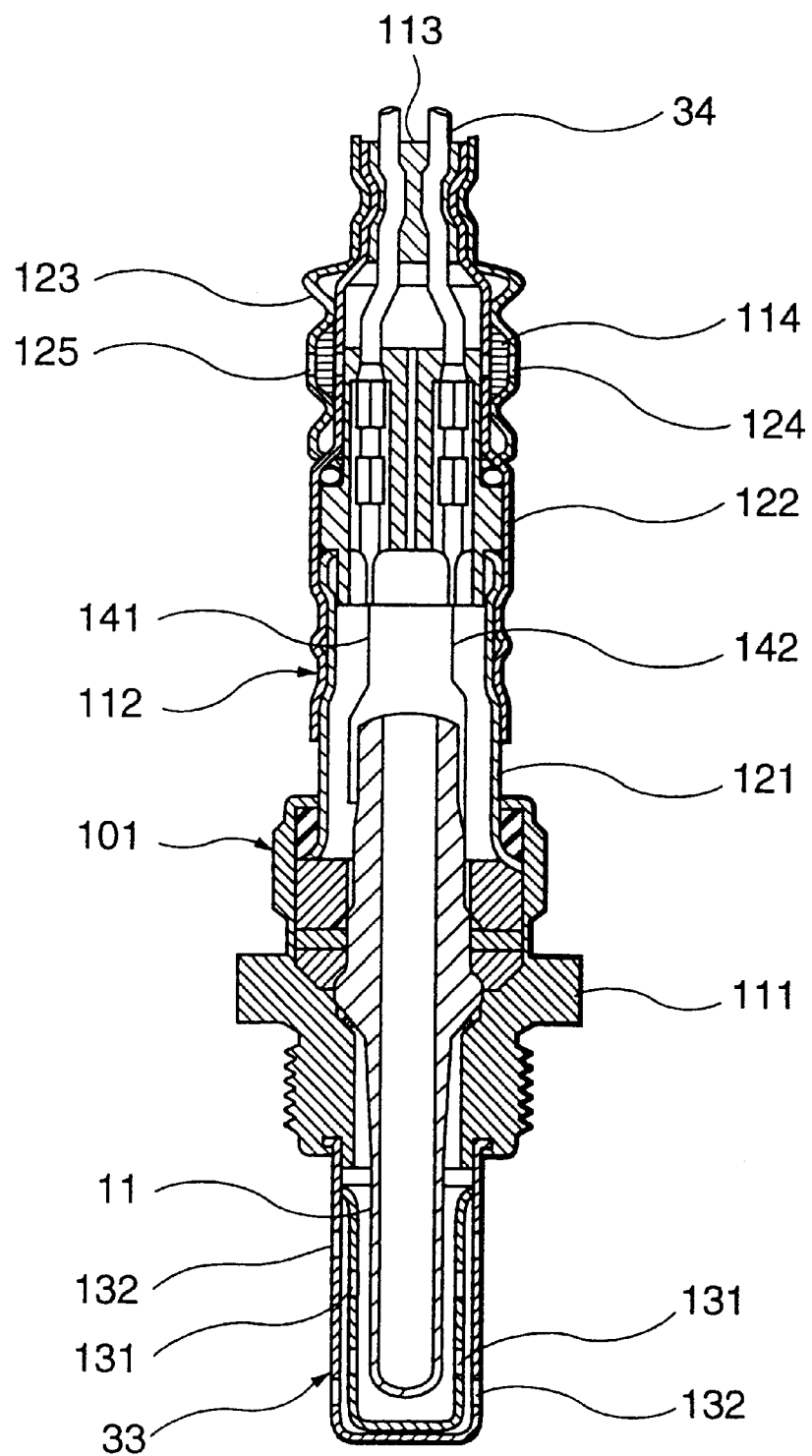
FIG. 28 is a cross-sectional view wholly showing the $O_2$ sensor according to the sixth embodiment.

Furthermore, a description will be made hereinbelow of an O2 sensor according to a sixth embodiment of this invention, which is used for controlling the air-fuel ratio in a natural-gas-fueled engine. FIG. 28 shows the entire construction of the $O_2$ sensor, with this $O_2$ sensor being composed of a cylindrical housing 101 attached to an exhaust pipe wall of a non-shown natural-gas-fueled engine and a gas detecting device 11 inserted into the interior of the cylindrical housing 101 and held therein. The cylindrical housing 101 is constructed such that a flange section 111 protruding from the outer circumference of a central portion of the cylindrical housing 101 comes into contact with the exhaust pipe wall and a screw section made thereunder is fitted to the exhaust pipe wall, so that the cylindrical housing 101 is fixedly secured to the natural-gas-fueled engine. The gas detecting device 11 has a test-tube-like configuration and its lower end portion protrudes with respect to the housing 101 to be within the exhaust pipe in a state of being accommodated with a cover body 33 fixedly secured to an lower end portion of the housing 101. The cover body 33 is of a double-tube type in which pluralities of gas flow holes 131, 132 are made in the side surface portions of the inner and outer tubes, respectively, so that an exhaust gas from the natural-gas-fueled engine is introduced through these gas flow holes 131, 132 toward the gas detecting device 11.

Above the housing 101, there is disposed a cylindrical cover 112 surrounding the outer circumference of the upper section of the gas detecting device 11. The cylindrical cover 112 is made up of a lower cover 121 fixed to the upper end portion of the housing 101 and an upper cover 122 caulking-fixed to the upper half section of the lower cover 121, and the outer circumference of the upper half section of the upper cover 122 is covered with a cylindrical member 123, thus establishing a double construction. An opening of the upper end of the upper cover 122 is hermetically sealed with a rubber bush 113, and lead wires 34 penetrate the rubber bush 113 and extend externally in order to fetch the output of the gas detecting device 11. Further, pluralities of atmosphere introduced holes 124, 125 are respectively made in the side portions of the upper cover 122 and the cylindrical member 123 in opposed relation to each other. The atmosphere introduced through these atmosphere introduced holes 124, 125 is led as a reference oxygen concentration gas into a hollow section of the gas detecting device 11. A water-repellent filter 114 is disposed at the positions corresponding to the atmosphere introduced holes 124, 125 between the upper cover 122 and the cylindrical member 123 for providing a water-proof function.

Figure 27:
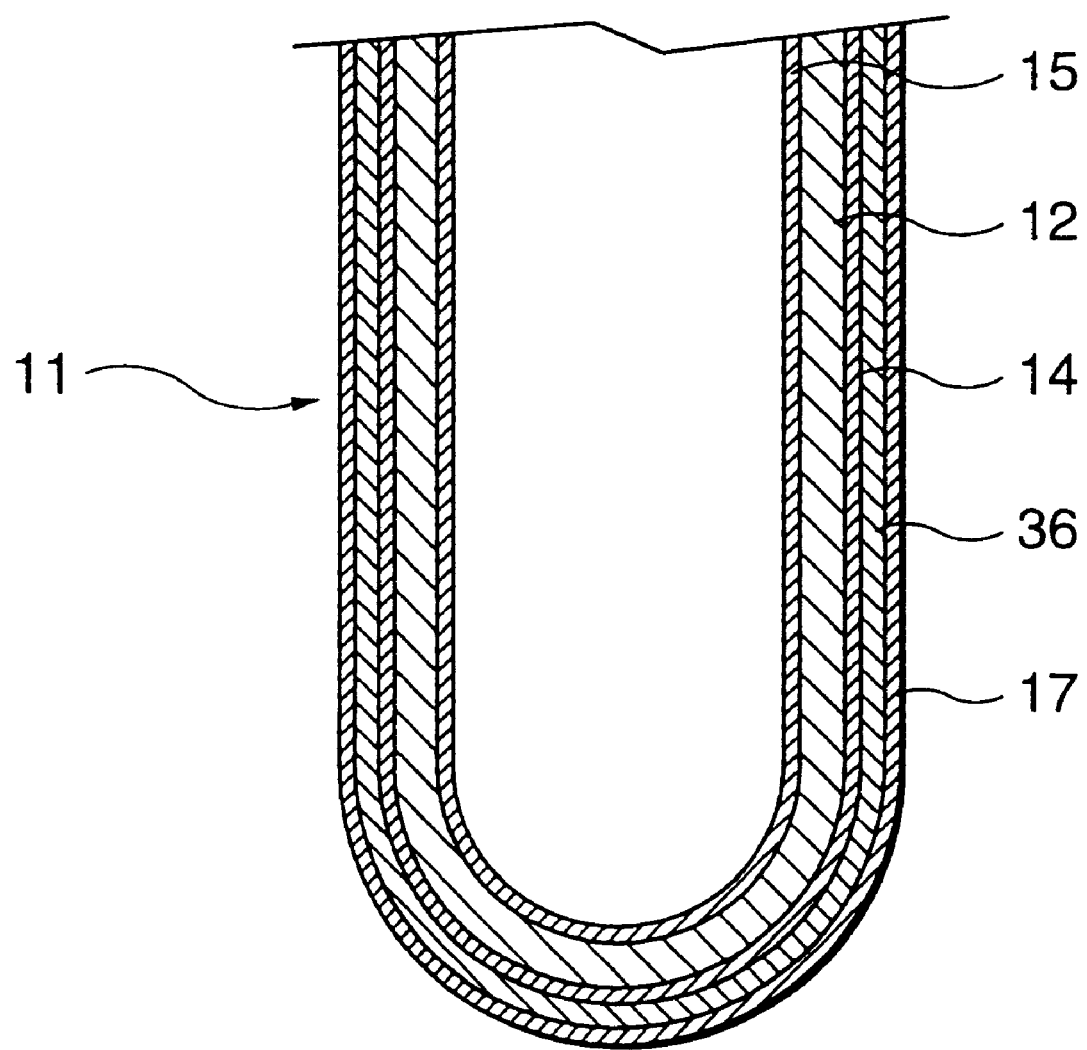
FIG. 27 is an enlarged cross-sectional view showing a principal portion of an $O_2$ sensor for a natural-gas-fueled engine according to a sixth embodiment of this invention.

As shown in FIG. 27, the gas detecting device 11 comprises an oxygen ion conductive solid electrolyte 12 made of zirconia or the like and shaped into a test-tube configuration, an inside electrode 15 serving as a first electrode and placed along an inner circumferential surface of the solid electrolyte 12, and an outside electrode 14 acting as a second electrode and placed along an outer circumferential surface of the solid electrolyte 12. These electrodes 14, 15 are made of, for example, platinum (Pt) or the like, and are formed by using a common means, such as deposition. Further, these electrodes 14, 15 are connected through output metallic terminals 141, 142 pressed into contact with a surface of the oxygen ion conductive solid electrolyte 12 to the lead wires 34 (see FIG. 28).

A protective coat 36 serving as a porous film is formed on an outer surface of the outside electrode 14 to protect the outside electrode 14 surface from harmful matters in an exhaust gas. The protective coat 36 is made of a porous ceramic such as a spinel ($MgO.Al_2O_3$), and is formed in a manner to perform plasma-spray-coating with the powder of the ceramic being a sprayed material. Further, the protective coat 36 is usually adjusted so that the porosity takes 7 to 10%. However, in the case of attaching much importance to the response characteristic, it is also possible that the porosity exceeds 10%, and in general, according to applications, the porosity is adequately determined to be a value below 25% which is needed to ensure the durability. Incidentally, the porosity is adjustable with the grain size of the sprayed material, the spraying power and others. The porosity increases with increase in the grain size and with decrease in the spraying power.

A feature of this embodiment is that the outer surface of the protective coat 36 is coated with a catalyst layer 17 fulfilling an oxidative effect. This catalyst layer 17 is made by carrying a catalytic metal (Pt, Pt—Rh, and other metals) on a porous ceramic such as alumina ($\gamma$-$Al_2O_3$, $\theta$-$Al_2O_3$, or the like), and oxidizes $H_2$ of an exhaust gas before it reaches the protective coat 36, thereby preventing the sensor output slippage. In this case, for ensuring the response characteristic, it is desirable that the porosity of the catalyst layer 17 is set to be larger than that of the protective coat 36, at least above 10%, preferably above 20%. For instance, as a way of forming the catalyst layer 17 there is a method in which a layer including a catalyst is formed on the protective coat 36 in a manner that, for example, $Al_2O_3$, the catalyst, a dispersant and other materials are put into a slurried solution, and is burned.

The catalyst layer 17 can provide a sufficient effect for the prevention of the aforesaid sensor output slippage if the catalytic metal carried quantity is above 0.5 wt % to the total weight of the catalyst layer 17. Increasing the catalytic metal carried quantity allows maintaining the catalytic performance for a long time, but concurrently creates a tendency to deteriorate the response characteristic. For this reason, in cases where the porosity of the protective coat 36 is within a common range of 7 to 10%, it is preferable that the catalytic metal carried quantity is below 2 wt %. Whereas, the more porosity of the protective coat 24 permits the increase in the catalytic metal carried quantity because of not greatly deteriorating the response characteristic. Concretely, when the porosity of the protective coat 36 is 10 to 25%, it is desirable that the catalytic metal carried quantity is set to 2 to 5 wt %. The relationship among the catalytic carried quantity, the porosity, the output characteristic and response characteristic will be described hereinlater.

The thicknesses of these layers are determined in consideration of the stability of the sensor output, the mechanical strength, the response characteristic and others, and it is usually preferable that the thickness of the protective coat 36 is within the range of 100 to 150 $\mu$m and the thickness of the catalyst layer 17 is within the range of approximately 10 to 50 $\mu$m. Further, in the case that the catalyst layer 17 is formed in the test-tube-like device 11, if the device 11 is configured so that its outer diameter is 6 mm and the catalyst layer 17 with a thickness of approximately 20 $\mu$m is formed to have a porosity of approximately 40 to 60% over the range of approximately 20 mm from its tip portion, the layer weight reaches approximately 15 mg.

Secondly, a description will be made hereinbelow of an operation or action of the catalyst layer 17 of the $O_2$ sensor thus constructed.

In FIG. 27, an exhaust gas passing through the catalyst layer 17 and the protective coat 36 is introduced to the outside electrode 14 of the gas detecting device 11 while the air is introduced to the inside electrode 15 thereof. At this time, an electromotive force corresponding to the difference in oxygen concentration between the inside electrode 15 and the outside electrode 14 develops in the oxygen ion conductive solid electrolyte 12, and the sensor output is supposed to rapidly vary at the excess air factor ($\lambda$)=1.0 as shown as a theoretical value in FIG. 29. Nevertheless, $H_2$ whose quantity is twice to three times that in an gasoline engine exists in an exhaust gas from an natural-gas-fueled engine, and therefore, in the prior construction with no catalyst layer 17, the point of the excess air factor ($\lambda$) at which the sensor output rapidly varies shifts to the lean side. This is, as mentioned before, because the diffusion velocity of $H_2$ assumes approximately four times that of $O_2$, and $H_2$ more quickly passes through the protective coat 36 to reach the surface of the outside electrode 14 than $O_2$, so that the outside electrode 14 takes an $H_2$ richer condition than the actual. Thus, a shortage of $O_2$ occurs on the outside electrode 14, and the rapidly output varying point of the output characteristic of the $O_2$ sensor swings to the lean side with respect to the theoretical value. In consequence, in the case of the prior construction, the appropriate air-fuel ratio control becomes impossible, which leads to a possibility of deteriorating the exhaust emission.

Figure 30:
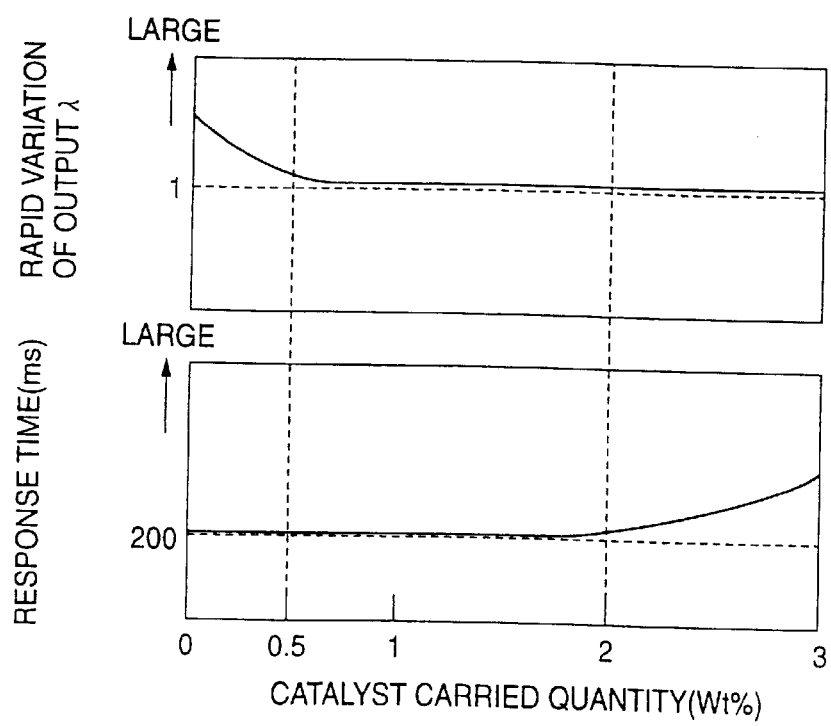
FIG. 30 is an illustration of the relationship among a catalyst carried quantity, output and response characteristic of an $O_2$ sensor.
Figure 31:
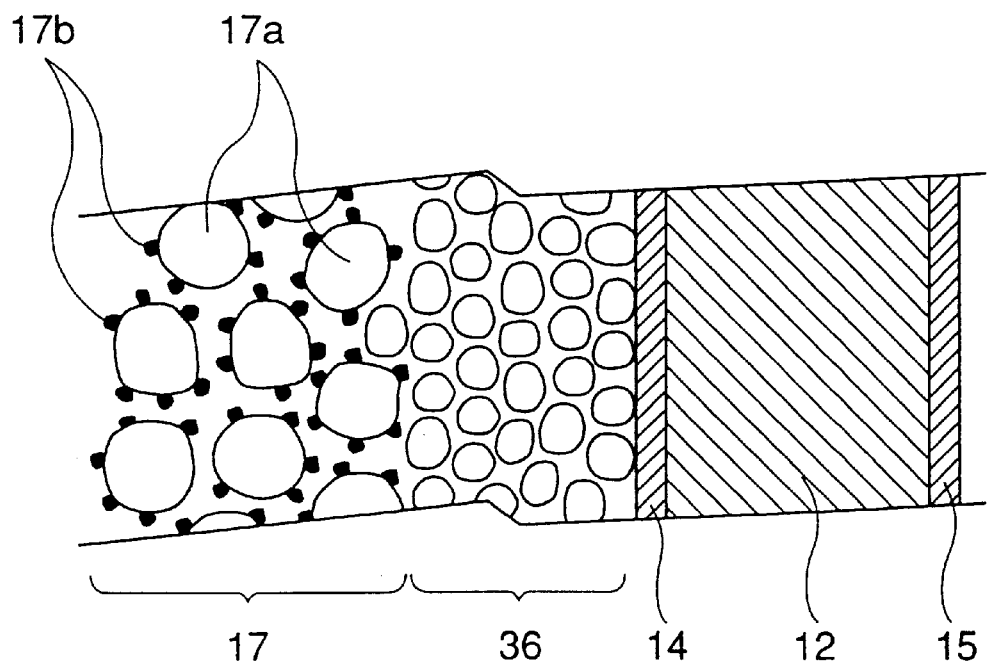
FIG. 31 illustratively shows a cross section of a principal portion of the $O_2$ sensor according to the sixth embodiment.

On the other hand, FIG. 30 (upper section) illustrates the relationship between the catalyst carried quantity and the slippage quantity of the sensor output in the case of the construction with the catalyst layer 17 shown in FIG. 27. This is made by examining the excess air factor ($\lambda$) taken when the sensor output varies up to 0.5V in a state where the catalyst carried quantity is increased, and in this case, the porosity of the protective coat 36 is 8 vol %. As seen from the illustration, as the catalyst carried quantity increases, the excess air factor ($\lambda$) at which the sensor output rapidly varies approaches the theoretical value which is 1, and when the catalyst carried quantity exceeds 0.5 wt %, the excess air factor ($\lambda$) assumes approximately 1. This mechanism will be described with reference to the illustrative drawing of FIG. 31. In the construction according to this embodiment, as shown in FIG. 31, the surface of the porous protective coat 36 is covered with the catalyst layer 17 with a higher porosity. In the catalyst layer 17, a catalytic metal 17b is carried by surface of fine particles or grains 17a such as $Al_2O_3$, and when an exhaust gas passes through the catalyst layer 17, $H_2$ of the exhaust gas is oxidized by the catalytic metal 17b. That is, a reaction expressed by the following formula is promoted.

$$2H_2+O_2 \rightarrow 2H_2O$$

Since the resultant $H_2O$ is stable, even if reaching the outside electrode 14, it does not affect the λ value leading to the rapid variation of the sensor output. Particularly, in the case that the catalyst carried quantity is above 0.5 wt %, it is considered that $H_2$ is completely oxidized to eliminate the influence of $H_2$ on the sensor output.

Meanwhile, the rapidly varying point of the sensor output becomes substantially constant in the catalyst carried quantity range above 5 wt %, and as shown in the lower section of FIG. 30, the response time of the sensor becomes longer from the vicinity of a point where the catalyst carried quantity exceeds 2 wt %, and the sensor output response characteristic further deteriorates as the catalyst carried quantity increases. One cause may be that the catalytic metal takes absorption action for HC and CO. That is, since the catalyst functions in the order of decreasing gas activity, in the range where the catalyst carried quantity is as small as below 2 wt %, it principally works on hydrogen. However, when the catalyst carried quantity increases, the catalyst also works on HC and CO being other unburned gas components, and hence, it is considered that the response delay takes place due to the reaction with these gasses and $O_2$. Another cause is that the closing of the pores tends to occur as a result of the increase in the catalytic metal.

From the above, when the catalyst carried quantity is set to be within the range of 0.5 to 2 wt %, it is possible to effectively display the catalytic action and further to suppress the sensor output slippage, which is a problem arising with a natural-gas-fueled engine, without deteriorating the response characteristic.

Subsequently, referring to FIG. 32, a description will be given hereinbelow of the relationship between the porosity of a protective coat and the response characteristic. In the case of an $O_2$ sensor in which the catalyst carried quantity is set to be within the range of 0.5 to 2 wt %, when the $O_2$ sensor is used in an environment which is not so severe, the above-mentioned effect can be exhibited for a relatively long term. However, in the case that it is put under a severe environment (high temperature, a large amount of gas), with the passage of time, there is a possibility that difficulty is experienced to maintain its initial performance because of peeling-off or the aggregation of the catalytic metal, or the like. Considering this aged deterioration, it is preferable to increase the catalyst carried quantity to a value above the aforesaid range. In the case of the $O_2$ sensor with the above-described structure, although, as mentioned above, the response characteristic further deteriorates as the catalyst carried quantity increases, as described below, this problem is solvable by adjusting the porosity of the protective coat 36.

The result shown in FIG. 30 shows the values obtained for when the porosity of the protective coat 36 is set to 8% like the conventional $O_2$ sensor for a gasoline engine. However, as compared with the gasoline engine, in the natural-gas-fueled engine, the exhaust gas contains less poisoning component (such as sulfur), less carbon grain and unburned component (HC), and the ignition timing can be advanced with a high octane number, and hence, the exhaust temperature lowers. For this reason, even if the porosity of the protective coat 36 is above 10%, the durability equivalent to that of the gasoline engine is obtainable.

Figure 32:
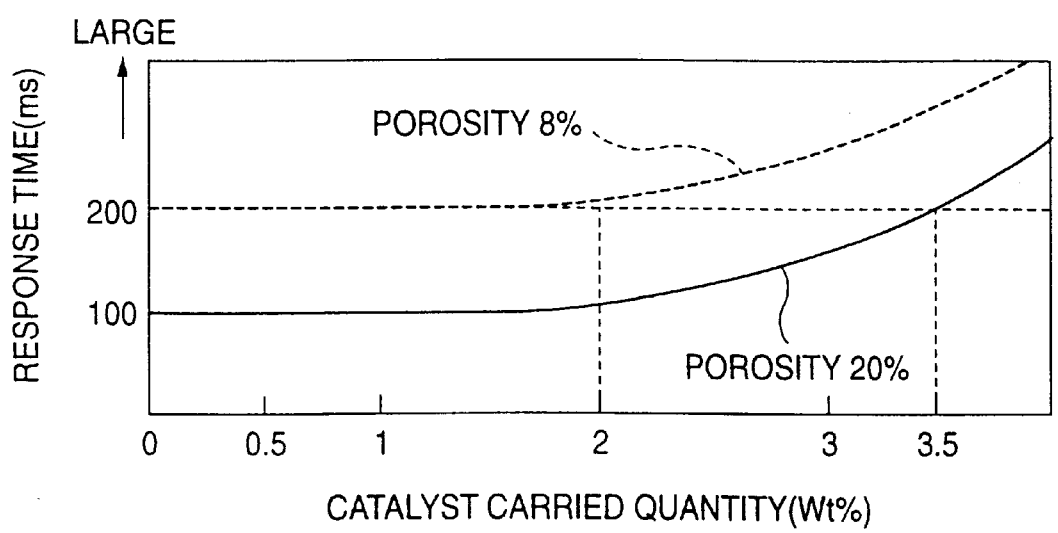
FIG. 32 is an illustration of the relationship among a porosity of a protective coat, a catalyst carried quantity and a response characteristic.
Figure 33:
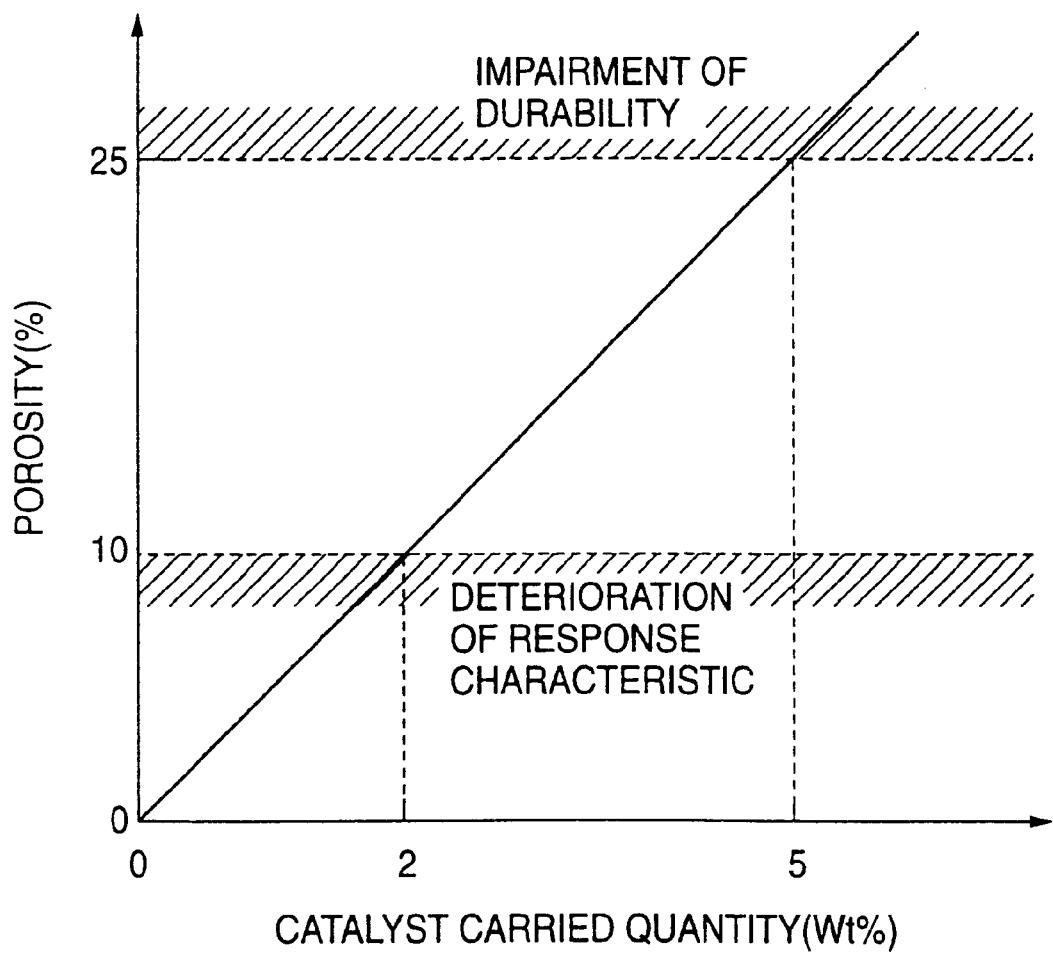
FIG. 33 is an illustration of the relationship among a porosity of a protective coat, a catalyst carried quantity, durability and a response characteristic.

FIG. 32 shows the difference in the relationship between the catalyst carried quantity and the response time between the case that the porosity of the protective coat 36 is 8% and the case that it is 20%. As shown in this illustration, the response time reduces to approximately half because of the increase (20%) in the porosity of the protective coat 36, and even if the catalyst carried quantity exceeds 2 wt %, the response time remains below the minimum response time (200 ms) corresponding to the 8% of porosity. That is, even if the catalyst carried quantity increases, up to 3.5 wt % whereby the response time reaches 200 ms, a higher or equivalent response characteristic is obtainable. Further increasing the porosity of the protective coat 36 results in the rise in the upper limit of the catalyst carried quantity, the relationship between the porosity of the protective coat 36 and the catalyst carried quantity is as shown in FIG. 33. Thus, if the upper limit of the porosity of the protective coat 36 is set to 25% in consideration of the durability of the protective coat 36, then the upper limit of the catalyst carried quantity corresponding thereto reaches 5 wt %.

From the above-mentioned results, in the case that the porosity of the protective coat 36 is set to be above 10%, it is possible to carry the catalyst by more than 2 wt %. In detail, if the porosity of the protective coat 36 is set to 10 to 25% and the catalyst carried quantity is set to 2 to 5 wt %, the durability and the response characteristic are compatible with each other and the deterioration of the catalytic effect is preventable regardless of a long-term use.

(Seventh Embodiment)

Figure 34B:
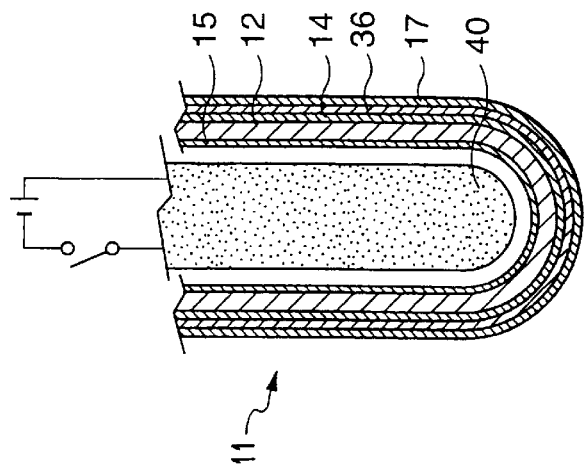
FIG. 34B is an enlarged cross-sectional view showing a principal portion of the same $O_2$ sensor.
Figure 34A:
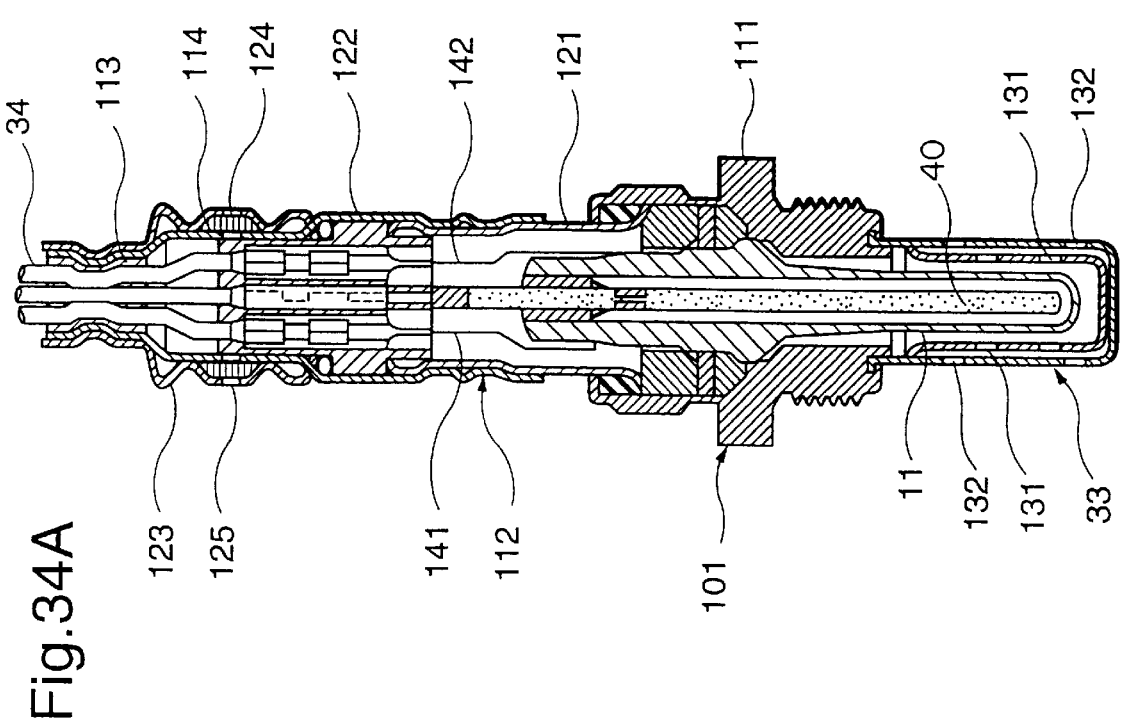
FIG. 34A is a cross-sectional view wholly showing an $O_2$ sensor according to a seventh embodiment of this invention.

FIGS. 34A and 34B are illustrations of a seventh embodiment of this invention. In this embodiment, in an $O_2$ sensor 11 with a structure corresponding to the structure shown in FIG. 27, a heater 40 is disposed within a hollow section of an oxygen ion conductive solid electrolyte 12 for heating the $O_2$ sensor 11. The other parts are same as that of the sixth embodiment. The heater 40 is constructed using an insulator having a bar-like, plate-like or tube-like configuration, and for example, is constructed by embedding a heating element, such as tungsten (W) and molybdenum (Mo), in the interior of $Al_2O_3$. The heating element is connected through lead wires to an external power supply. The power to be supplied to the heater 40 is controlled in accordance with a map made out in advance on the basis of the engine conditions, or is feedback-controlled on the basis of the resistance value of the heater 40, so that the temperature of the oxygen ion conductive solid electrolyte 12 becomes an active temperature, usually above 300° C.

With this structure, the installation of the heater 40 can ensure the hydrogen removing ability of the catalyst layer even under the condition that the exhaust temperature is low, for example, which occurs at an engine cold start or at a low load, so that the sensor output slippage is preventable in a wider range.

(Eighth Embodiment)

Figure 35:
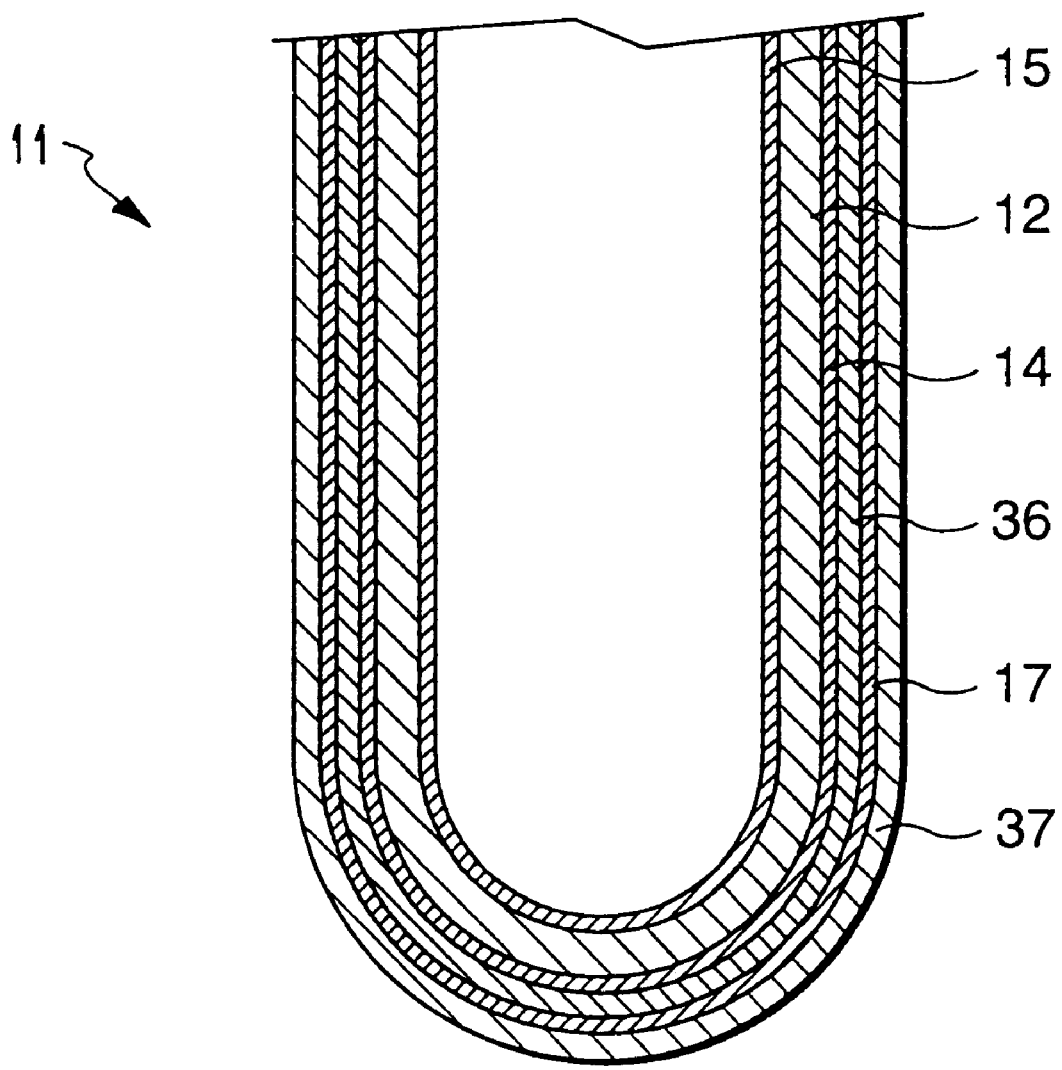
FIG. 35 is an enlarged cross-sectional view showing a principal portion of an $O_2$ sensor according to an eighth embodiment of this invention.

FIG. 35 is an illustration of an eighth embodiment of this invention. The feature of this embodiment is that, in addition to the structure of the $O_2$ sensor according to each of the above-described embodiments, the outside of a catalyst layer 17 is covered with a trap layer 37 made from a porous layer. The other parts are the same as that of the sixth embodiment. The trap layer 37 is made of a porous ceramic, such as $Al_2O_3$, and its porosity is higher than that of the catalyst layer 17, and usually, it is preferable that it is above 20%, and more preferably 40 to 60%. The installation of this trap layer 37 can prevent a deposit component produced by the combustion of an engine oil or the like from passing through the catalyst layer 17 to invade into a protective coat 36. Thus, it is possible to prevent the closing of the pores of the protective coat 36, and further to prevent the flying of the catalytic metal or the peeling-off of the catalyst layer 17 in a manner as to suppress the direct introduction of the exhaust gas into the catalyst layer 17. In this case, it is also appropriate that the trap layer 37 is constructed by piling up a plurality of porous layers different in porosity.

(Ninth Embodiment)

Figure 36:
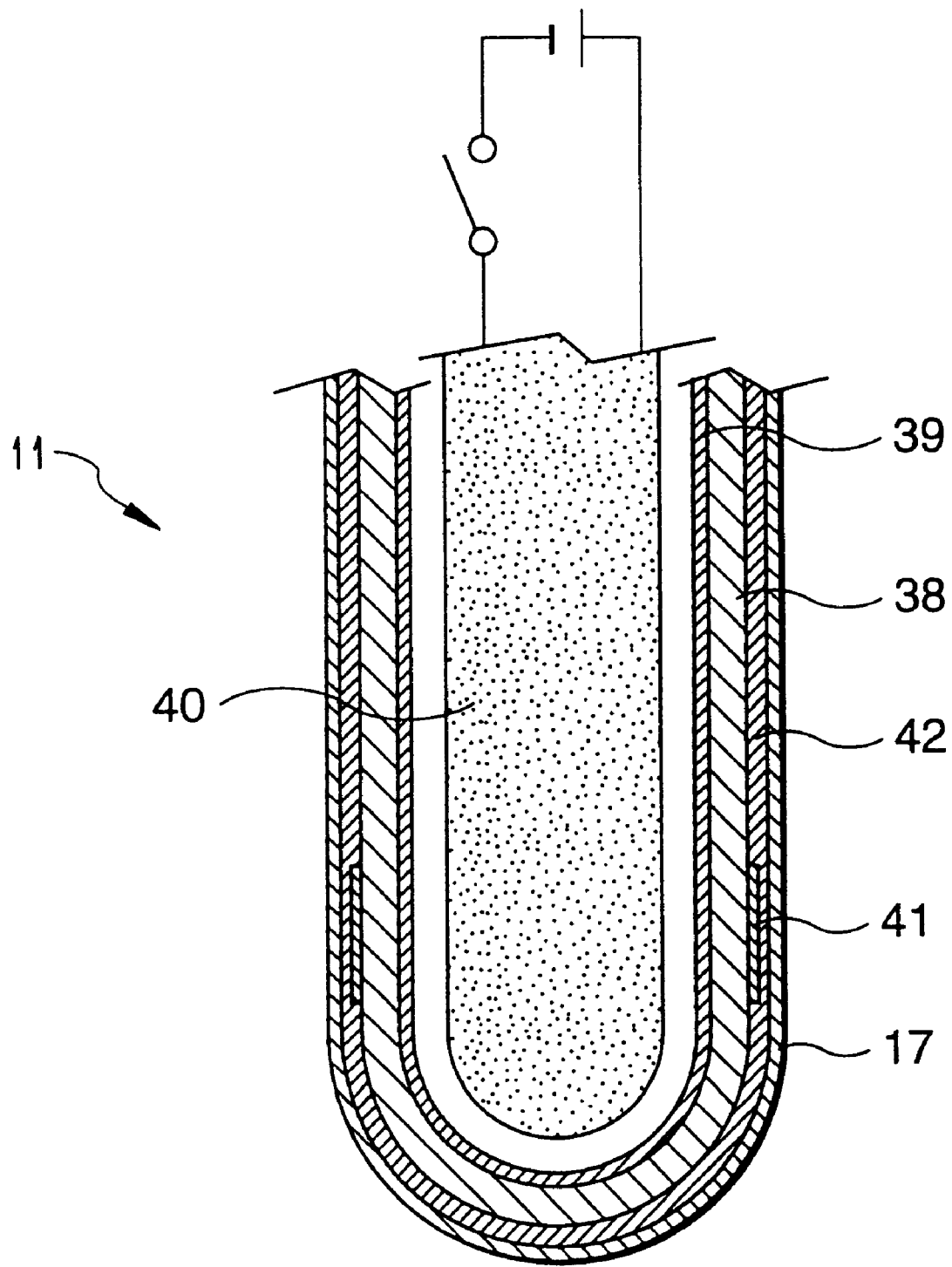
FIG. 36 is an enlarged cross-sectional view showing a principal portion of a wide-area air-fuel ratio sensor according to a ninth embodiment of this invention.

FIG. 36 is an illustration of a ninth embodiment of this invention. This embodiment relates to the application of this invention to a limiting current type air-fuel ratio sensor with a diffusion resistance layer. Similarly, when an air-fuel ratio sensor for detecting an air-fuel ratio in a wider range is used for an natural-gas-fueled engine, this creates a sensor output slippage problem. This problem is solvable in a similar way. The entire structure of the air-fuel ratio sensor is substantially similar to the structure of the $O_2$ sensor shown in FIG. 28, and the following description will be limited to the difference therebetween.

FIG. 36 shows a principal portion of a gas detecting device 11 to be employed as an air-fuel ratio sensor. In this embodiment, an inside electrode 39 acting as a first electrode, made of Pt or the like, is formed along an inner circumferential surface of an oxygen ion conductive solid electrolyte 38 made of zirconia or the like and shaped into a test-tube-like configuration. In addition, an outside electrode 41 serving as a second electrode, made of Pt or the like, is provided over a given width on the outer circumferential surface of the oxygen ion conductive solid electrolyte 38 and in the vicinity of the tip portion thereof. The inside electrode 39 and the outside electrode 41 are coupled to lead wires (not shown) extending toward the external in a state where metallic terminals pressed into contact with a surface of the oxygen ion conductive solid electrolyte 38 is put therebetween. Further, a device-heating bar-like heater 40 is accommodated within a hollow section of the gas detecting device 11, and is connected through lead wires to an external power supply.

In addition, a diffusion resistance layer 42 is formed on the surface of the outside electrode 41 and on the outer surface of the aforesaid solid electrolyte 38. The diffusion resistance layer 42 is constructed with a porous ceramic such as $Al_2O_3$, and its porosity is usually set to 2 to 7%. Further, the thickness of the diffusion resistance layer 42 is usually formed to be within approximately 400 to 700 $\mu$m.

The outer surface of the diffusion resistance layer 42 is coated with a catalyst layer 17 exhibiting an oxidizing action or effect. The catalyst layer 17 is made in manner that a catalytic metal such as Pt and Pt—Rh is carried by a porous ceramic such as alumina, and oxidizes $H_2$ contained in an exhaust gas before the exhaust gas passes through the diffusion resistance layer 42, thereby preventing the sensor output slippage. In this case, in order to assure the response characteristic, the porosity of the catalyst layer 17 is set to be at least above 10%, preferably above 20%. The catalytic metal carried quantity is determined to be above 0.5 wt % to the total weight of the catalyst layer 17 like the aforesaid $O_2$ sensor does, so that a sufficient effect on the sensor output slippage is attainable. In addition, in order to ensure the response characteristic, it is preferable that the catalytic metal carried quantity is set to be below 2 wt %. Usually, the thickness of the catalyst layer 17 is preferable to be approximately 10 to 50 $\mu$m.

Figure 37A:
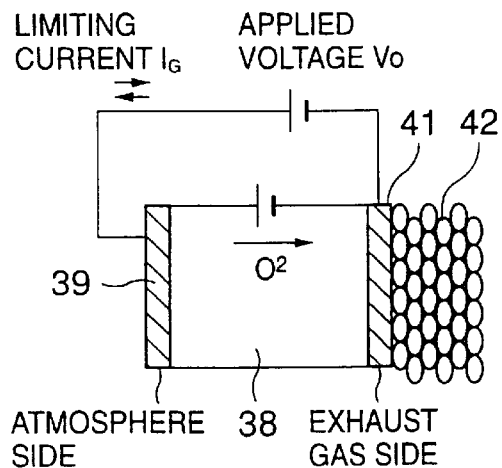
FIGS. 37A to 37E are illustrations useful for describing the detection principal of a wide-area air-fuel ratio sensor.
Figure 37B:
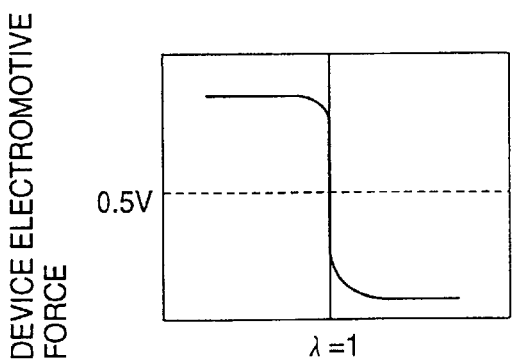

Subsequently, a description will be made hereinbelow of the detection principle of the air-fuel ratio sensor with the above-described structure. In FIG. 37A, when a voltage $V_0$ is applied between an inside electrode 39 and an outside electrode 41 placed on both the surfaces of an oxygen concentration detecting device 11, depending upon the difference in oxygen concentration between both the electrodes 39, 41, oxygen ions ($O_2^-$) move within an oxygen ion conductive solid electrolyte 38. Accordingly, when a voltage of 0.5V (see FIG. 37B) equivalent to an electromotive force occurring at the excess air factor ($\lambda$)=1 is applied between both the electrodes 39, 41 in the opposite direction, the air-fuel ratio is detectable on the basis of the value of the limiting current flowing between both the electrodes 39, 41.

Figure 37C:
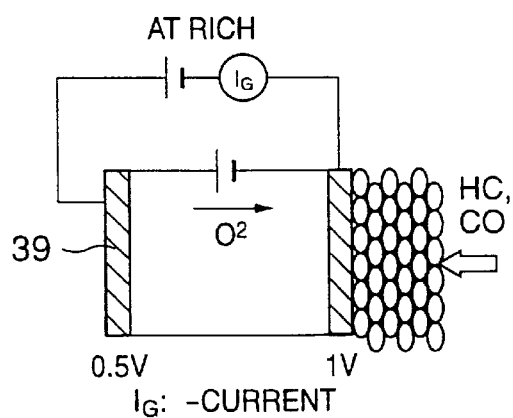
Figure 37D:
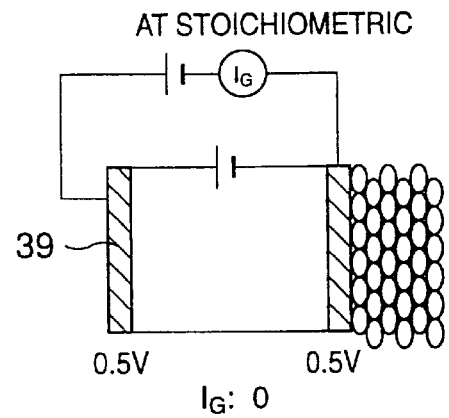
Figure 37E:
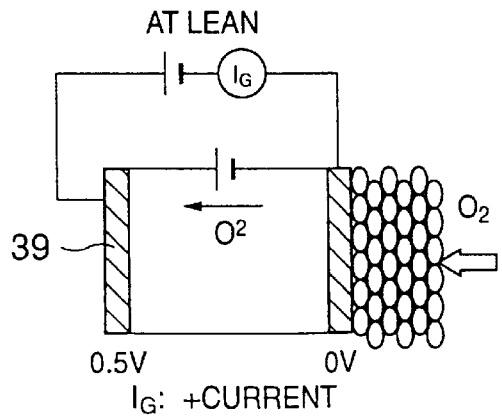

This current assumes zero (FIG. 37D) at a stoichiometric value (theoretical air-fuel ratio) because the device electromotive force balances with the applied voltage. In a lean condition, since the device electromotive force comes to zero, due to the applied voltage, the oxygen of an exhaust gas passing through the diffusion resistance layer 42 and then reaching the outside electrode 41 further passes through the oxygen ion conductive solid electrolyte 38 to arrive at the inside electrode 39, thereby producing a + current (FIG. 37E). On the other hand, in a rich condition, since the device electromotive force turns to 1, due to the difference from the applied voltage, the oxygen moves from the inside electrode 39 toward the outside electrode 41, thereby producing a − current (FIG. 37C). The current flowing at this time depends upon the quantity of $O_2$ passing through the diffusion resistance layer 42 in the lean condition while depending on the quantities of HC and $CO_2$ passing through the diffusion resistance layer 42 in the rich condition, and therefore, if a large amount of $H_2$ exists in an exhaust gas like a natural-gas-fueled engine, the current value varies even in the case of the same air-fuel ratio.

Figure 38:
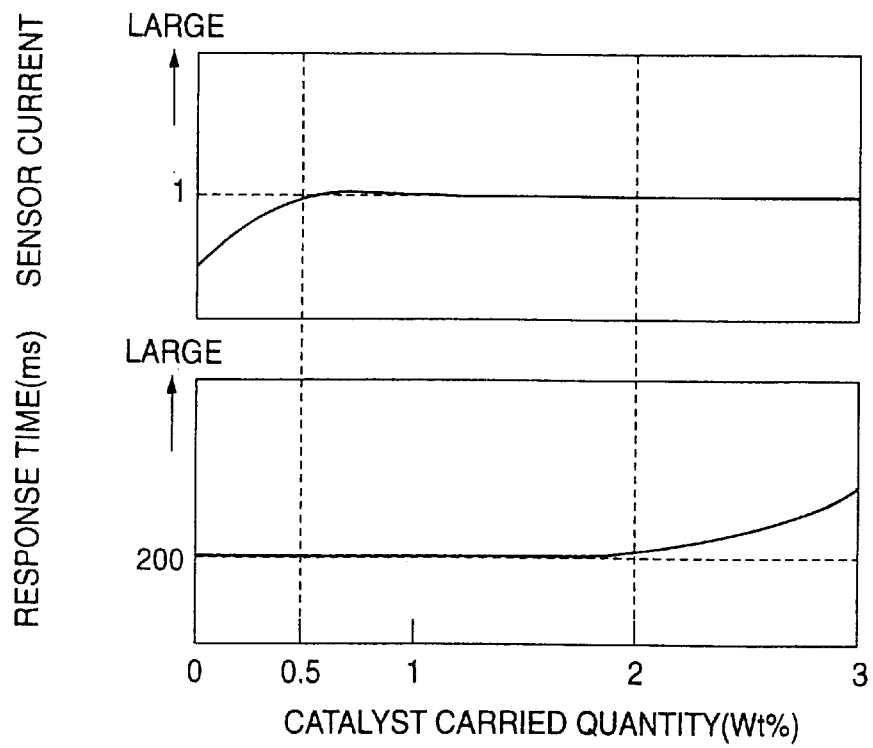
FIG. 38 is an illustration of the relationship among a catalyst carried quantity, output and response characteristic of a wide-area air-fuel ratio sensor.
Figure 39:
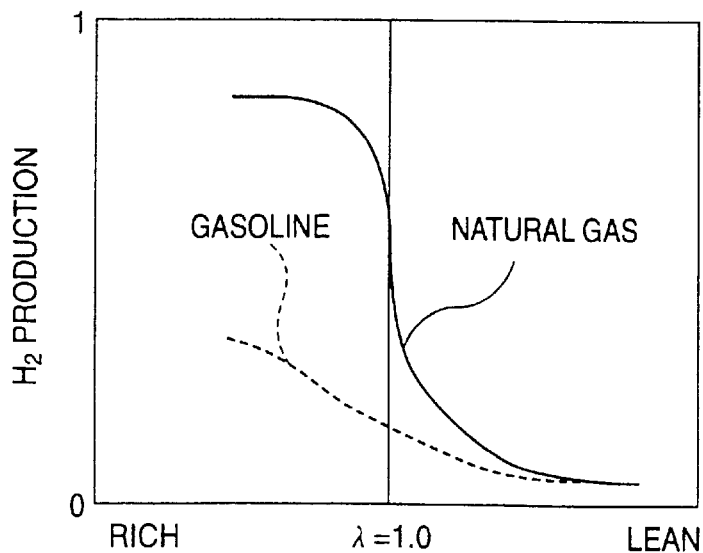
FIG. 39 is an illustration of the relationship between an air-fuel ratio and hydrogen production in a natural-gas-fueled engine.

As seen from FIG. 14 showing the relationship between the excess air factor ($\lambda$) and the limiting current on the upstream and downstream side of the three-way catalytic converter located in an exhaust pipe of a natural-gas-fueled engine, when taking a rich condition with respect to a stoichiometric value, since $H_2$ of an exhaust gas rapidly increases (FIG. 38), an $H_2$ rich condition takes place in the vicinity of the sensor outside electrode 41 so that the sensor output swings to the rich side. This embodiment solves this output slippage by providing the aforesaid catalyst layer 17 as in the case of the $O_2$ sensor. The upper section of FIG. 38 shows a variation of the output current at the excess air factor (λ) when the catalyst carried quantity increases, while the lower section of FIG. 38 shows a variation of the sensor response time with the increase in catalyst carried quantity. With the increase in catalyst carried quantity, the output current increases, and when exceeding 0.5 wt %, it becomes approximately zero. This signifies that $H_2$ causing the output slippage is completely removable in the case that the catalyst carried quantity is above 0.5 wt %. Further, when exceeding 2 wt %, the response characteristic deteriorates. From the above, if the catalyst carried quantity is set to be within the range of 0.5 wt % to 2 wt %, the suppression of the sensor output slippage and the response characteristic are compatible with each other.

Figure 58:
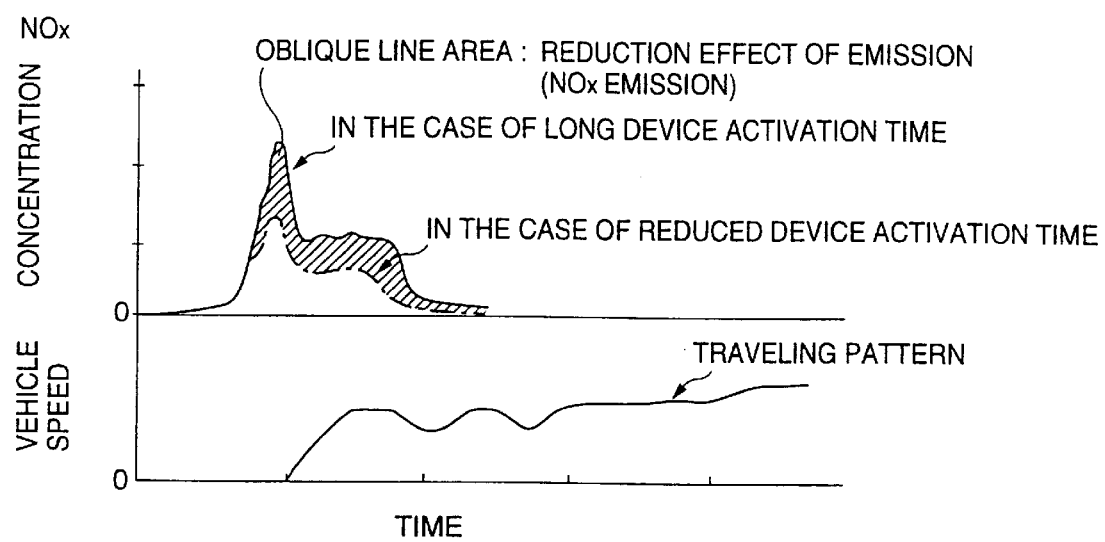
FIG. 58 is an illustration of the relationship between a device activation time and an exhaust emission.

In the case of the natural-gas-fueled engine, its ignition timing is frequently advanced for the purpose of enhancing its torque, and hence, the exhaust temperature is lower as compared with that of a gasoline engine. For this reason, it takes time until the device temperature reaches the activating temperature, with the result that the controllability may deteriorates because of the delayed control start. Particularly, in the case of a limiting current type air-fuel ratio sensor, its minimum operating temperature is high as approximately 700° C. as compared with an $O_2$ sensor whose minimum operating temperature is approximately 300° C., and hence, the time needed for raising the temperature is long, and the required power quantity for the heater 40 installed for heating the device increases. In addition, in cases where the heater 40 is put in an hollow section of a test-tube-like gas detecting device 11 as shown in FIG. 36, since the heat transfer efficiency is poor because the heater 40 and the device 11 are disposed independently of each other, there is a problem that the power consumption quantity tends to increase. The installation of the catalyst layer 17 can solve this problem. That is, the heat generated at the oxidizing reaction of $H_2$ in the catalyst layer 17 assists the temperature rise of gas detecting device 11. Besides, since the catalyst layer 17 is installed integrally with the gas detecting device 11, the heat transfer efficiency becomes high. Thus, it is possible to noticeably reduce the activation time, thereby allowing a quicker device operation, with the result that the exhaust emission is reducible as shown in FIG. 58. In addition, the power consumption of the heater 40 comes down to prolong the life of the heater 40.

Figure 40:
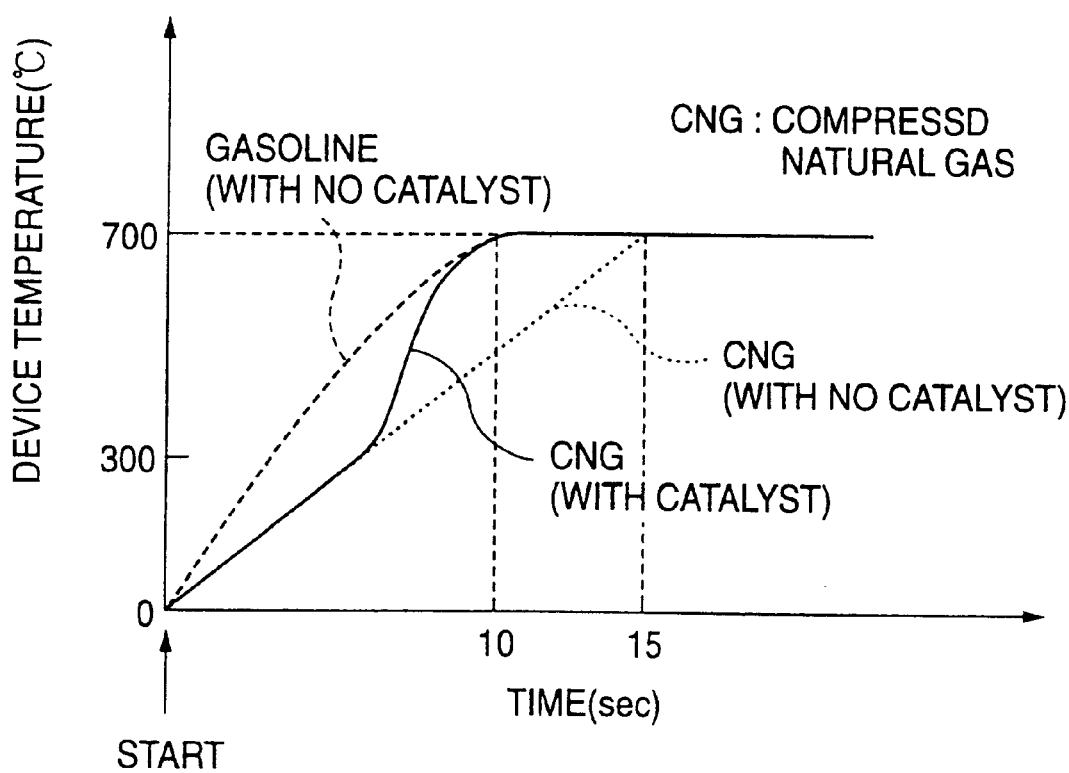
FIG. 40 is an illustration of variation of the temperature of the gas detecting device depending on the presence or absence of the catalyst layer.

FIG. 40 shows an effect obtainable by the catalyst layer 17. In the case of no installation of the catalyst layer 17, in a natural-gas-fueled engine (CNG) whose exhaust temperature is lower than that of a gasoline engine, the rise of the device temperature from its start is slow, and the time to be taken until the device temperature reaches 700° C. is 15 seconds, although the gasoline engine takes 10 seconds. On the other hand, in the case of the installation of the catalyst layer 17, the temperature rise is promoted from the vicinity of the device temperature of 300° C., with the result that the activation time becomes equivalent to that of the gasoline engine. That is, the installation of the catalyst layer 17 can sharply shorten the activation time. Although this temperature rising effect more effectively appears in a natural-gas-fueled engine whose exhaust temperature is low, the installation of the catalyst 17 is off-course effective to not only the natural-gas-fueled engine but also the gasoline engine or the like, and even in this case, the quicker sensor operation is achievable.

As described above, this structure can realize an air-fuel ratio sensor for a natural-gas-fueled engine which produces no sensor output slippage but has a high detection accuracy. Accordingly, when being applied, for example, to an natural-gas-fueled engine based upon an injection system, this air-fuel ratio sensor allows high-accuracy air-fuel ratio control and improves the exhaust emission, and hence, can sufficiently cope with the new exhaust gas regulation in United States of America, and further, can be put to practical use in more nations. Incidentally, it is also possible that the trap layer shown in FIG. 35 is added to the air-fuel ratio sensor with the aforesaid structure, which can provide similar effects.

(Tenth Embodiment)

Figure 41A:
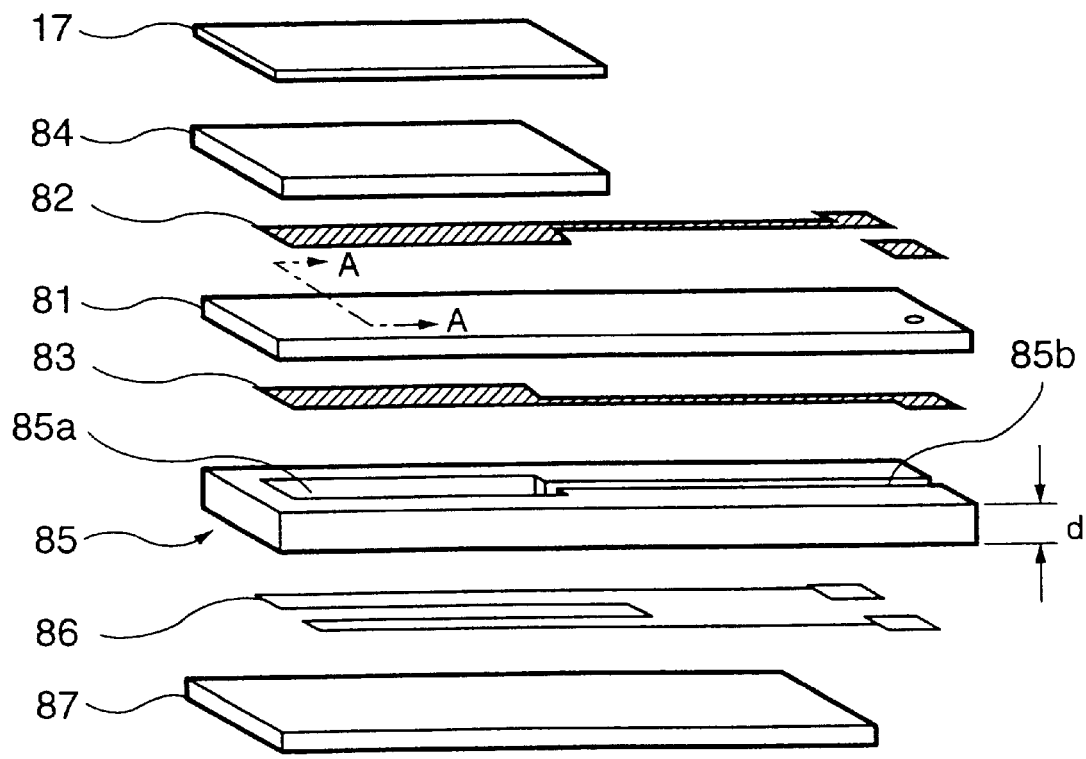
FIG. 41A is a development showing a structure of a gas detecting element with a laminated structure according to a tenth embodiment of this invention.
Figure 41B:
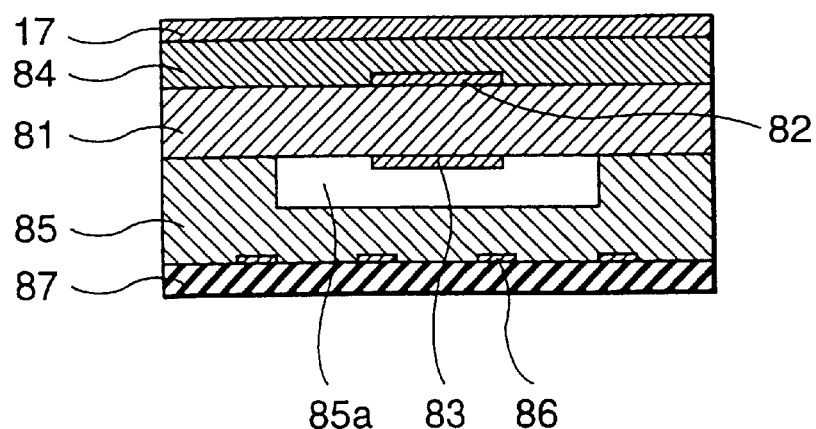
FIG. 41B is a cross-sectional view taken along a line A—A of FIG. 41A.

Although in the above description of the embodiments the first and second electrodes are formed on the inner and outer circumferential surfaces of the test-tube-like oxygen ion conductive solid electrolyte for producing the gas detecting device 11, the configuration of the gas detecting device 11 is not limited to this, but it is also appropriate that the gas detecting device 11 is configured as a laminated structure as shown in FIGS. 41A and 41B (which constitutes a tenth embodiment or modification of this invention). In the illustrations, a first electrode 82 and a second electrode 83 are formed in an opposed relation on upper and lower surfaces of a flat-plate-like oxygen ion conductive electrolyte 81 to constitute a laminated construction. Further, a catalyst layer 17 is placed on a porous film 84 forming a protective coat or a diffusion resistance layer on the exhaust gas side first electrode 82, while a flat-plate-like support 85, which defines an atmosphere chamber 85a and an atmosphere passage 85b communicating therewith, is put on the lower surface of the atmosphere side second electrode 83. Still further, a heater 86 and an insulating sheet 87 are placed on the lower surface of the support 85 in a laminated condition. Such a gas detecting device 11 is also applicable to the aforesaid $O_2$ sensor or air-fuel ratio sensor, and even in this case, similar effects are obtainable.

(Eleventh Embodiment)

Figure 42:
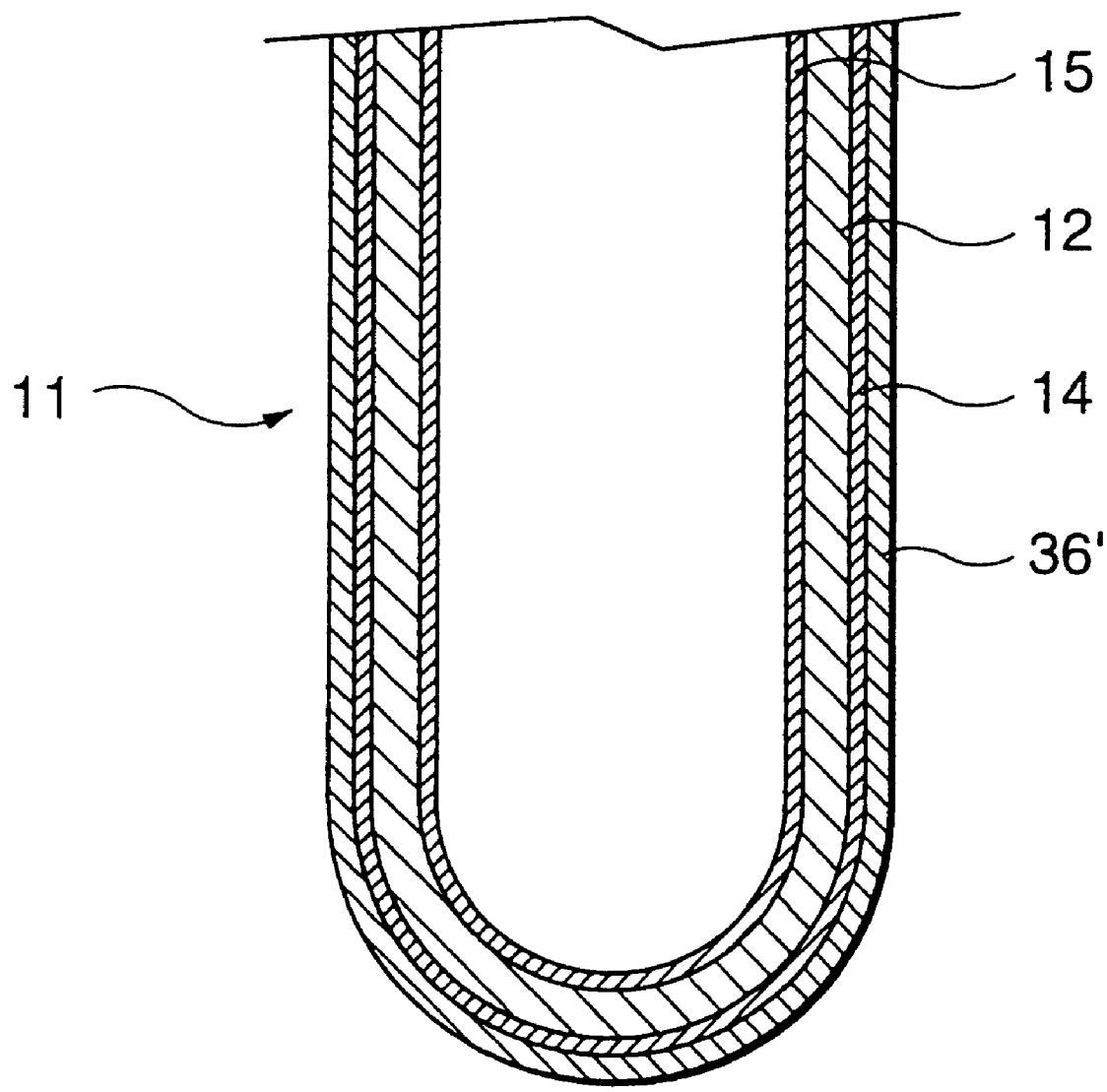
FIG. 42 is an enlarged cross-sectional view showing a principal portion of an $O_2$ sensor for a natural-gas-fueled engine according to an eleventh embodiment of this invention.

This embodiment relates to an $O_2$ sensor for air-fuel ratio control for a natural-gas-fueled engine, which has the entire construction shown in FIG. 28. FIG. 42 is an enlarged cross-sectional view showing a principal portion of a gas detecting device 11 constituting an $O_2$ sensor according to this embodiment. As shown in FIG. 42, as well as the above-described sixth embodiment, the gas detecting device 11 comprises an oxygen ion conductive solid electrolyte 12 made of zirconia or the like and shaped into a test-tube configuration, an inside electrode 15 serving as a first electrode and placed along an inner circumferential surface of the solid electrolyte 12, and an outside electrode 14 acting as a second electrode and placed along an outer circumferential surface of the solid electrolyte 12. These electrodes 14, 15 are made of, for example, platinum (Pt) or the like, and are formed by using a common means, such as deposition. Further, these electrodes 14, 15 are connected through output metallic terminals (141, 142) pressed into contact with a surface of the oxygen ion conductive solid electrolyte 12 to the lead wires (34).

A protective coat 36' being a coating layer is formed on an outer surface of the outside electrode 14. This protective coat 36' is for protecting the outside electrode 14 surface from harmful matters in an exhaust gas, and a porous film made of a ceramic such as a spinel ($MgO.Al_2O_3$) is suitably used as the protective coat 36'.

The feature of this embodiment is that the protective coat 36' is made using a porous film whose average pore is above 1000 Å. Whereupon, this can sufficiently reduce the difference in diffusion velocity between $H_2$ and $O_2$ contained in an exhaust gas to prevent the sensor output slippage. Preferably, the pores whose average pore diameter is 1000 Å contribute 90% or more of all the pores so that the diffusion velocity difference between $H_2$ and $O_2$ comes down to approximately zero, which can eliminate the influence of $H_2$.

The formation of the protective coat 36' can be done using, for example, a plasma spraying apparatus. The plasma spraying method is such that a heated and molten sprayed material is plasma-jetted to be blown against a surface of a sprayed object at a high speed. As the spraying material, there is a powder of ceramic such as a spinel ($MgO.Al_2O_3$) constituting the protective coat 36', and as an operating gas, there is a mixture of argon (Ar) and Nitrogen ($N_2$). A plasma arc voltage is usually within a range of approximately 50 to 60V and a plasma arc current is commonly within a range of approximately 500 to 700 A, and further, the distance from a plasma gun to the sprayed object is approximately 80 to 100 mm. The pore diameter of the protective coat 36' is adjustable with the grain size of the ceramic powder being a sprayed material and the spraying power. In general, the pore diameter expands as the grain size of the ceramic powder becomes smaller or as the spraying power becomes lower.

Besides, considering the stability of the sensor output, the mechanical strength and others, it is preferable that the thickness of the protective coat 36' is within a range of approximately 100 to 200 $\mu$m.

Secondly, a description will be given hereinbelow of an operation of the protective coat 36' in the $O_2$ sensor with the foregoing structure. In FIG. 42, in the gas detecting device 11, the exhaust gas passing through the protective coat 36' is introduced to the outside electrode 14 while the atmosphere is introduced to the inside electrode 15. At this time, in the oxygen ion conductive solid electrolyte 12, there occurs an electromotive force corresponding to the difference in oxygen concentration between the inside electrode 15 and the outside electrode 14. The sensor output is theoretically supposed to rapidly vary at the excess air factor ($\lambda$)=1.0 (see "theoretical value" in FIG. 29).

Figure 29:
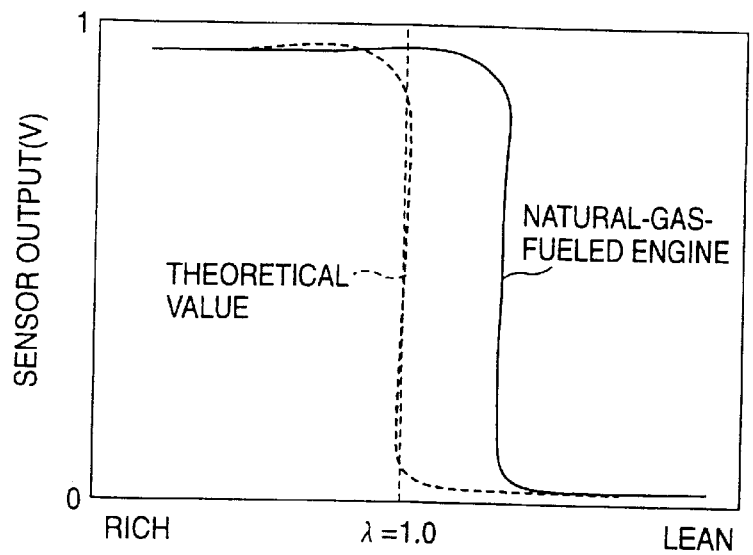
FIG. 29 is an illustration of a sensor output characteristic of a natural-gas-fueled engine.

Meanwhile, $H_2$ twice or three times that in a gasoline engine exists in an exhaust gas from a natural-gas-fueled engine, and when the pores of the protective coat 36' has a small diameter, the excess air factor ($\lambda$) at which the sensor output rapidly varies shifts to the lean side (see "natural-gas-fueled engine" in FIG. 29). This may be because, when the pore diameter of the protective coat 36' is small, the gas diffusion is ruled by the Knudsen flow and a difference is made between the diffusion velocities of $H_2$ and $O_2$.

Figure 43:
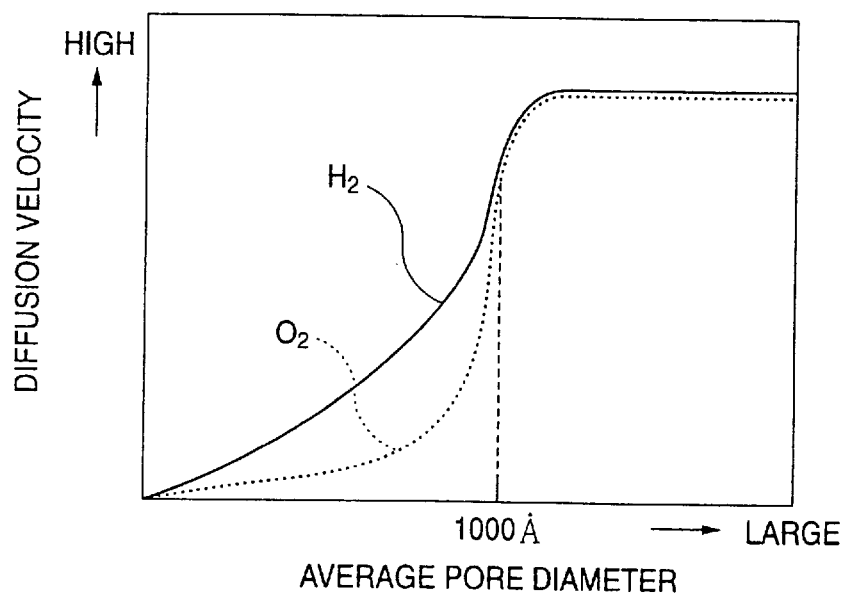
FIG. 43 is an illustration of the relationship between a pore diameter and a diffusion velocity.

FIG. 43 shows the result of measurement on the relationship between the average pore diameter of the protective coat 36' and the diffusion velocity. The formation of samples for the measurement and the measurement of the pore diameter are as follows.

As shown in FIG. 43, in an area where the pore diameter of the protective coat 36' is below 1000 Å, the diffusion velocity of $H_2$ having a low molecular weight becomes increasingly higher as compared with $O_2$. In this case, $H_2$ passes through the protective coat 36' at a higher speed than $O_2$, and then reaches the surface of the outside electrode 14, with the result that the outside electrode 14 goes into a $H_2$ richer condition than the actual condition. That is, the shortage of $O_2$ occurs on the surface of the outside electrode 14, so that the output characteristic of the $O_2$ sensor results in the fact that the rapidly output varying point shifts to the lean side (see FIG. 29) with respect to the theoretical value. In consequence, the $\lambda$-value in the $O_2$ feedback control system shifts, which can cause the deterioration of the exhaust emission.

Figure 44:
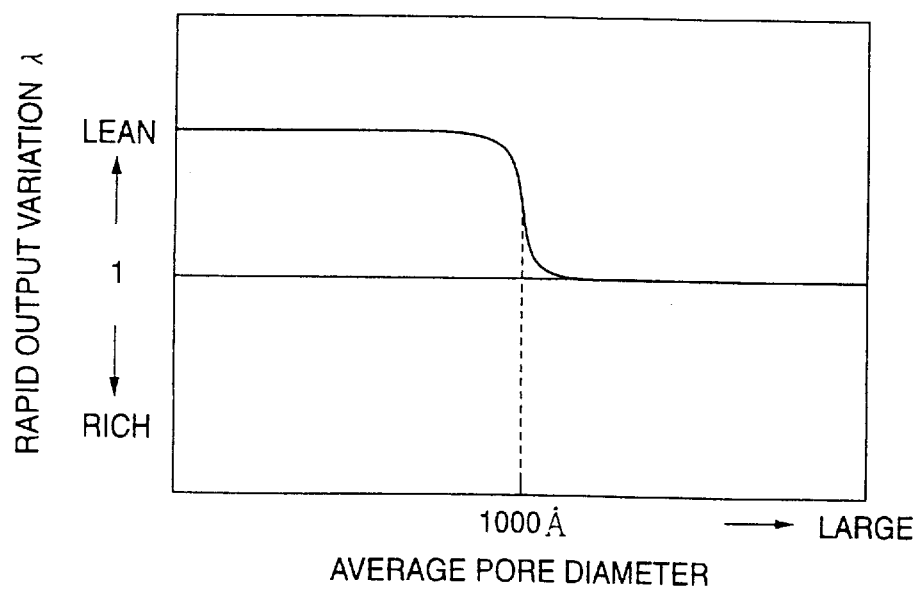
FIG. 44 is an illustration of the relationship between a pore diameter and a sensor output.

On the other hand, in an area where the average pore diameter of the protective coat 36' is above 1000 Å, as shown in FIG. 43, the diffusion velocity difference between $H_2$ and $O_2$, which causes the output slippage, comes to approximately zero. Accordingly, the shortage of $O_2$ on the surface of the outside electrode 14 is eliminable, thus preventing the output characteristic slippage. FIG. 44 shows the results of the examination on the relationship between the average pore diameter and the rapidly varying excess air factor ($\lambda$). As shown in FIG. 44, the sensor output shifts to the lean side when the average pore diameter is below 1000 Å, whereas the excess air factor ($\lambda$) substantially comes to 1 at the average pore diameter=1000 Å, where no output slippage occurs.

(Twelfth Embodiment)

Figure 45:
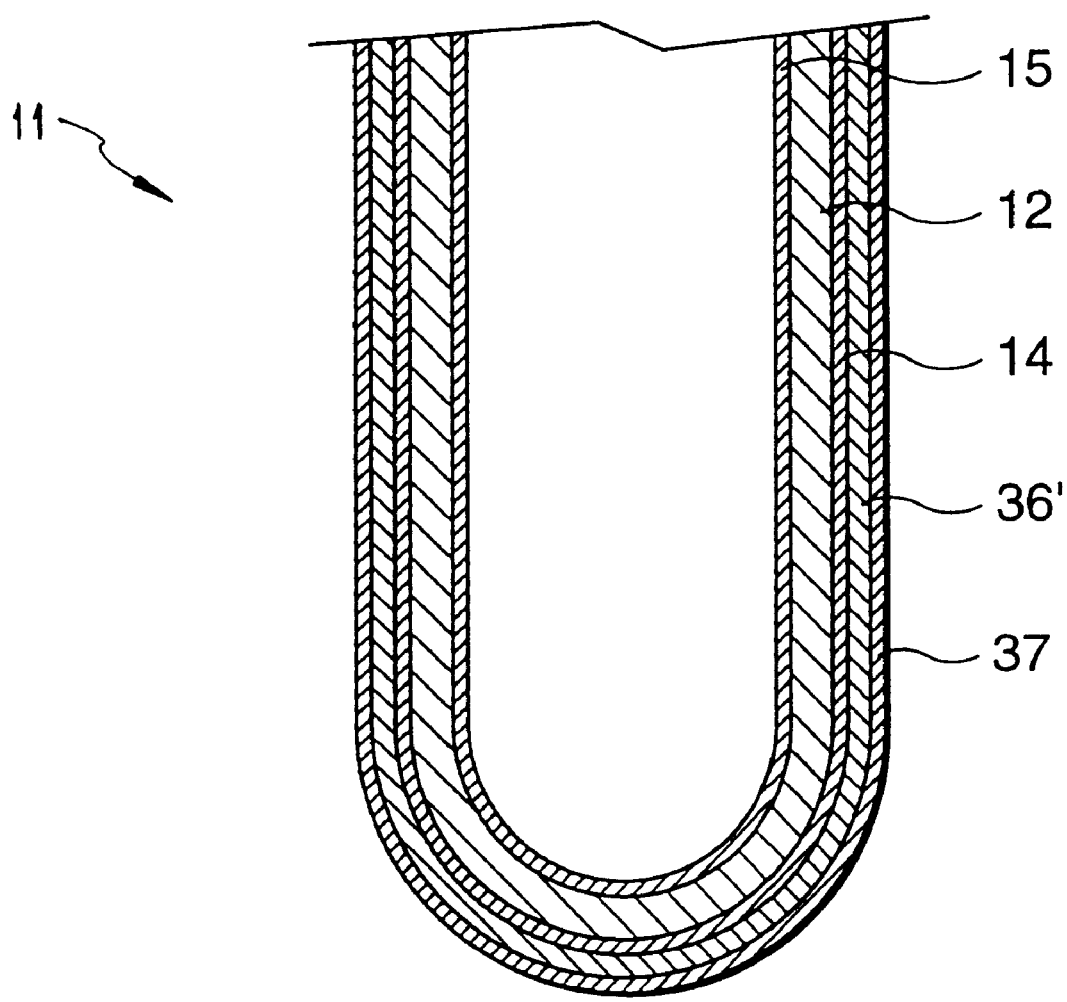
FIG. 45 is an enlarged cross-sectional view showing a principal portion of an $O_2$ sensor according to a twelfth embodiment of this invention.

FIG. 45 is an illustration of a twelfth embodiment of this invention. In this embodiment, in addition to the structure of the $O_2$ sensor according to the tenth embodiment, a trap layer 37 is provided to cover the outside of the coating layer 36'. The other structure is the same as that of the above-described eleventh embodiment. The trap layer 37 is made of a porous calcined substance, such as a ceramic ($Al_2O_3$ or the like), and usually, its porosity is preferably set to be 40 to 60%. In addition, it is preferable that thickness of the trap layer 37 is below 100 $\mu$m. The installation of this trap layer 37 prevents the deposit component produced by the combustion of an engine oil or the like from invading in the protective coat 36', so that the closing of the pores of the protective coat 36' is avoidable.

(Thirteenth Embodiment)

Figure 46:
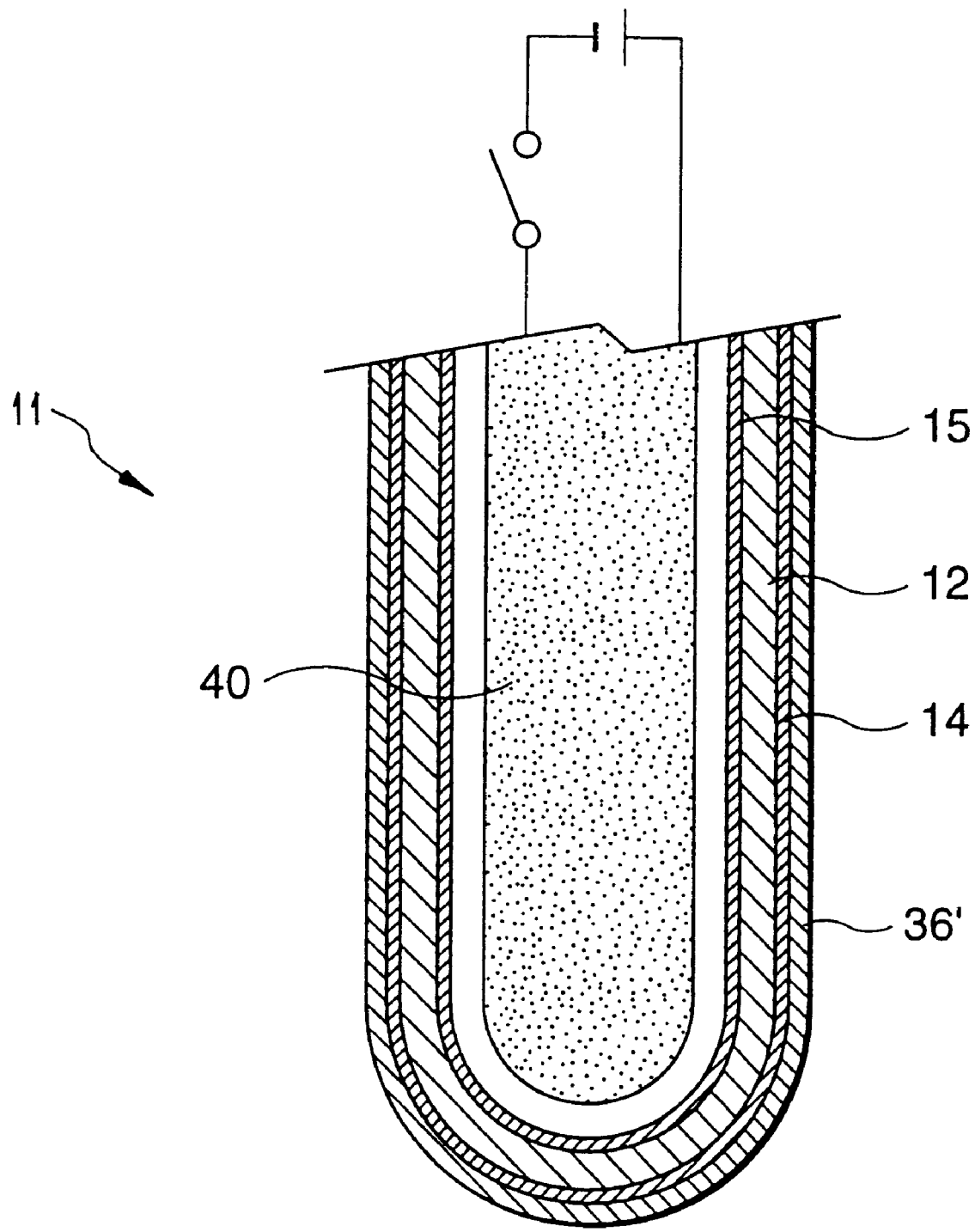
FIG. 46 is an enlarged cross-sectional view showing a principal portion of an $O_2$ sensor according to a thirteenth embodiment of this invention.

FIG. 46 is an illustration of a twelfth embodiment of this invention. A feature of this embodiment is that a sensor-heating heater 40 is provided within a hollow section of the oxygen ion conductive solid electrolyte 12 of the $O_2$ sensor constructed as shown in FIG. 42. The other structure is the same as that of the eleventh embodiment. the heater 40 is constructed using an insulator having a bar-like, plate-like or tube-like configuration, and for example, is constructed by embedding a heating element, such as tungsten (W) and molybdenum (Mo), in the interior of $Al_2O_3$ or the like. The heating element is connected through lead wires to an external power supply. The power to be supplied to the heater 40 is controlled in accordance with a map made out in advance on the basis of the engine conditions, or is feedback-controlled on the basis of the resistance value of the heater 40, so that the temperature of the protective coat 36' becomes above 500° C.

With this structure, the installation of the heater 40 can burn the deposit component produced by the combustion of an engine oil or the like, thereby preventing the closing the pores of the protective coat 36'. In addition, the heater 40 quickly activates the sensor to shorten the feedback-control-difficult time such as the engine cold start, thus preventing the deterioration of the emission.

(Fourteenth Embodiment)

Figure 47:
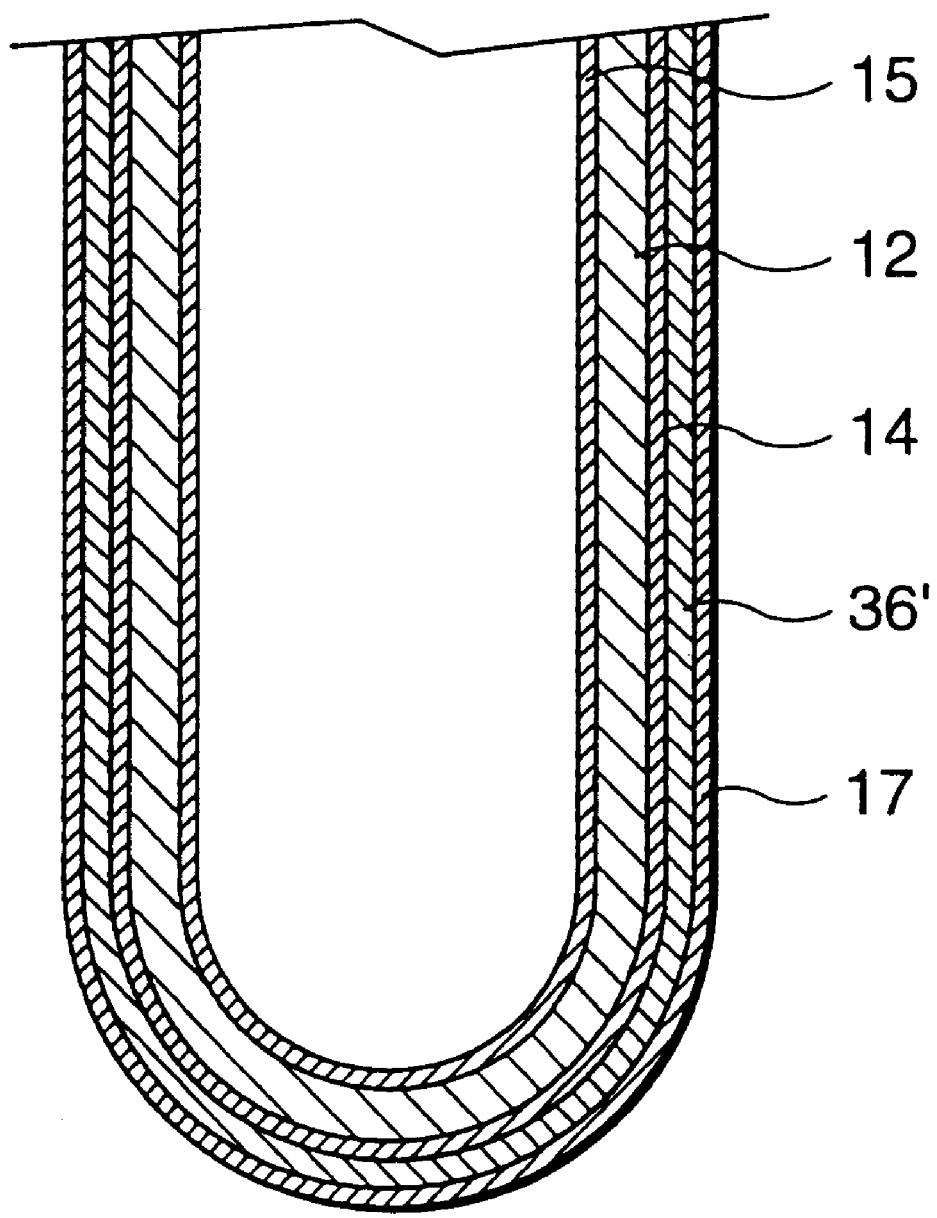
FIG. 47 is an enlarged cross-sectional view showing a principal portion of an $O_2$ sensor according to a fourteenth embodiment of this invention.

FIG. 47 is an illustration of a fourteenth embodiment of this invention. In this embodiment, the outer surface of the protective coat 36' is coated with a catalyst layer 17 exerting an oxidizing action. The catalyst layer 17 is made by carrying a catalytic metal (Pt, Pt—Rh, or the like) in a porous ceramic, such as alumina ($Al_2O_3$), and oxidizing $H_2$ contained in an exhaust gas before $H_2$ reaches the protective coat 36'. In this case, it is preferable that the catalytic-metal carried quantity to total weight of the catalyst layer 17 is set to be 0.5 to 5 wt %. In addition, usually, it is desirable that the thickness of the catalyst layer 17 is set to be below 50 $\mu$m. The addition of the catalyst layer 17 can oxidize $H_2$ of the exhaust gas within the catalyst layer 17 to reduce $H_2$ which arrives at the protective coat 36'. Whereupon, the sensor output slippage resulting from $H_2$ is more surely preventable.

(Fifteenth Embodiment)

Figure 48A:
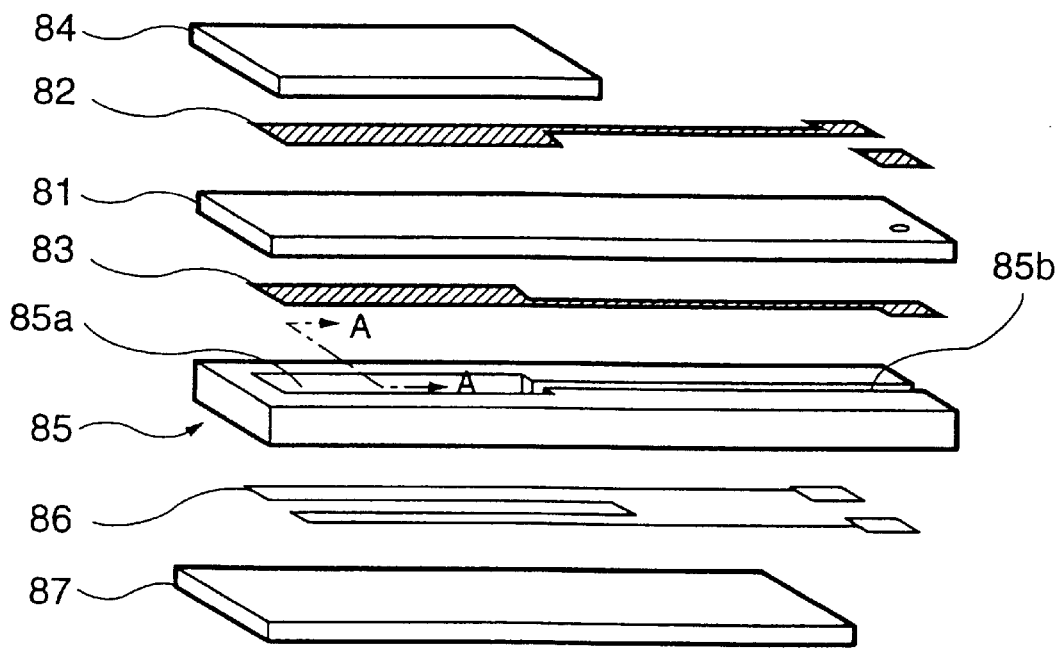
FIG. 48A is a development showing a structure of a gas detecting element according to a fifteenth embodiment of this invention.
Figure 48B:
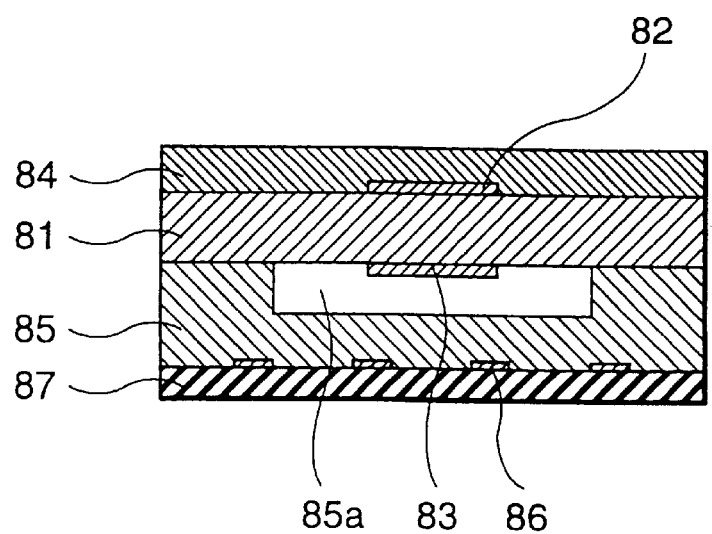
FIG. 48B is a cross-sectional view taken along a line A—A of FIG. 48A.

FIGS. 48A and 48B are illustrations of a fifteenth embodiment of this invention.

Although in the above description of the embodiments the first and second electrodes are formed on the inner and outer circumferential surfaces of the test-tube-like oxygen ion conductive solid electrolyte for producing the gas detecting device 11, the configuration of the gas detecting device 11 is not limited this, but it is also appropriate that, as shown in FIGS. 48A and 48B, a first electrode 82 and a second electrode 83 are formed in an opposed relation on upper and lower surfaces of a flat-plate-like oxygen ion conductive electrolyte 81 to constitute a laminated construction. Further, a protective coat 84 is formed on the exhaust gas side first electrode 82, while a flat-plate-like support 85, which defines an atmosphere chamber 85a and an atmosphere passage 85b communicating therewith, is put on the lower surface of the atmosphere side second electrode 83. Still further, a heater 86 and an insulating sheet 87 are placed on the lower surface of the support 85 in a laminated condition.

Although in the above-described embodiments this invention is applied to the $O_2$ sensor for the air-fuel ratio control for a natural-gas-fueled engine, this invention is not limited to this, but is applicable to various natural-gas-fueled engine gas sensors, such as an air-fuel ratio sensor for detecting an air-fuel ratio in a wider range.

(Sixteenth Embodiment)

Figure 49A:
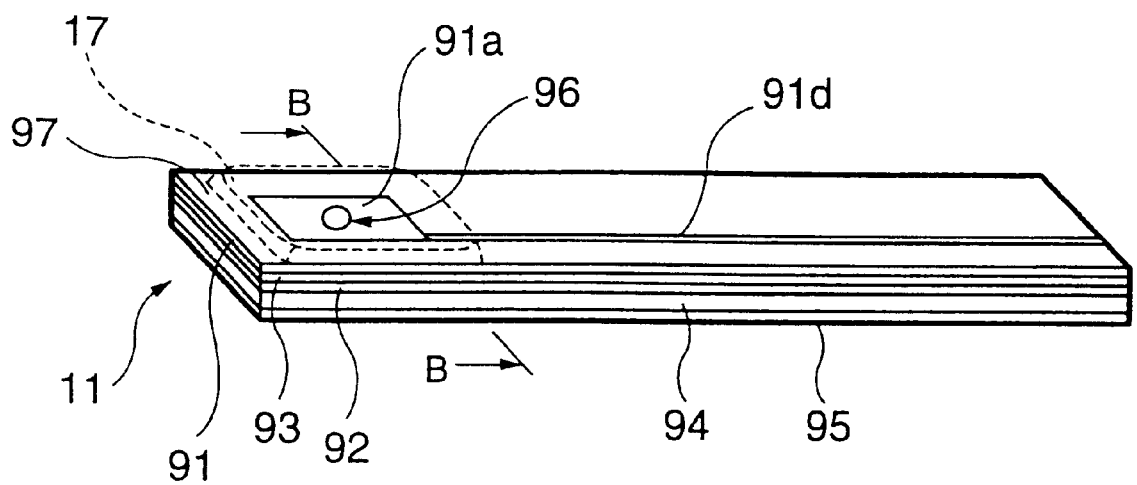
FIG. 49A is a perspective view showing a principal portion of a wide-area air-fuel ratio sensor according to a sixteenth embodiment of this invention.
Figure 49B:
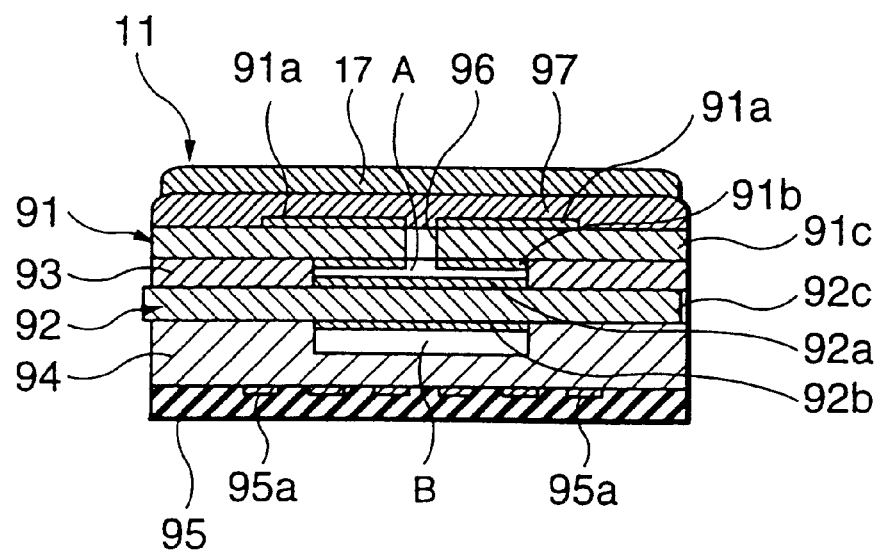
FIG. 49B is a cross-sectional view taken along a line B—B of FIG. 49A.

FIGS. 49A and 49B are illustrations of a sixteenth embodiment of this invention. This embodiment relates to the application of this invention to a two-cell type air-fuel ratio. The entire structure of this embodiment is substantially the same as that of the air-fuel ratio sensor shown in FIG. 36, and the description of this embodiment will be limited to the configuration of a gas detecting device 11 which constitutes the difference therefrom. In FIGS. 49A and 49B, the gas detecting device 11 is constructed in a manner that a pump cell 91 in which a pair of pump electrodes 91a, 91b are respectively formed on upper and lower surfaces of a flat-plate-like oxygen ion conductive solid electrolyte 91c is piled up through a spacer 93 on a sensor cell 92 in which a pair of sensor electrodes 92a, 92b are respectively formed on upper and lower surfaces of a flat-plate-like oxygen ion conductive solid electrolyte 92c. In the interior of the spacer 93, there is defined an exhaust gas chamber A whose two surfaces, i.e., upper and lower surface, are covered with both the cells 91, 92, with the pump electrode 91b and the sensor electrode 92a being exposed or positioned within the exhaust gas chamber A. Under the sensor cell 92, a heater section 95 with heater electrodes 95a for heating both the cells 91, 92 is further placed through another spacer 94 in a laminated condition. Within the spacer 94, there is formed an atmosphere chamber B into which introduced is the atmosphere which constitutes a reference oxygen concentration gas, with the sensor electrode 92b appearing therein. In FIG. 49A, numeral 91d denotes lead wires for energization.

In the pump cell 91, a communication hole 96 is made which penetrates the pair of pump electrodes 91a, 91b so that an exhaust gas is introduced through the communication hole 96 into the exhaust gas chamber A. On the upper surface of the pump cell 91 exposed to the exhaust gas, a diffusion resistance layer 97 is formed to cover the exhaust gas side of the communication hole 96 and the pump electrode 91a, and a catalyst layer 17 exhibiting an oxidizing effect is formed on a surface of the diffusion resistance layer 97. The structures of the diffusion resistance layer 97 and the catalyst layer 17 are the same as those shown in FIG. 36, where the catalyst carried quantity of the catalyst layer 17 is set to be 0.5 to 2 wt %, thereby preventing the sensor output slippage while maintaining the response characteristic.

A description will be made hereinbelow of the detection principle of the two cell type air-fuel ratio sensor. The pair of sensor electrodes 92a, 92b of the sensor cell 92 are exposed within the exhaust gas chamber A taking in the exhaust gas and further within the atmosphere chamber B taking in the atmosphere, respectively, and an electromotive force corresponding to the difference in oxygen concentration between these gases occurs between the pair of sensor electrodes 92a, 92b. Thus, when a voltage is applied through the lead wires 91d to the pump cell 91 so that a sensing current developing between the pair of sensor electrodes 92a, 92b assumes a constant value, that is, the oxygen concentration within the exhaust gas chamber A comes to a constant value, the oxygen ions accordingly move within the solid electrolyte 91c. At this time, a pumping current flowing in the pump cell 91 goes into a correlation relation to the oxygen concentration in the exhaust gas, so that the measurement of this pumping current allows the detection of an air-fuel ratio.

Although the two cell type air-fuel ratio sensor similarly creates a problem about the sensor output slippage when a large amount of $H_2$ exists in the exhaust gas like a natural-gas-fueled engine, the formation of the catalyst layer 15 on the surface of the diffusion resistance layer 97 removes $H_2$ of the exhaust gas introduced into the exhaust gas chamber A, thus resulting in the prevention of the output slippage. In addition, since the heater section 95 and the pump cell 91 are separated from each other, the heat from the heater section 95 is hard to transfer to the pump cell 91. Nevertheless, the temperature rise of the pump cell 91 is effectively achievable by the heat generated in the catalyst layer 17, which shortens the activation time to permit the quicker sensor operation. Thus, the reduction effects of the exhaust emission and the heater power are likewise attainable.

(Seventeenth Embodiment)

Figure 50:
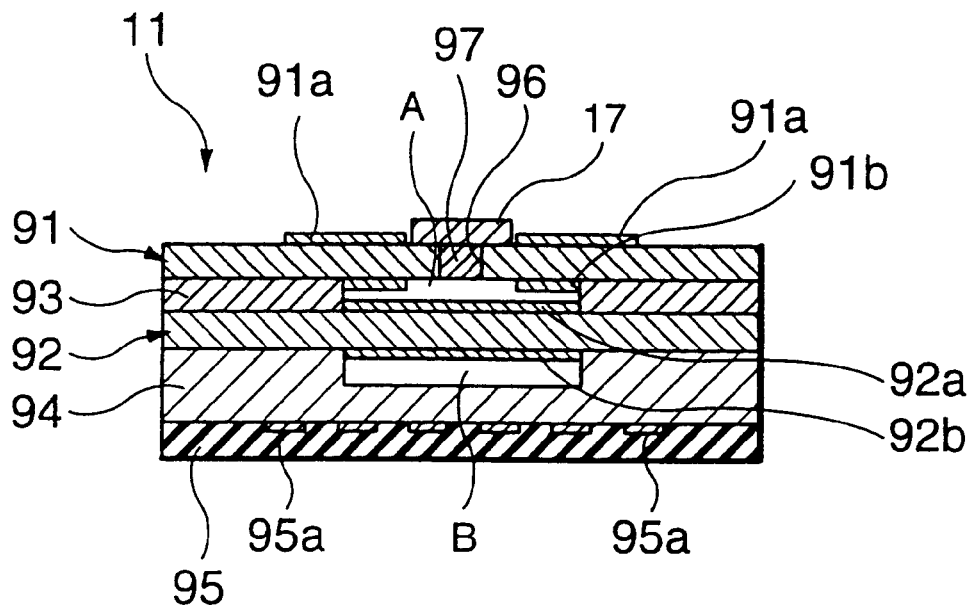
FIG. 50 is an enlarged cross-sectional view showing a principal portion of a wide-area air-fuel ratio sensor according to a seventeenth embodiment of this invention.

FIG. 50 is an enlarged cross-sectional view showing a principal portion of a wide-area air-fuel ratio sensor according to a seventeenth embodiment of this invention.

Although in the structure shown in FIGS. 49A and 49B the diffusion resistance layer 97 is formed on the exhaust gas side of the communication hole 96, there is no problem even if, as shown in FIG. 50, the diffusion resistance layer 97 is formed in the interior of the communication hole and the catalyst layer 17 is formed to cover the exhaust gas side surface of the diffusion resistance layer 97.

(Eighteenth Embodiment)

Figure 51:
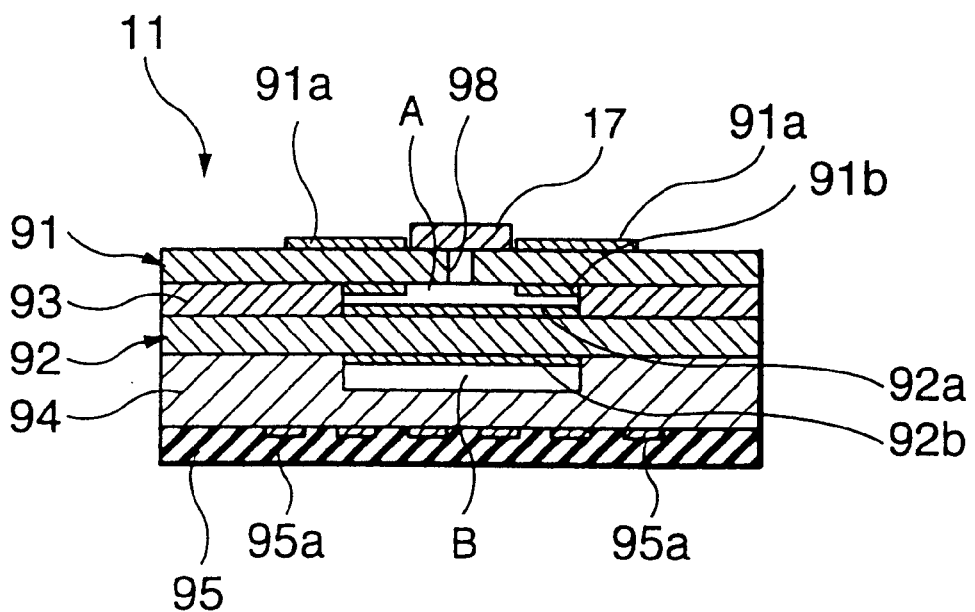
FIG. 51 is an enlarged cross-sectional view showing a principal portion of a wide-area air-fuel ratio sensor according to an eighteenth embodiment of this invention.

FIG. 51 is an enlarged cross-sectional view showing a principal portion of a wide-area air-fuel ratio sensor according to an eighteenth embodiment of this invention.

In this embodiment, as shown in FIG. 51, a pin hole 98 exerting an oxidizing action is provided in a place of the diffusion resistance layer 97. In this case, the catalyst layer 17 is formed on the exhaust gas side of the pin hole 98. This embodiment can offer similar effects to those of the above-described embodiments.

(Nineteenth Embodiment)

Figure 52:
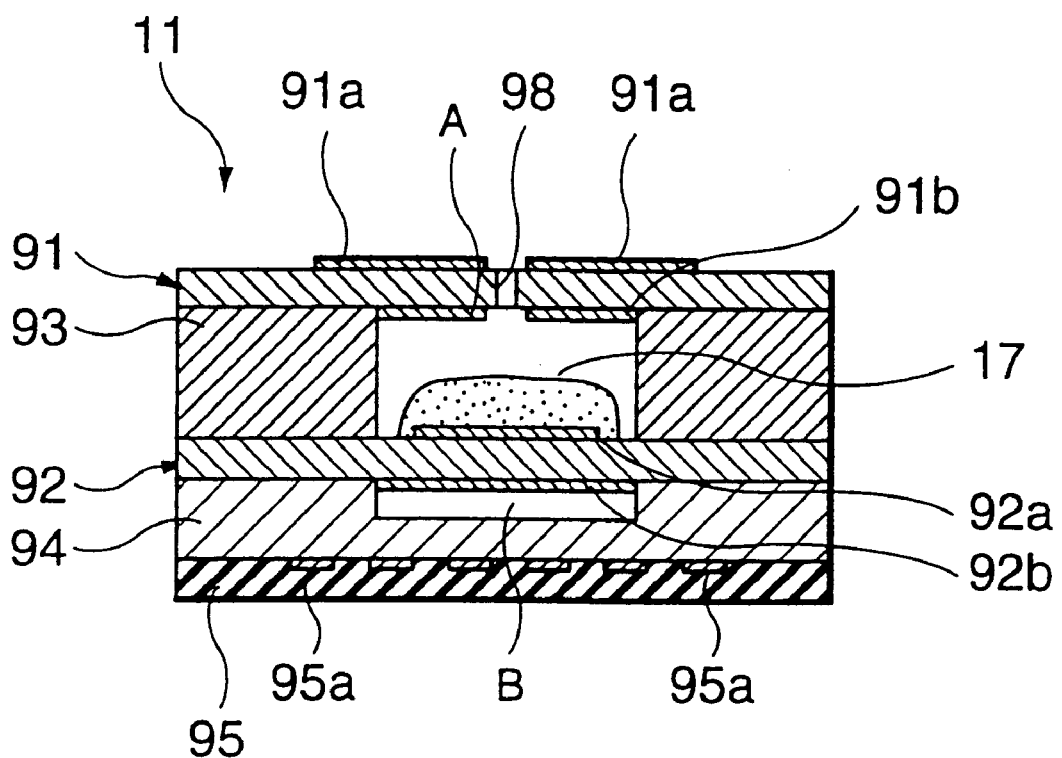
FIG. 52 is an enlarged cross-sectional view showing a principal portion of a wide-area air-fuel ratio sensor according to a nineteenth embodiment of this invention.

FIG. 52 is an enlarged cross-sectional view showing a principal portion of a wide-area air-fuel ratio sensor according to a nineteenth embodiment of this invention.

In this embodiment, in a structure where a pin hole 98 is made, the catalyst layer 17 is formed on a surface of the sensor electrode 92a appearing within the exhaust gas chamber A. That is, it is also possible that the catalyst layer 17 is provided on the exhaust gas chamber A side. In this case, the position of the formation of the catalyst layer 17 is not under any limitation as long as it stands in a range from the exhaust gas chamber A side end portion of the pin hole 98 to the sensor electrode 92a. Without being limited to the pin hole 98, in a structure in which provided is the diffusion resistance layer 97 constituting the different diffusion resistance means, it is also acceptable that the catalyst layer 17 is formed on the exhaust gas chamber A side.

(Twentieth Embodiment)

Figure 53A:
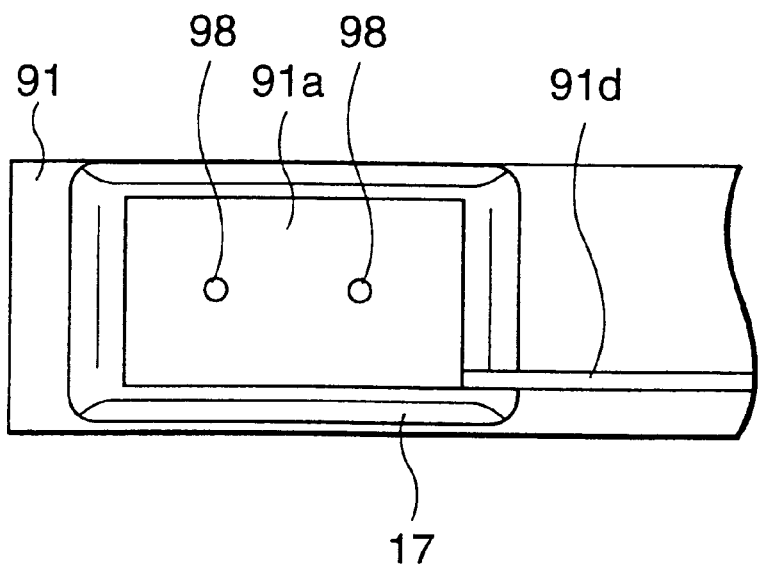
FIG. 53A is an enlarged view showing a principal portion of a wide-area air-fuel ratio sensor according to a twentieth embodiment of this invention.
Figure 53B:
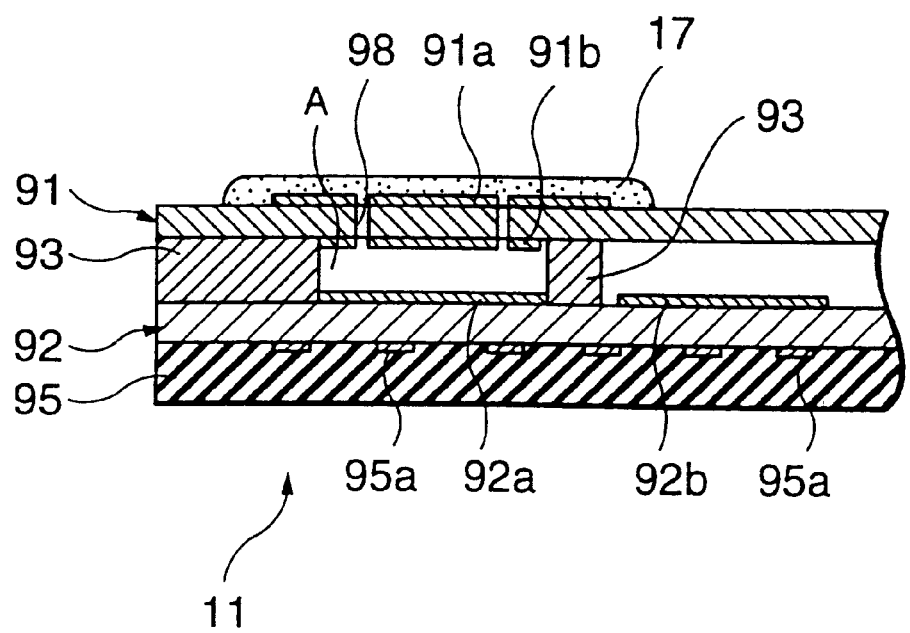
FIG. 53B is an enlarged cross-sectional view showing the principal portion shown in FIG. 53A.

FIG. 53A is an enlarged view showing a principal portion of a wide-area air-fuel ratio sensor according to a twentieth embodiment of this invention, and FIG. 53B is an enlarged cross-sectional view showing the principal portion.

In this embodiment, a plurality of communication holes or pin holes 98 for introducing an exhaust gas into the exhaust gas chamber A are made as shown in FIGS. 53A and 53B. In addition, in this embodiment, the atmosphere chamber B is defined within the spacer 93 as well as the exhaust gas chamber A. This can accomplish a further compact device structure.

(Twenty-First Embodiment)

Figure 54A:
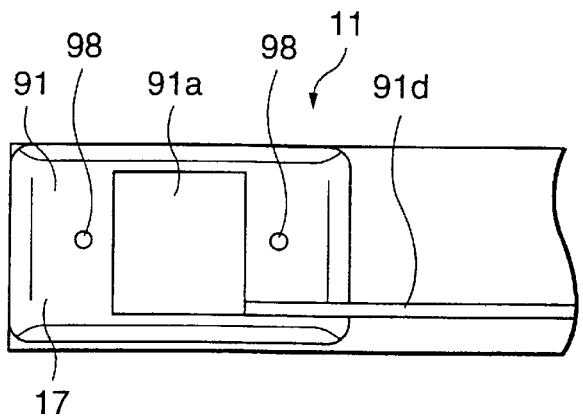
FIG. 54A is an enlarged view showing a principal portion of a wide-area air-fuel ratio sensor according to a twenty-first embodiment of this invention.
Figure 54B:
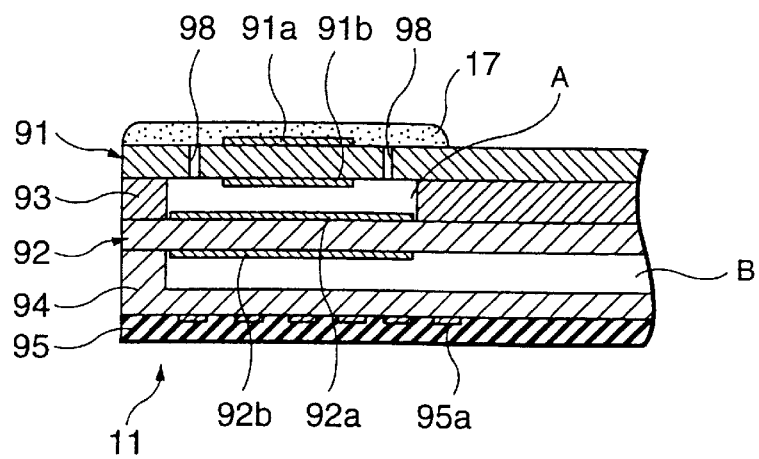
FIG. 54B is an enlarged cross-sectional view showing the principal portion shown in FIG. 54A.

FIG. 54A is an enlarged view showing a principal portion of a wide-area air-fuel ratio sensor according to a twenty-first embodiment of this invention, and FIG. 54B is an enlarged cross-sectional view showing the principal portion.

In this embodiment, a plurality of communication holes or pin holes 98 are made around the pump electrode 91a. In this embodiment, the pump cell 91 and the sensor cell 92 constitute the upper and lower surfaces of the exhaust gas chamber A.

(Twenty-Second Embodiment)

Figure 55:
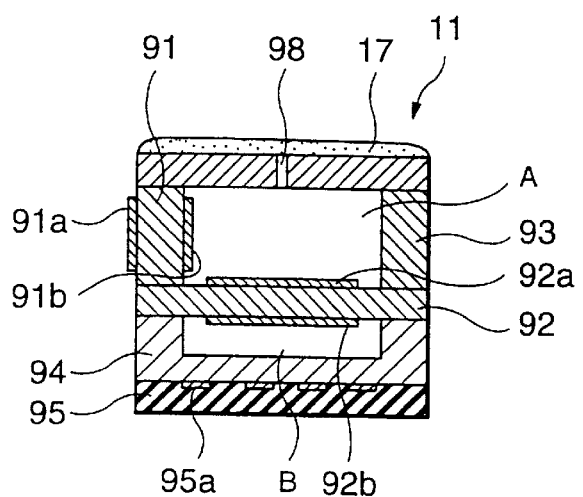
FIG. 55 is an enlarged view showing a principal portion of a wide-area air-fuel ratio sensor according to a twenty-second embodiment of this invention.

FIG. 55 is an enlarged view showing a principal portion of a wide-area air-fuel ratio sensor according to a twenty-second embodiment of this invention.

In this embodiment, unlike the twenty-first embodiment in which the pump cell 91 and the sensor cell 92 constitute the upper and lower surfaces of the exhaust gas chamber A, the pump cell 91 constitutes a side surface of the exhaust gas chamber A. Further, in this embodiment, the communication hole or pin hole 98 is made in the upper surface of the exhaust gas chamber A, and the catalyst layer 17 is formed to cover that surface.

(Twenty-Third Embodiment)

Figure 56A:
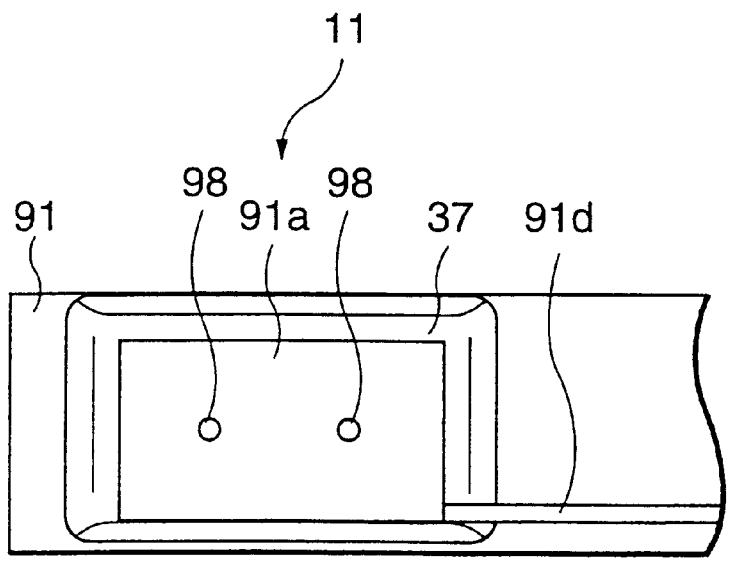
FIG. 56A is an enlarged view showing a principal portion of a wide-area air-fuel ratio sensor according to a twenty-third embodiment of this invention.
Figure 56B:
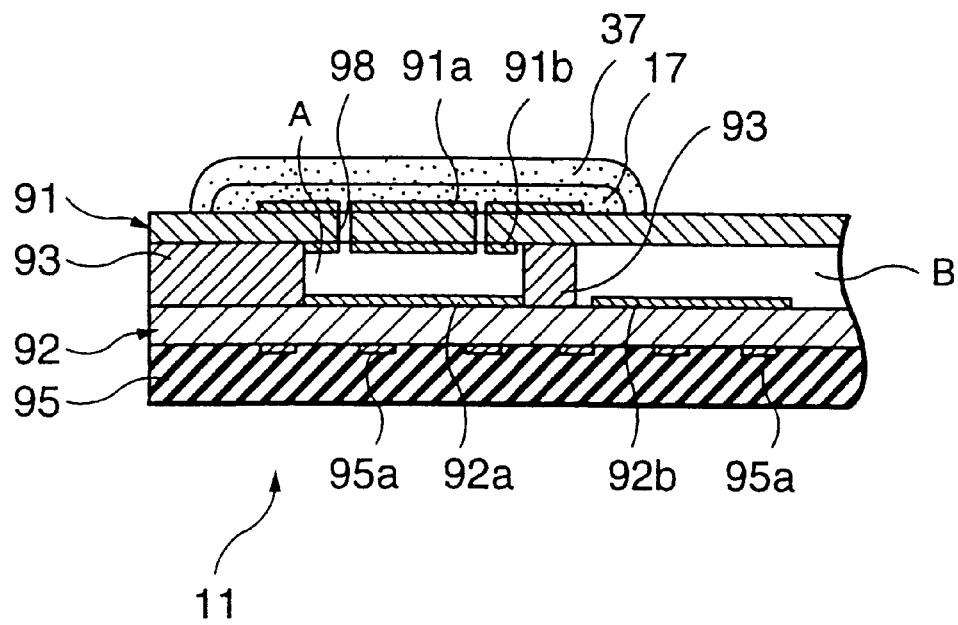
FIG. 56B is an enlarged cross-sectional view showing the principal portion shown in FIG. 56A.

FIG. 56A is an enlarged view showing a principal portion of a wide-area air-fuel ratio sensor according to a twenty-third embodiment of this invention, and FIG. 56B is an enlarged cross-sectional view showing the principal portion.

In this embodiment, a trap layer 37 is provided on a surface of the catalyst layer 17. In this case, although the trap layer 37 is added to the structure shown in FIGS. 53A and 53B, it is also appropriate to add the trap layer 37 to the other structures.

(Twenty-Fourth Embodiment)

Figure 57A:
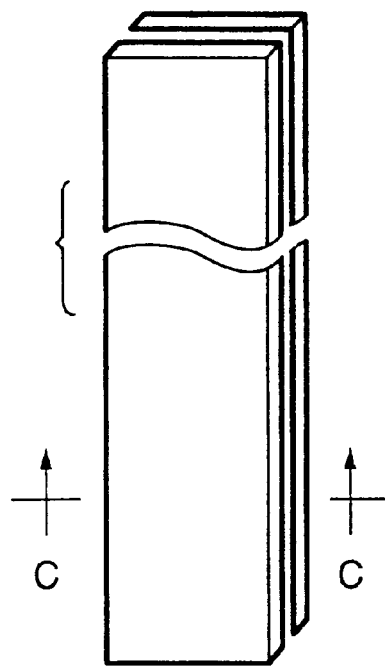
FIG. 57A is a perspective view showing a principal portion of a wide-area air-fuel ratio sensor according to a twenty-fourth embodiment of this invention.
Figure 57B:
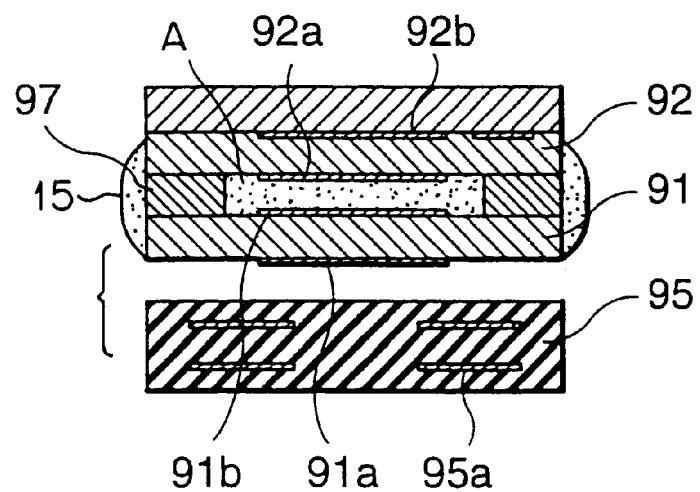
FIG. 57B is a cross-sectional view taken along line C—C of FIG. 57A.

FIG. 57A is a perspective view showing a principal portion of a wide-area air-fuel ratio sensor according to a twenty-fourth embodiment of this invention, and FIG. 57B is a cross-sectional view taken along line C—C of FIG. 57A.

In this embodiment, diffusion resistance layers 97 are formed on both side surface of the exhaust gas chamber A other than the upper and lower surfaces which are covered with the pump cell 91 and the sensor cell 92, and further, the catalyst layers 15 are provided to cover the diffusion resistance layers 97. In this case, the heater section 95 is located on the pump cell 91 side at a given interval in an opposed relation with respect to the pump cell 91, which contributes to easy temperature rise of the pump cell 91.

Although in the above-described embodiments this invention is applied to the $O_2$ sensor for the air-fuel ratio control for a natural-gas-fueled engine or the wide-area air-fuel ratio sensor for a natural-gas-fueled engine or a gasoline engine, this invention is not limited to this, but is applicable to various natural-gas-fueled engine gas sensors, such as a sensor which indirectly detects a different component on the basis of the variation of the oxygen concentration in a gas.

It should be understood that the foregoing relates to only preferred embodiments of the present invention, and that it is intended to cover all changes and modifications of the embodiments of the invention herein used for the purpose of the disclosure, which do not constitute departures from the spirit and scope of the invention.

What is claimed is:

1. An air-fuel ratio control system for a gas-fueled engine, comprising:

an exhaust purification catalyst provided in an exhaust passage of said engine;

an air-fuel ratio sensor located on the upstream side of said exhaust purification catalyst in said exhaust passage, said sensor comprising an element made of a solid electrolyte, and an atmosphere side electrode being formed on one side surface of said element while an exhaust gas side electrode being formed on the other side surface thereof, said exhaust gas side electrode having on a surface thereof a coating layer of porous film having an average pore diameter greater than 1000 angstroms (A);

a gas injector for supplying said engine with a fuel whose principal component is a natural gas; and air-fuel ratio control means for controlling a quantity of fuel supplied by said gas injector to reduce a difference between an air-fuel ratio measured by said air-fuel ratio sensor and a target air-fuel ratio.

2. The air-fuel ratio control system as defined in claim 1, wherein 90% or more of said pores of said coating layer have a diameter of above 1000 angstroms (A).

3. The air-fuel ratio control system as defined in claim 1, further comprising, on a surface of said coating layer, a trap layer made of a porous material whose porosity is from 40 to 50%.

4. An air-fuel ratio control system for a gas-fueled engine, comprising:

an exhaust purification catalyst provided in an exhaust passage of said engine;

an air-fuel ratio sensor located on the upstream side of said exhaust purification catalyst in said exhaust passage, said sensor comprising an element made of a solid electrolyte, an atmosphere side electrode being formed on one side surface of said element and an exhaust gas side electrode being formed on the other side surface thereof, said exhaust gas side electrode being coated with a catalyst layer carrying a catalyst by 0.5 to 2 wt % which removes hydrogen through catalytic reaction;

a gas injector for supplying said engine with a fuel whose principal component is a natural gas; and air-fuel ratio control means for controlling a quantity of fuel supplied by said gas injector to reduce a difference between an air-fuel ratio measured by said air-fuel ratio sensor and a target air-fuel ratio.

5. The air-fuel ratio control system as defined in claim 4, wherein porosity of said catalyst layer is from 10 to 25%.

6. The air-fuel ratio control system as defined in claim 4, wherein said catalyst layer is formed such that a porous ceramic carries a catalyst.

7. The air-fuel ratio control system as defined in claim 4, further comprising, on a surface of said catalyst layer, a trap layer made of a porous material whose porosity is from 40 to 50%.

* * * * *